US010626126B2

(12) United States Patent
Hunt et al.

(10) Patent No.: US 10,626,126 B2
(45) Date of Patent: *Apr. 21, 2020

(54) COMPOUNDS

(71) Applicant: Pulmocide Limited, London (GB)

(72) Inventors: Simon Fraser Hunt, Nottingham (GB); Stuart Thomas Onions, Nottingham (GB); Vladimir Sherbukhin, Nottingham (GB); Euan Alexander Fraser Fordyce, Nottingham (GB); Jennifer Claire Thomas, Nottingham (GB); Peter John Murray, London (GB); Matthew Stephen Coates, London (GB); Daniel William Brookes, London (GB); Kazuhiro Ito, London (GB); Peter Strong, London (GB)

(73) Assignee: PULMOCIDE LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/091,707

(22) PCT Filed: Apr. 7, 2017

(86) PCT No.: PCT/GB2017/050979
§ 371 (c)(1),
(2) Date: Oct. 5, 2018

(87) PCT Pub. No.: WO2017/175000
PCT Pub. Date: Oct. 12, 2017

(65) Prior Publication Data
US 2019/0092791 A1  Mar. 28, 2019

(30) Foreign Application Priority Data

Apr. 8, 2016 (EP) .................... 16164542

(51) Int. Cl.
*C07D 495/14* (2006.01)
*A61P 31/14* (2006.01)
*A61K 31/55* (2006.01)
*C07D 519/00* (2006.01)
*C07D 493/10* (2006.01)

(52) U.S. Cl.
CPC ............ *C07D 519/00* (2013.01); *A61K 31/55* (2013.01); *A61P 31/14* (2018.01); *C07D 493/10* (2013.01); *C07D 495/14* (2013.01)

(58) Field of Classification Search
CPC .... C07D 495/14; C07D 519/00; A61K 31/55; A61P 31/14
See application file for complete search history.

(56) References Cited

U.S. PATENT DOCUMENTS

| 5,840,298 | A  | * | 11/1998 | Brams ................. | C07K 14/005 |
|           |    |   |         |                        | 424/133.1   |
| 5,843,913 | A  | * | 12/1998 | Li ........................ | C07K 14/005 |
|           |    |   |         |                        | 514/44 R    |
| 8,999,969 | B2 | * | 4/2015  | Mackman ............  | C07D 495/04 |
|           |    |   |         |                        | 514/215     |
| 9,732,098 | B2 | * | 8/2017  | Hunt ....................  | C07D 495/04 |
| 9,926,335 | B2 |   | 3/2018  | Hunt et al.            |             |
| 10,035,810| B2 |   | 7/2018  | Hunt et al.            |             |
| 10,189,863| B2 | * | 1/2019  | Hunt ....................  | C07D 495/04 |
| 2012/0263715 | A1 | * | 10/2012 | Richter ............. | C07K 16/1027 |
|           |    |   |         |                        | 424/133.1   |
| 2017/0226129 | A1 |   | 8/2017 | Yu et al.               |             |
| 2017/0355717 | A1 |   | 12/2017| Hunt et al.             |             |
| 2018/0319820 | A1 |   | 11/2018| Hunt et al.             |             |

FOREIGN PATENT DOCUMENTS

| WO | WO-2005061698 A1 | * | 7/2005 | ............. A61K 35/76 |
| WO | WO 2011/005842 A1 |   | 1/2011 | |
| WO | WO 2016/022464 A  |   | 2/2016 | |
| WO | WO 2017/134133 A1 |   | 8/2017 | |

OTHER PUBLICATIONS

Hohman et al., European Journal of Internal Medicine vol. 19 pp. 319-324, published 2008 (Year: 2008).*
Coates et al., "Preclinical Characterization of PC786, an Inhaled Small-Molecule Respiratory Syncytial Virus L Protein Polymerase Inhibitor," Antimicrobial Agents and Chemotherapy, vol. 61, No. 9, Sep. 2017 (posted online Jun. 26, 2017), pp. 1-18.
Sudo et al., "YM-53403, a Unique Anti-respiratory Syncytial Virus Agent with a Novel Mechanism of Action," Antiviral Research, vol. 65, 2005, pp. 125-131.
Xiong, et al., "Discovery of a Potent Respiratory Syncytial Virus RNA Polymerase Inhibitor," Bioorganic and Medical Chemistry Letters, vol. 23, No. 24, 2013 (Available online Oct. 16, 2013), pp. 6789-6793, XP028788018.
Zheng et al., "The Use of Spirocyclic Scaffolds in Drug Discovery," Bioorganic and Medical Chemistry Letters, vol. 24, No. 16, 2014 (Available online Jul. 5, 2014), pp. 3673-3682, XP029041745.

* cited by examiner

*Primary Examiner* — Timothy P Thomas
*Assistant Examiner* — George W Kosturko
(74) *Attorney, Agent, or Firm* — Birch, Stewart, Kolasch & Birch, LLP

(57) ABSTRACT

There are provided 5,6-dihydro-4H-dithieno[3,2-b:2',3'-d] azepine derivatives(as defined in the disclosure) which are useful in the treatment of RSV infection and for the prevention of disease associated with RSV infection.

20 Claims, No Drawings

COMPOUNDS

FIELD OF THE INVENTION

The invention relates to novel compounds, compositions containing them, processes for making said compounds and their use in therapy. The compounds are intended to treat or prevent respiratory syncytial virus infections and associated disease particularly infections caused by the A and B strains thereof.

BACKGROUND OF THE INVENTION

Human respiratory syncytial virus (RSV) is a pneumovirus of the paramyxovirus family and the most common cause of bronchiolitis and pneumonia in infants under one year of age. Most children become infected with RSV prior to their second birthday resulting in 75-125,000 hospitalizations. The associated medical costs are thought to exceed $650 million annually in the United States alone. In addition, early-life, respiratory viral infections, notably with RSV, increase the risk of the subsequent development of childhood asthma (Holt and Sly, 2002.). RSV infection can produce severe, lower respiratory tract disease in patients of any age. The elderly, as well as those having compromised cardiac, pulmonary or immune systems are particularly vulnerable and it is estimated that some 14,000 deaths occur annually in the United States in subjects over 65 years old. In addition, RSV infection is increasingly regarded as an important precipitator of exacerbations in patients suffering from chronic obstructive pulmonary disease (COPD) (Mohan et al., 2010) as well as asthma (Newcomb and Peebles, 2009) and cystic fibrosis (Abman et al., 1988). In immunocompromised adults approximately 50% of upper respiratory tract infections with RSV progress to pneumonia.

The initial portal of entry by RSV is through the nose or eye rather than the mouth (Hall et al., 1981). Once established in the upper respiratory tract the virus is able to migrate readily into the lungs. The pathophysiology of RSV infection was investigated in a study of lung tissues obtained from deceased children (Johnson et al., 2007). Examination of tissues from four individuals revealed immunostaining of epithelial cells indicating the presence of RSV, without basal cells being affected. The epithelial localisation of the pathogenic organism provides a challenge to treatment since a supra-effective concentration of the drug substance has to be maintained at the discrete cellular site to enable the infection to be treated and subsequently cleared.

The RSV virus exists as two antigenic sub-groups: A and B. Viruses of the RSV A strain were formerly regarded as the sub-group pathogens responsible for the majority of clinical disease and were reported to produce a more symptomatic pathology (Walsh et al., 1997; Panayiotou et al., 2014). A common RSV A strain was RSV A2 (Olivier et al., 2009). However, during a recent outbreak in China virus strains from the RSV B sub-group were found to predominate in the afflicted population (Zhang et al., 2010).

Over the last two decades considerable progress has been made in the treatment of a number of viral diseases including human immunodeficiency virus (HIV) and both hepatitis B and hepatitis C. In all these cases gold standard therapies have evolved that consist of combination treatments that were brought about, at least to some extent, in response to the emergence of drug resistant disease.

FDA-approved drugs for the treatment of acute RSV infections comprise of (aerosolised) ribavirin and the humanised monoclonal antibody, palivizumab (Synagis). The latter agent targets the RSV fusion (F) protein and is limited to prophylactic use in high risk paediatric patients. Furthermore, clinical variants resistant to neutralisation by palivizumab were recently identified (Zhu et al., 2011) and therefore no truly effective vaccine is currently available. The use of ribavirin is limited by its low potency against the virus and by concerns over its side-effect profile. Consequently there is an urgent, unmet need for the discovery of novel, safe and effective therapies against RSV infection having an improved clinical profile. Moreover, in view of the emerging prominence of the RSV B strains in clinical disease it is highly desirable that these treatments be efficacious against infections arising from both RSV A and RSV B strains.

SUMMARY OF THE INVENTION

In a first aspect, the invention provides a compound of formula (I),

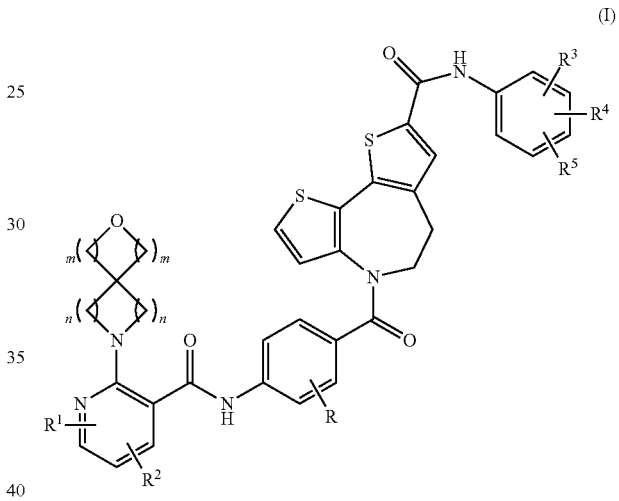

wherein:
R represents hydrogen or halo;
$R^3$ represents hydrogen, hydroxy, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ hydroxyalkyl, $C_{1-4}$ haloalkoxy, —O(CH$_2$)$_2$OH or —O(CH$_2$)$_2$O $C_{1-2}$ alkyl;
$R^4$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;
$R^5$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;
m and n represent integers which may be independently selected from 1 and 2;
and either
(a) $R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-2}$ alkoxy$C_{1-2}$ alkyl or $C_{1-4}$ haloalkoxy; and
$R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy, $C_{1-2}$ alkoxy$C_{1-2}$alkyl, $C_{1-4}$ hydroxyalkyl, or cyano; or
(b) $R^1$ and $R^2$ are in positions 6 and 5 respectively of the pyridine nucleus and are joined to form a bicyclic system comprising either a 5- or 6-membered carbocyclic ring or a 5- or 6-membered heterocyclic ring which contains heteroatoms selected only from O and S, which is fused to said pyridine nucleus; or a pharmaceutically acceptable salt thereof ("compounds of the invention").

Biological data disclosed in the Examples reveals that compounds of the invention inhibit the cytopathic effect associated with infection by RSV strains, particular RSV A and/or RSV B strains.

DETAILED DESCRIPTION OF THE INVENTION

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Lower alkyl as used herein refers to $C_{1-4}$ alkyl such as methyl, ethyl or tert-butyl.

Alkoxy as used herein refers to straight or branched chain alkoxy, for example methoxy, ethoxy, propoxy, butoxy. Alkoxy as employed herein also extends to embodiments in which one or two oxygen atoms (e.g. a single oxygen atom) is located within the alkyl chain, for example —$CH_2CH_2CH_2OCH_3$, —$CH_2CH_2OCH_3$, —$CH_2OCH_2CH_2OCH_3$, or —$CH_2OCH_3$. Thus in one embodiment the alkoxy is linked through carbon to the remainder of the molecule, for example —$C_n$alkyl-O—$C_m$alkyl in which n=1 or 2 and m=1 or 2. In one embodiment the alkoxy group is linked through oxygen to the remainder of the molecule, for example —$OC_{1-4}$alkyl. In one embodiment the disclosure relates to straight chain alkoxy. In one embodiment the alkoxy is linked through oxygen to the remainder of the molecule but the alkoxy group contains a further oxygen atom, for example —$OCH_2CH_2OCH_3$.

Halo or halogen includes fluoro, chloro, bromo or iodo, in particular fluoro, chloro or bromo, especially fluoro or chloro.

Alkyl substituted by halo (haloalkyl) as employed herein refers to alkyl groups having 1 to 6 halogen atoms, for example 1 to 5 halogens, such as per haloalkyl, in particular perfluoroalkyl, more specifically —$CF_2CF_3$ or $CF_3$.

Alkoxy substituted by halo (haloalkoxy) as employed herein refers to alkoxy groups having 1 to 6 halogen atoms, for example 1 to 5 halogens, such as perhaloalkoxy, in particular perfluoroalkoxy, more specifically —$OCF_2CF_3$ or —$OCF_3$.

$C_{1-4}$ alkyl includes $C_1$, $C_2$, $C_3$ and $C_4$ alkyl. $C_{1-4}$ alkoxy includes $C_1$, $C_2$, $C_3$ and $C_4$ alkoxy. $C_{1-4}$ haloalkyl includes $C_1$, $C_2$, $C_3$ and $C_4$ haloalkyl. $C_{1-4}$ haloalkoxy includes $C_1$, $C_2$, $C_3$ and $C_4$ haloalkoxy.

$C_{3-6}$ cycloalkyl denotes a saturated, optionally branched carbocycle containing 3-6 carbon atoms. Unbranched examples include cyclopropyl, cyclobutyl, cyclopentyl and cyclohexyl. Branched examples include 2-methylcyclopropyl.

$C_{2-4}$ alkynyl means an unsaturated aliphatic, optionally branched moiety containing at least one triple bond. Examples include —C≡CH, —$CH_2$—C≡CH, —CH($CH_3$)—C≡CH, —$CH_2$—C≡C—$CH_3$ and —C≡C—$CH_3$. Preferred alkynyl is $C_{2-3}$ alkynyl e.g. —C≡CH.

$C_{2-4}$ alkenyl signifies an unsaturated, aliphatic, optionally branched moiety containing at least one double bond and no triple bonds. Examples include —CH═$CH_2$, —$CH_2$—CH═$CH_2$, —CH($CH_3$)—CH═$CH_2$, —$CH_2$—CH═CH($CH_3$), —CH═CH—$CH_3$ and —CH═C($CH_3$)$_2$. A preferred alkenyl is $C_{2-3}$ alkenyl, such as vinyl.

$C_{1-2}$ alkoxy$C_{1-2}$ alkyl includes a moiety such as $CH_3OCH_2$—.

When $R^1$ and $R^2$ are in positions 6 and 5 respectively of the pyridine nucleus and are joined to form a bicyclic system comprising either a 5- or 6-membered carbocyclic ring or a 5- or 6-membered heterocyclic ring which contains heteroatoms selected only from O and S, which is fused to said pyridine nucleus, said bicyclic system may be partially unsaturated or fully aromatic. Said heterocyclic ring may suitably contain 1 or 2 (preferably 1) heteroatom(s) selected from O and S. In one embodiment said heterocyclic ring contains 1 heteroatom which is O. In another embodiment said heterocyclic ring contains 1 heteroatom which is S.

When $R^1$ and $R^2$ are in positions 6 and 5 respectively of the pyridine nucleus and are joined to form a bicyclic system comprising either a 5- or 6-membered carbocyclic ring or a 5- or 6-membered heterocyclic ring which contains heteroatoms selected only from O and S, which is fused to said pyridine nucleus, examples include partially unsaturated bicyclic systems, for example, 6,7-dihydro-5H-cyclopenta[b]pyridine, and 5,6,7,8-tetrahydroquinoline and fully aromatic bicyclic systems such as quinoline.

When $R^1$ and $R^2$ are in positions 6 and 5 respectively of the pyridine nucleus and are joined to form a bicyclic system comprising either a 5- or 6-membered carbocyclic ring or a 5- or 6-membered heterocyclic ring which contains heteroatoms selected only from O and S, which is fused to said pyridine nucleus, examples include fully aromatic bicyclic systems such as thienopyridines (e.g. thieno[2,3-b]pyridine, thieno[3,4-b]pyridine or thieno[3,2-b]pyridine) and partially unsaturated bicyclic systems including dihydropyranopyridines (e.g. 3,4-dihydro-2H-pyrano[2,3-b]pyridine, 6,8-dihydro-5H-pyrano[3,4-b]pyridine, 7,8-dihydro-2H-pyrano[4,3-b]pyridine or 3,4-dihydro-2H-pyrano[3,2-b]pyridine).

Suitably n represents 1. Suitably m represents 2. Suitably n represents 1 and m represents 2. According to a less preferred alternative, n represents 2 and m represents 1. According to another less preferred alternative, n represents 1 and m represents 1. According to a still less preferred alternative, n represents 2 and m represents 2.

In one embodiment of the present invention there is provided a compound of formula (Ia):

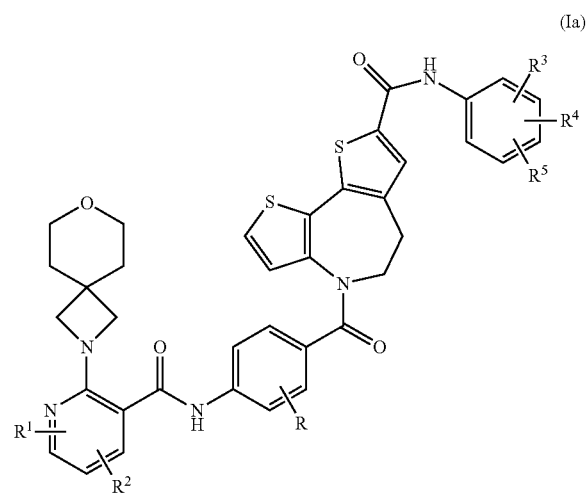

(Ia)

wherein R, $R^1$, $R^2$, $R^3$, $R^4$ and $R^5$ are as defined above for compounds of formula (I).

In a second embodiment of the invention there is provided a compound of formula (Ib):

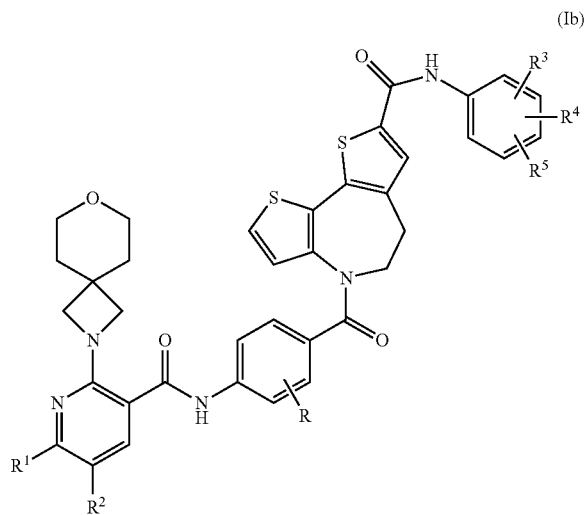

(Ib)

wherein R, $R^1$, $R^2$, $R^3$, $R^4$ and $R^5$ are defined as above for compounds of formula (I).

In a third embodiment of the invention there is provided a compound of formula (Ic):

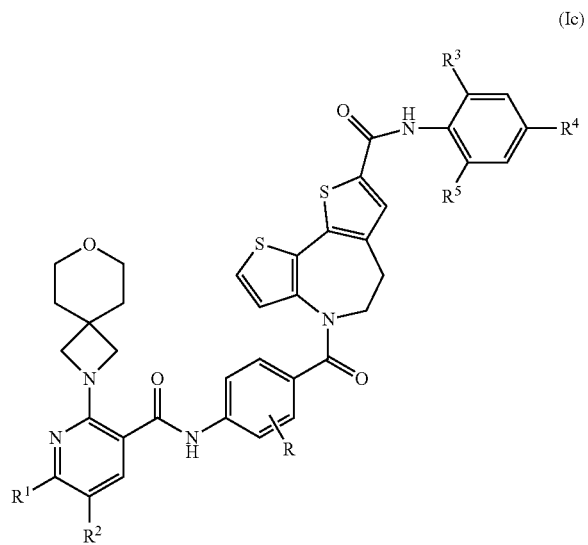

(Ic)

wherein R, $R^1$, $R^2$, $R^3$, $R^4$ and $R^5$ are defined as above for compounds of formula (I).

According to one embodiment of the invention as represented by structures (I), (Ia), (Ib) or (Ic):

R represents hydrogen or halo;

$R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

$R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy or cyano;

$R^3$ represents hydrogen, hydroxy, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

$R^4$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

$R^5$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

and m and n represent integers which may be independently selected from 1 and 2.

Particular embodiments of the invention, independently and in any combination, include the following:

R is preferably in the 3-position of the phenyl ring to which it is attached (i.e. the position adjacent to the carbonyl).

R is preferably hydrogen or fluoro, particularly hydrogen.

$R^1$ and $R^2$ are preferably, respectively, in the 6- and 5-positions of the pyridyl ring to which they are attached.

In an embodiment, $R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy; and $R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy or cyano.

In an embodiment, $R^1$ and $R^2$ are, respectively, in the 6- and 5-positions of the pyridyl ring to which they are attached, and are defined as follows: $R^1$ and $R^2$ represent H; $R^1$ and $R^2$ represent Me; $R^1$ represents OMe and $R^2$ represents H; $R^1$ represents Me and $R^2$ represents H; $R^1$ represents H and $R^2$ represents cyclopropyl; $R^1$ represents H and $R^2$ represents Me; $R^1$ represents H and $R^2$ represents Et; $R^1$ represents H and $R^2$ represents ethynyl; $R^1$ represents H and $R^2$ represents —$CH_2OMe$; $R^1$ represents H and $R^2$ represents F; $R^1$ represents H and $R^2$ represents Cl; $R^1$ represents H and $R^2$ represents OMe; or $R^1$ represents H and $R^2$ represents C(=$CH_2$)Me.

Preferably one of $R^1$ and $R^2$ is $C_{1-4}$ alkyl, more preferably methyl, and the other is hydrogen (for example $R^1$ is hydrogen and $R^2$ is methyl). Alternatively, $R^1$ and $R^2$ are both hydrogen. In another embodiment, $R^1$ and $R^2$ are both methyl.

In an embodiment (i) $R^1$ is hydrogen in the 6-position of the pyridine ring and $R^2$ is methyl in the 5-position of the pyridine ring; or (ii) $R^1$ is methyl in the 6-position of the pyridine ring and $R^2$ is hydrogen in the 5-position of the pyridine ring; or (iii) $R^1$ is methyl in the 6-position of the pyridine ring and $R^2$ is methyl in the 5-position of the pyridine ring; or (iv) $R^1$ and $R^2$ both represent hydrogen; or (v) $R^1$ is methoxy in the 6-position of the pyridine ring and $R^2$ is hydrogen in the 5-position of the pyridine ring; or (vi) $R^1$ is hydrogen in the 6-position of the pyridine ring and $R^2$ is cyclopropyl in the 5-position of the pyridine ring. Preferably $R^1$ is hydrogen in the 6-position of the pyridine ring and $R^2$ is methyl in the 5-position of the pyridine ring.

In an alternative embodiment, $R^1$ and $R^2$ are in positions 6 and 5 respectively of the pyridine nucleus and are joined to form a bicyclic system in which a 5- or 6-membered carbocyclic or heterocyclic ring is fused to said pyridine nucleus.

Preferably $R^3$ represents hydrogen, halo (e.g. fluoro or chloro), cyano, $C_{1-4}$ alkyl, $C_{2-4}$ alkenyl, $C_{2-4}$ alkynyl, $C_{1-4}$ haloalkyl, $C_{3-6}$ cycloalkyl or $C_{1-4}$ haloalkoxy.

Preferably $R^3$, $R^4$ and $R^5$ are selected from hydrogen, halo (e.g. fluoro or chloro), $C_{1-4}$ alkyl, $C_{2-4}$ alkenyl, $C_{2-4}$ alkynyl, $C_{1-4}$ haloalkyl, $C_{1-4}$ haloalkoxy, and cyano.

Preferably $R^5$ is selected from hydrogen, halo (e.g. fluoro or chloro), $C_{1-4}$ alkyl, $C_{2-4}$ alkenyl, $C_{2-4}$ alkynyl, $C_{1-4}$ haloalkyl, and $C_{1-4}$ haloalkoxy.

Preferably $R^4$ is hydrogen or halo (e.g. fluoro or chloro), especially hydrogen.

Preferably one of $R^3$, $R^4$ and $R^5$ is hydrogen and the remainder are substituent(s) other than hydrogen.

Alternatively, preferably, two of $R^3$, $R^4$ and $R^5$ is hydrogen and the remainder is a substituent other than hydrogen.

Preferably one of $R^3$, $R^4$ and $R^5$ is hydrogen and the remainder are selected from the group consisting of methyl, trifluromethyl, cyano and halo, more preferably methyl, trifluoromethyl, cyano and halo, still more preferably methyl, fluoro, chloro and trifluoromethyl, and most preferably methyl, fluoro and chloro.

When one of $R^3$, $R^4$ and $R^5$ is other than hydrogen the said group is preferably located in the 2-position of the phenyl ring to which it is attached. When two of $R^3$, $R^4$ and $R^5$ are other than hydrogen the said groups are preferably located in the 2- and 6-positions of the phenyl ring to which they are attached.

Alternatively, when two of $R^3$, $R^4$ and $R^5$ are other than hydrogen the said groups are preferably located in the 2- and 4-positions of the phenyl ring to which they are attached. When three of $R^3$, $R^4$ and $R^5$ are other than hydrogen the said groups are preferably located in the 2-, 4- and 6-positions of the phenyl ring to which they are attached.

When any of $R^3$, $R^4$ and $R^5$ are other than hydrogen, they are preferably halo, $C_{1-4}$ alkyl, $C_{2-4}$ alkenyl, $C_{2-4}$ alkynyl, $C_{1-4}$ haloalkyl, $C_{1-4}$ haloalkoxy or cyano and more preferably methyl, trifluromethyl, cyano or halo, and most preferably fluoro or chloro, particularly fluoro.

Suitably n represents 1 and m represents 2.

For example $R^3$, $R^4$ and $R^5$ taken together with the phenyl ring to which they are attached may be selected from: phenyl, 2-cyanophenyl, 2-fluorophenyl, 2-fluoro-6-iodophenyl, 2-cyclopropyl-6-fluorophenyl, 2-fluoro-6-methylphenyl, 2,6-difluorophenyl, 2-methylphenyl, 2-chlorophenyl, 2-ethylphenyl, 4-ethynylphenyl, 2,4-difluorophenyl, 2-fluoro-4-chlorophenyl, 2-fluoro-4-methylphenyl, 2-fluoro-4-methoxyphenyl, 2,6-dimethylphenyl, 2-chloro-6-fluorophenyl, 2-chloro-4-fluoro phenyl, 2,4,6-trifluorophenyl, 2,6-dichlorophenyl, 2-chloro-6-cyanophenyl, 2-cyano-6-methyl phenyl, 2-fluoro-6-vinylphenyl, 2-ethynyl-6-fluorophenyl, 2-cyano-6-fluorophenyl, 2-fluoro-6-hydroxyphenyl, 2-fluoro-6-methoxyphenyl, 2-fluoro-6-($OCH_2CH_2OH$)phenyl, 2-fluoro-6-($OCH_2CH_2OMe$)phenyl, 2-fluoro-6-($CH_2OH$)phenyl and 2-fluoro-6-trifluoromethylphenyl.

In particular $R^3$, $R^4$ and $R^5$ taken together with the phenyl ring to which they are attached may be selected from: phenyl, 2-fluorophenyl, 2-fluoro-6-methylphenyl, 2,6-difluorophenyl, 2,4-difluorophenyl, 2-chloro-6-fluorophenyl, 2,6-dichlorophenyl, 2,4,6-trifluorophenyl, 2-fluoro-6-methoxyphenyl, 2-fluoro-6-hydroxyphenyl and 2-chloro-6-cyanophenyl.

Exemplary compounds of formula (I) are selected from the group consisting of:

N-(2,6-difluorophenyl)-4-(4-(5-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;

4-(4-(2-(7-oxa-2-azaspiro[3.5]nonan-2-yl)-6,7-dihydro-5H-cyclopenta[b]pyridine-3-carbox amido)benzoyl)-N-(2,6-difluorophenyl)-5,6-dihydro-4H-dithieno[3,2-b:2',3'-d]azepine-8-carboxamide;

N-(2,6-difluorophenyl)-4-(4-(5-methyl-2-(7-oxa-2-azaspiro[3.5]nonan-2-yl)nicotinamido) benzoyl-2,3,5,6-d4)-5,6-dihydro-4H-dithieno[3,2-b:2',3'-d]azepine-8-carboxamide;

N-(2,6-difluorophenyl)-4-(4-(5,6-dimethyl-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2,6-difluorophenyl)-4-(2-fluoro-4-(6-methyl-2-(7-oxa-2-azaspiro[3.5]nonan-2-yl) nicotinamido)benzoyl)-5,6-dihydro-4H-dithieno[3,2-b:2:2',3'-d]azepine-8-carboxamide;

4-(4-(2-(7-oxa-2-azaspiro[3.5]nonan-2-yl)nicotinamido) benzoyl)-N-(2,6-difluoro phenyl)-5,6-dihydro-4H-dithieno[3,2-b:2',3'-d]azepine-8-carboxamide;

4-(4-(2-(7-oxa-2-azaspiro[3.5]nonan-2-yl)nicotinamido)-2-fluorobenzoyl)-N-(2,6-difluoro phenyl)-5,6-dihydro-4H-dithieno[3,2-b:2',3'-d]azepine-8-carboxamide;

4-(4-(5-methyl-2-(7-oxa-2-azaspiro[3.5]nonan-2-yl)nicotinamido)benzoyl)-N-phenyl-5,6-dihydro-4H-dithieno[3,2-b:2',3'-d]azepine-8-carboxamide;

N-(2-fluorophenyl)-4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide;

N-(2,4-difluorophenyl)-4-(4-(5-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2-fluoro-6-methylphenyl)-4-(4-(5-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2-chloro-6-fluorophenyl)-4-(4-(5-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2,6-dichlorophenyl)-4-(4-(5-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2-cyano-6-fluorophenyl)-4-(4-(5-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2-fluoro-6-hydroxyphenyl)-4-(4-(5-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2-fluoro-6-methoxyphenyl)-4-(4-(5-methyl-2-(7-oxa-2-azaspiro[3.5]nonan-2-yl)nicotin amido)benzoyl)-5,6-dihydro-4H-dithieno[3,2-b:2',3'-d]azepine-8-carboxamide;

4-(4-(5-methyl-2-(7-oxa-2-azaspiro[3.5]nonan-2-yl)nicotinamido)benzoyl)-N-(2,4,6-trifluoro phenyl)-5,6-dihydro-4H-dithieno[3,2-b:2',3'-d]azepine-8-carboxamide;

N-(2,6-difluorophenyl)-4-(2-fluoro-4-(5-methyl-2-(7-oxa-2-azaspiro[3.5]nonan-2-yl)nicotin amido)benzoyl)-5,6-dihydro-4H-dithieno[3,2-b:2',3'-d]azepine-8-carboxamide;

N-(2-chloro-6-fluorophenyl)-4-(2-fluoro-4-(5-methyl-2-(7-oxa-2-azaspiro[3.5]nonan-2-yl) nicotinamido)benzoyl)-5,6-dihydro-4H-dithieno[3,2-b:2',3'-d]azepine-8-carboxamide;

N-(2,6-difluorophenyl)-4-(4-(5-methoxy-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2,6-difluorophenyl)-4-(4-(6-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2,6-difluorophenyl)-4-(4-(6-methoxy-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2,6-difluorophenyl)-4-(4-(5,6-dimethyl-2-(7-oxa-2-azaspiro[3.5]nonan-2-yl)nicotinamido) -2-fluorobenzoyl)-5,6-dihydro-4H-dithieno[3,2-b:2',3'-d]azepine-8-carboxamide;

4-(4-(2-(7-oxa-2-azaspiro[3.5]nonan-2-yl)-6,7-dihydro-5H-cyclopenta[b]pyridine-3-carbox amido)benzoyl)-N-(2-fluoro-6-methylphenyl)-5,6-dihydro-4H-dithieno[3,2-b:2',3'-d]azepine-8-carboxamide;

N-(4-(8-((2,6-difluorophenyl)carbamoyl)-5,6-dihydro-4H-dithieno[3,2-b:2',3'-d]azepine-4-carbonyl)phenyl)-2-(7- oxa-2-azaspiro[3.5]nonan-2-yl)-7,8-dihydro-5H-pyrano [4,3-b]pyridine-3-carboxamide;
N-(4-(8-((2-fluoro-6-methylphenyl)carbamoyl)-5,6-dihydro-4H-dithieno[3,2-b:2',3'-d]azepine-4-carbonyl)phenyl)-2-(7-oxa-2-azaspiro[3.5]nonan-2-yl)-7,8-dihydro-5H-pyrano[4,3-b]pyridine-3-carboxamide;
4-(4-(2-(7-oxa-2-azaspiro[3.5]nonan-2-yl)quinoline-3-carboxamido)benzoyl)-N-(2,6-difluoro phenyl)-5,6-dihydro-4H-dithieno[3,2-b:2',3'-d]azepine-8-carboxamide;
4-(4-(5-(7-oxa-2-azaspiro[3.5]nonan-2-yl)thieno[3,2-b] pyridine-6-carboxamido)-2-fluoro benzoyl)-N-(2,6-difluorophenyl)-5,6-dihydro-4H-dithieno[3,2-b:2',3'-d] azepine-8-carboxamide;
4-(4-(2-(2-oxa-7-azaspiro[3.5]nonan-7-yl)nicotinamido) benzoyl)-N-(2,6-difluorophenyl)-5,6-dihydro-4H-dithieno[3,2-b:2',3'-d]azepine-8-carboxamide;
N-(2,6-difluorophenyl)-4-(4-(5-methyl-2-(2-oxa-7-azaspiro [3.5]nonan-7-yl)nicotinamido) benzoyl)-5,6-dihydro-4H-dithieno[3,2-b:2',3'-d]azepine-8-carboxamide;
4-(4-(2-(2-oxa-6-azaspiro[3.3]heptan-6-yl)nicotinamido) benzoyl)-N-(2,6-difluorophenyl)-5,6-dihydro-4H-dithieno[3,2-b:2',3'-d]azepine-8-carboxamide;
N-(2,6-difluorophenyl)-4-(4-(5-methyl-2-(2-oxa-6-azaspiro [3.3]heptan-6-yl)nicotinamido) benzoyl)-5,6-dihydro-4H-dithieno[3,2-b:2',3'-d]azepine-8-carboxamide;
4-(4-(2-(3-oxa-9-azaspiro[5.5]undecan-9-yl)nicotinamido) benzoyl)-N-(2,6-difluorophenyl)-5,6-dihydro-4H-dithieno[3,2-b:2',3'-d]azepine-8-carboxamide;
N-(2,6-difluorophenyl)-4-(4-(5-methyl-2-(3-oxa-9-azaspiro [5.5]undecan-9-yl)nicotinamido) benzoyl)-5,6-dihydro-4H-dithieno[3,2-b:2',3'-d]azepine-8-carboxamide;
and pharmaceutically acceptable salts of any one thereof.

Pharmaceutically acceptable salts of compounds of formula (I) include in particular pharmaceutically acceptable acid addition salts of said compounds. The pharmaceutically acceptable acid addition salts of compounds of formula (I) are meant to comprise the therapeutically active non-toxic acid addition salts that the compounds of formula (I) are able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like.

Conversely said salt forms can be converted by treatment with an appropriate base into the free base form.

Salts as referred to herein, for example in relation to intermediate compounds, include pharmaceutically acceptable salts, such as those above mentioned, as well as other salts that may be disfavoured for pharmaceutical use. Salts of acidic compounds include salts formed with positive ions of Group 1 and Group 2 metals including, sodium, potassium, calcium and magnesium ions as well as with inorganic cations such as ammonium ion.

The definition of compounds of formula (I) is intended to include all stereoisomers of said compounds. Stereoisomers as employed herein refers to isomeric molecules that have the same molecular formula and sequence of bonded atoms (constitution), but that differ only in the three-dimensional orientations of their atoms in space. This contrasts with structural isomers, which share the same molecular formula, but the bond connections and/or their order differ(s) between different atoms/groups. In stereoisomers, the order and bond connections of the constituent atoms remain the same, but their orientation in space differs.

The definition of compounds of formula (I) is intended to include all tautomers of said compounds.

The definition of compounds of formula (I) is intended to include all solvates of said compounds (including solvates of salts of said compounds) unless the context specifically indicates otherwise. Examples of solvates include hydrates.

The compounds of the disclosure include those where the atom specified is a naturally occurring or non-naturally occurring isotope. In one embodiment the isotope is a stable isotope.

Thus the compounds of the disclosure include, for example deuterium containing compounds and the like.

The disclosure also extends to all polymorphic forms of the compounds herein defined.

The compounds of the invention may be obtained by a general process (Scheme 1) whereby a thiophene carboxylic acid precursor of formula (II), wherein R, $R^1$, $R^2$, m and n are as defined above for compounds of formula (I), or a suitably protected derivative thereof; is reacted with an activating agent, to generate a reactive, electrophilic carboxylic acid derivative (such as with oxalyl chloride and DMF to give the acid chloride), followed by subsequent reaction with an amine of formula (III), wherein $R^3$, $R^4$ and $R^5$ are as defined for compounds of formula (I), or a suitably protected derivative thereof.

Scheme 1

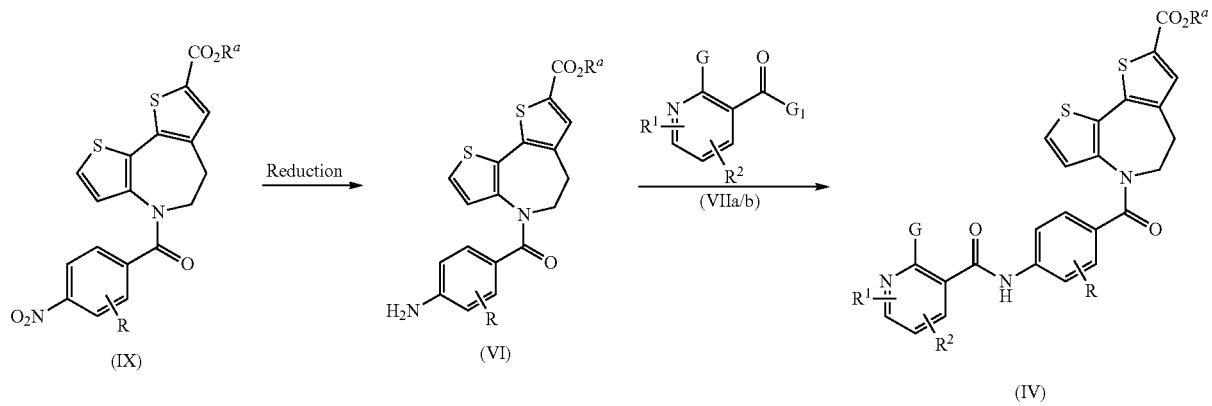

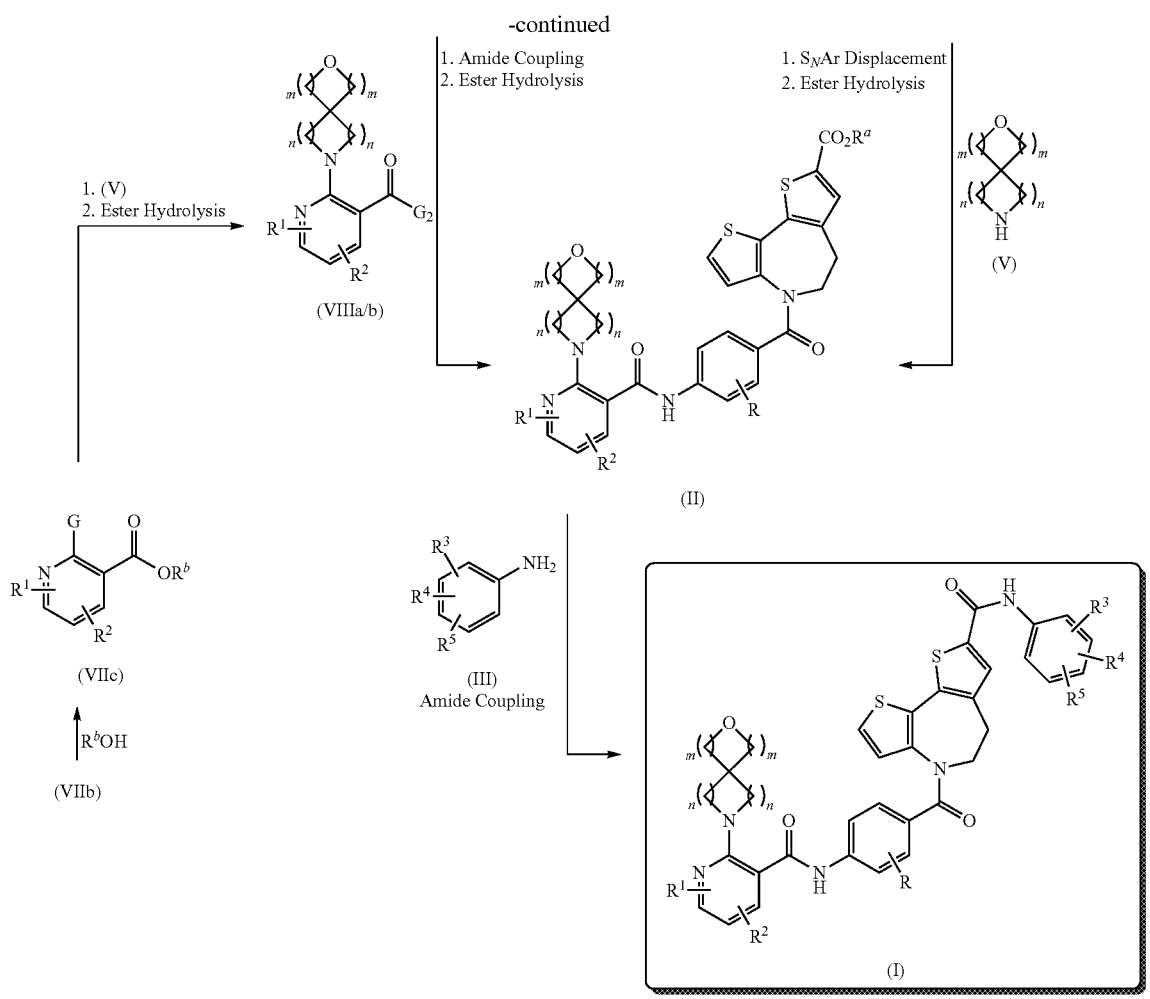

It will be understood by persons skilled in the art that, in some instances, the activated carboxylic acid derivative, such as an acid chloride, may be isolated or, in other cases, may be a transient intermediate that is not isolated, but generated in situ and used directly.

Reagents suitable for the activation of the carboxylate group include carbonyl diimidazole, 1-chloro-N,N,2-trimethylprop-1-en-1-amine and a wide selection of peptide coupling agents such as benzotriazol-1-yloxytripyrrolidinophosphonium hexafluorophosphate (PyBOP®) and the like. Such reactions are conveniently carried out in an, aprotic solvent, such as DCM at or below ambient temperature, such as RT. The compounds of formula (I) are revealed, in those instances wherein one or more protective groups have been employed, by appropriate deprotection steps.

Compounds of formula (II) are readily prepared by $S_NAr$ displacement between a reactive, electrophilic pyridine, of formula (IV), or a suitably protected derivative thereof, and an amine of formula (V), wherein R, $R^1$ and $R^2$ are as defined above for compounds of formula (I), $R^a$ is a lower alkyl group, such as methyl, ethyl, or tert-butyl and G is a suitable nucleofuge such as a halogen, for example a chlorine atom. The compounds of formula (II) are obtained following subsequent hydrolysis of the ester —$CO_2R^a$ to the free acid.

Conditions suitable for the displacement step are reaction in polar, aprotic solvents such as DMF or NMP, in the presence of a non-nucleophilic base, for example triethylamine and at elevated temperatures such as 100-150° C. Lower alkyl esters such as methyl and ethyl esters may be conveniently hydrolysed by exposure to a suitable inorganic base, for example lithium hydroxide, in an aqueous mixture of aprotic and protic solvents, such THF, methanol and water. Such reactions may be subject to gentle heating, for example to 30-50° C. Alternatively esters selected for their lability to acidolysis such as tert-butyl esters are conveniently hydrolysed by treatment with a strong mineral acid or strong organic acid, such as neat TFA, typically at, or near, ambient temperature.

Intermediates represented by compounds of formula (IV) may be derived by acylation of the anilines of formula (VI), with compounds of formula (VIIb), wherein R, $R^a$, $R^1$, and $R^2$ and G are as defined hereinabove and $G_1$ is a readily displaced, electrophilic group, such as a halogen atom, for example chlorine. Conditions routinely employed for these transformations are reaction in an aprotic solvent such DCM, in the presence of an organic base, for example pyridine at RT. Compounds of formula (VIIb) wherein, for example, $G_1$ is chlorine are conveniently obtained from the corresponding acid (VIIa, $G_1$=OH) by reaction with agents such as thionyl chloride, or oxalyl chloride usually in the presence of a catalytic quantity of DMF or by treatment with reagents such as 1-chloro-N,N,2-trimethylprop-1-en-1-amine in an inert solvent, such as DCM, usually at ambient temperatures. If so desired the acylation step may be carried out directly between an amine of formula (VI) and an acid of formula (VIIa), under the influence of suitable peptide coupling agents, of which an extensive selection is available in the art The compound intermediates of formula (VI), wherein R and $R^a$ are as defined above, are readily prepared by the chemoselective reduction of the corresponding nitroarenes of formula (IX). A method commonly employed for such conversions is a dissolving metal reduction. A metal frequently employed is iron, usually in the form of a powder and in the presence of a proton source such as an ammonium salt, for example ammonium chloride. The reduction is typically undertaken in an aqueous mixture of water miscible solvents, for example IPA and water and at elevated temperatures such as 70-80° C. Such reductive transformations may be effected with alternative metals, such as zinc in the form of a powder and are typically conducted in an aqueous mixture of water miscible solvents, for example in methanol, THF and water, at ambient temperature.

Alternatively it is standard practice to effect such transformations by hydrogenation over a suitable noble metal catalyst. An exemplary procedure is reduction with hydrogen at ambient temperature and pressure over palladium on carbon, or the like, in a solvent such as THF or ethanol or mixtures thereof. It may be advantageous to conduct the process in the presence of an acid, for example hydrochloric acid, to prevent the amine product from associating with the catalyst and thereby diminishing its activity.

In some instances it may be advantageous to reorder the synthetic transformations so as to improve the overall efficiency of the process and/or the quality of the materials obtained therefrom. For example, the compounds of formula (II) may also be prepared from the aniline intermediate (VI), as defined herein, with amino-nicotinic acid derivatives of formula (VIII) wherein $R^1$, $R^2$, m and n are as defined above for compounds of formula (I), under conditions suitable for such acylation reactions. A typical procedure is the conversion of the carboxylic acid (VIIIa; $G_2$=OH) into an activated derivative such as an acid halide, most commonly the corresponding acid chloride (VIIIb; $G_2$=Cl), followed by reaction with the amine under basic conditions as described above. Alternatively the acylation may be accomplished under peptide coupling conditions, directly on the acid (VIIIa), for which a wide variety of suitable reagents are available in the art. Subsequent hydrolysis of the alkyl ester by saponification or by acidolysis provides the thienyl carboxylic acids (II) which are transformed into the compounds of the present invention as described above.

The amino-nicotinic acid components of formula (VIIIa) may be formed from nicotinate esters of formula (VIIc), wherein $R^1$ $R^2$, and G are as defined above and $R^b$ is lower alkyl such as an ethyl group, by an $S_NAr$ displacement reaction with the spirocyclic amines of formula (V). The conditions employed for such transformations are typified by those already described hereinabove for the conversion of compounds of formula (IV) into those of formula (II). In a similar manner, the amino-nicotinic acids (VIIIa) are revealed by subsequent hydrolysis of the ester $CO_2R^b$ under either acidic or basic conditions. The nicotinate esters (VIIc) are readily generated by exposure of an aforementioned nicotinyl halide (VIIb) to a lower alcohol, usually at ambient temperature, suitably neat ethanol at RT.

The compounds of the present invention may also be prepared by the application of the general synthetic methodologies, described above, to the aniline substrates of formula (XI) in which the thiophene carboxanilide motif, present in compounds of formula (I) has been previously installed (Scheme 2). For example, the intermediates of formula (XI), wherein R, $R^3$, $R^4$ and $R^5$ are as defined above are transposed into the compounds of the invention, in a single step, by acylation with the amino-nicotinic acid derivatives of formula (VIII). Said interconversion is suitably carried out with an amino-nicotinoyl halide, such as the chloride (VIIIb, $G_2$=Cl) or, if preferred, using the corresponding acid (VIIIa, $G_2$=OH) under appropriate peptide coupling conditions.

In an analogous fashion to the transformations carried out on the thiophene esters of formula (VI) (Scheme 1) the corresponding anilides (XI) may be subjected to an alternative, two stage procedure for the introduction of the amino-nicotinamide domain present in compounds of the invention. In this manner, acylation of the aniline group, present in compounds of formula (XI), with the previously described nicotinic acids of formula (VIIa) or with suitably activated derivatives thereof, such as the acid chlorides (VIIb), affords the nicotinamide products of formula (X). Subjecting these precursors to nucleophilic displacement with the spirocyclic amines of formula (V), in the manner previously described for substrates of formula (IV) (Scheme 1) gives rise to the desired compounds of formula (I).

Scheme 2

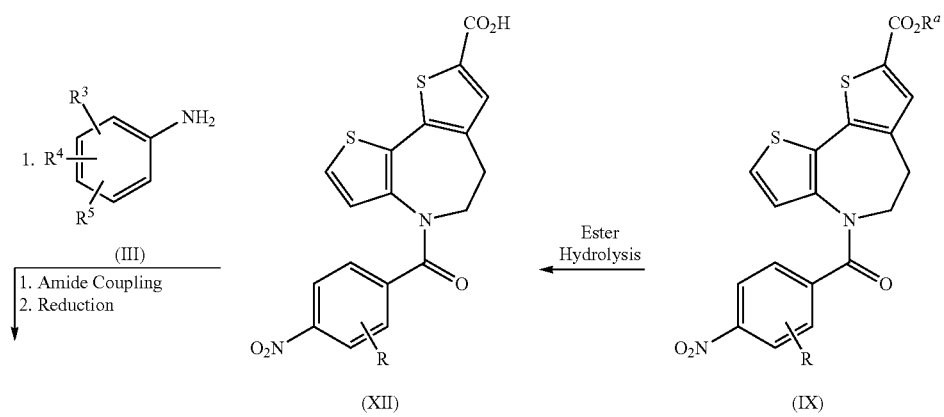

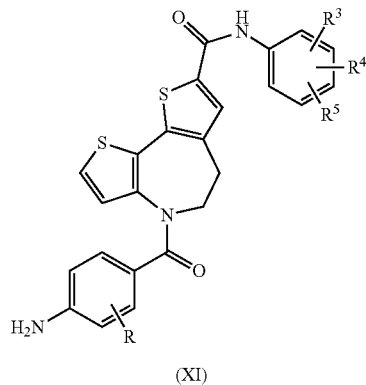
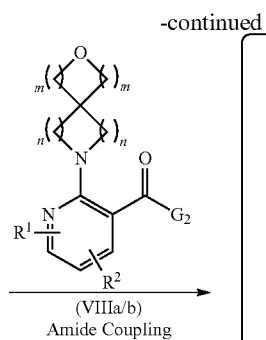
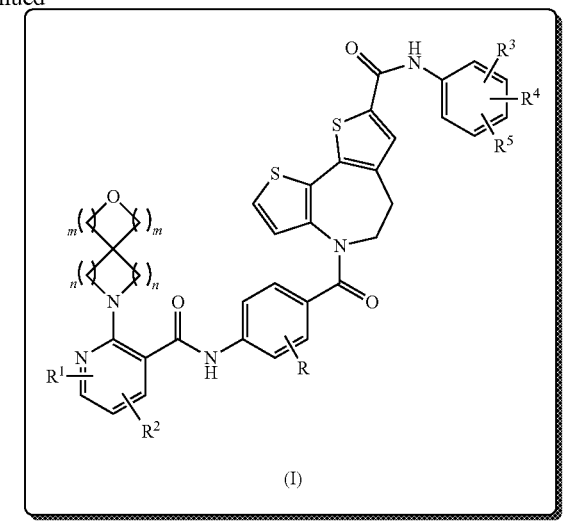
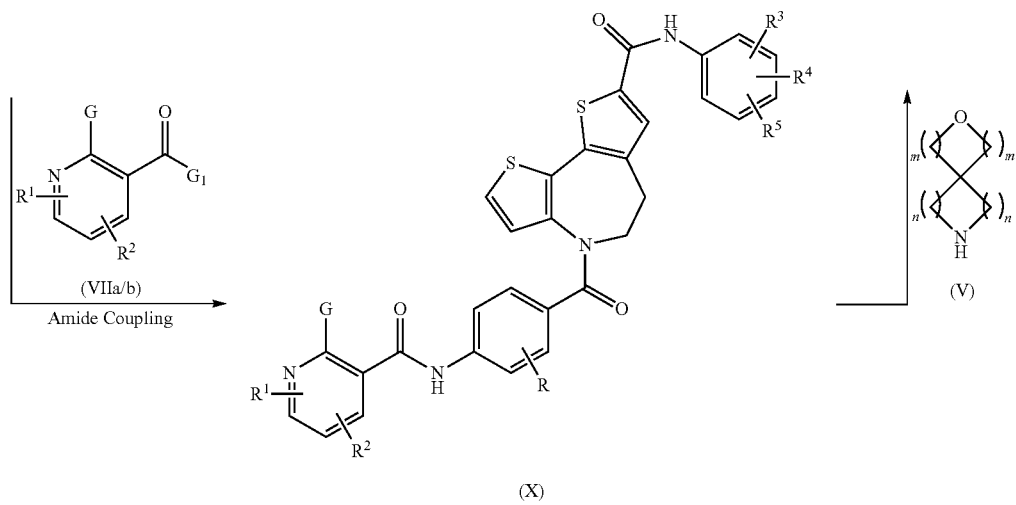

The anilides of formula (XI) are conveniently obtained by an amide coupling between a thiophene carboxylic acid of formula (XII), wherein R is as defined above, and an aniline of formula (III), followed by chemoselective reduction of the nitroarene. Suitable conditions for the amidation step include those described above for the generation of compounds of the invention from the thiophenyl carboxylic acid precursors (II) (Scheme 1). Similarly, the subsequent reduction may be carried out using the methods recited herein, by which the nitroarenes of formula (IX) are converted into the anilino derivatives (VI). The free carboxylic acids, represented by formula (XII), derive from the hydrolysis of the esters of formula (IX), in this instance most suitably by acidolysis, thereby avoiding cleavage of the p-nitrobenzoyl substituent, which is labile under basic conditions. Preferred esters for this interconversion are those readily cleaved by exposure to acid, but otherwise orthogonal with (i.e. stable towards) the preceeding synthetic transformations and include tert-butyl esters ($R^a=^tBu$). It is notable that the esters of formula (IX) constitute pivotal intermediates, common to both of the routes outlined above (Schemes 1 and 2), in which equivalent synthetic transformations are applied in a different sequence to prepare the compounds of the present invention.

The key intermediates of formula (IX) are readily generated by acylation of the heteroaromatic, tricyclic amine (XIII) with a suitable p-nitrobenzoic acid derivative (XIV) (Scheme 3), wherein $R^a$ is lower alkyl as defined above and R is as defined previously for compounds of formula (I).

Scheme 3

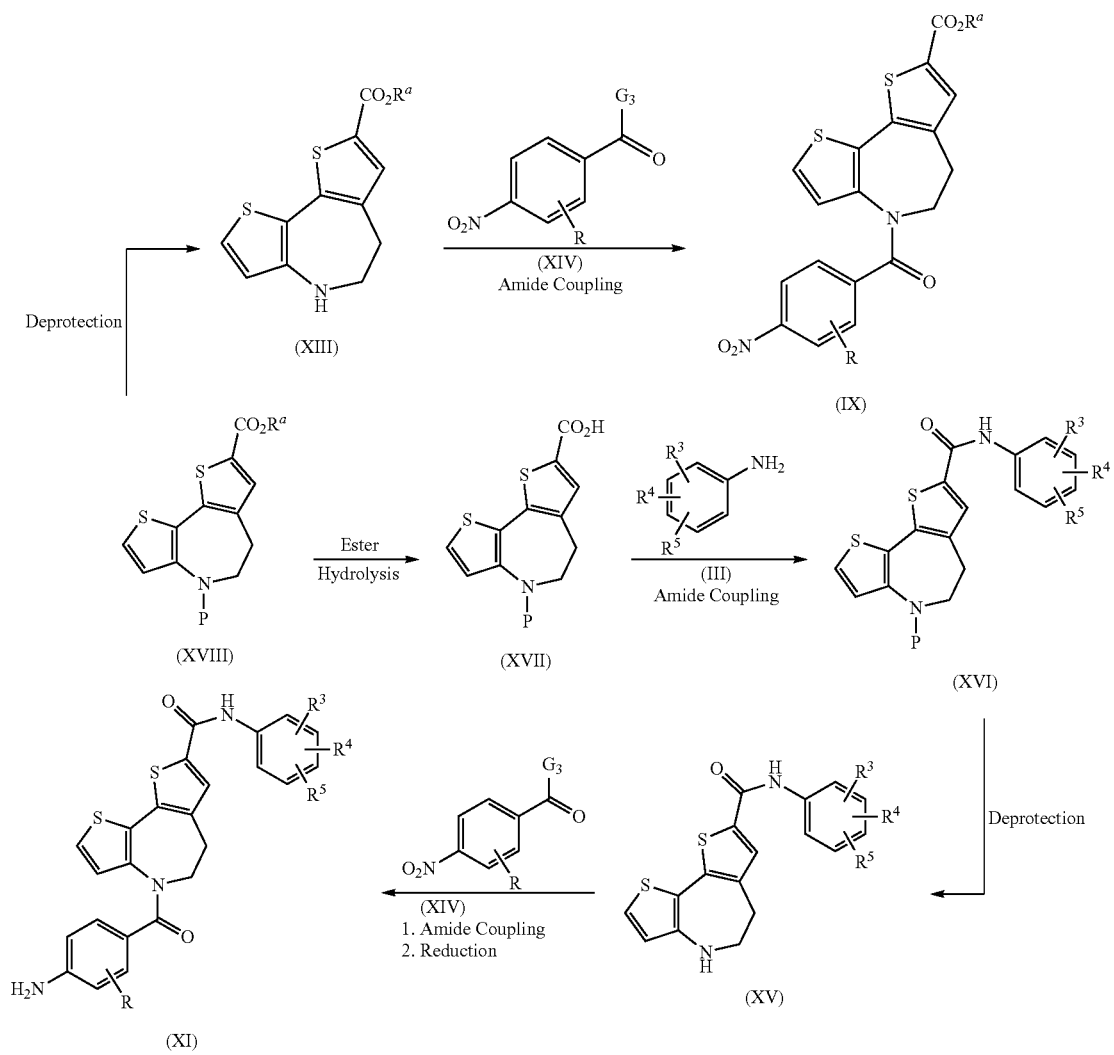

Typically G₃ is an electrophilic group, such as a halogen atom, whereby the reagent (XIV) is a benzoyl halide, most commonly a benzoyl chloride (G₃=Cl). Said acid chlorides may be prepared by numerous methods available in the art. These include treatment of the corresponding acid (G₃=OH) with thionyl chloride or with oxalyl chloride and the like, in an inert, non protic solvent such as toluene, usually in the presence of a catalytic amount of DMF and frequently at elevated temperatures, for example at reflux, to remove volatile by-products of the reaction. It is standard practice to use such resulting electrophilic reagents directly, without purification. Typical conditions for the acylation step are exposure of the amine substrate to the acid chloride in a nonprotic solvent such as acetonitrile and routinely in the presence of a non nucleophilic base, such as pyridine, normally at, or near, ambient temperature.

Alternatively the N-acylation step may be carried out directly on the free acids (G₃=OH) corresponding to compounds of formula (XIV) under conditions commonly employed for the formation of amide bonds. Those skilled in the art will be aware that a wide variety of peptide coupling agents exist for effecting transformations of this kind, such as the uronium based reagents, typified by O-(benzotriazol-1-yl)-N,N,N',N'-tetramethyluronium tetrafluoroborate (TBTU) and the like. It is common practice to conduct the amidation reaction in a non-protic, polar solvent, for example in DMF and in the presence of a non nucleophilic base such as ethyldiisopropylamine (Hunig's base) or an equivalent.

The novel dithieno-azepine (XIII) is derived from a precursor of formula (XVIII) by the removal of the amine protective group (P) employed during its preparation (see Scheme 4 for a suitable synthetic process). A nitrogen protective group, which is fit for this purpose, is a urethane, such as the carboxybenzyl (Cbz) group (P=CO₂CH₂Ph) which may be displaced, for example, by exposure to iodotrimethylsilane (TMSI), suitably in a chlorinated solvent such as DCM and typically in a temperature range of 0-20° C.

Alternatively the N-protective group present in the compounds of formula (XVIII) may be retained until later in the synthetic sequence. Exploiting this strategy allows the esters (CO₂Rᵃ) to be hydrolysed into the corresponding carboxylic acids (XVII) and subsequently transformed into the anilide derivatives of formula (XVI), wherein $R^3$, $R^4$ and $R^5$ are as previously defined. This two step process is a duplicate of that already disclosed above (see Scheme 2) and applied, in the former case, to the N-benzoyl analogues of formula (IX).

The free azepines of formula (XV) are obtained by the removal of the N-protective group, from the aforementioned anilides of formula (XVI), using methodology appropriate to the amine derivative that has been employed. In the case of an N-Cbz group this deprotection step can be achieved by treating said compounds with a solution of TMSI in DCM, or the like, according to the conditions recited above, for the removal of this carbamate group from the compounds of formula (XVIII).

The amines so derived, may then be N-acylated with a p-nitrobenzoic acid derivative (XIV) in the manner already represented and undertaken on the ester analogues (XIII).

may be made, are accessible from the commercially available reagent: 5,6,7,8-tetrahydro-4H-thieno[3,2-b]azepine using the methodologies set out below (Scheme 4). Acylation of the azepine nitrogen with a p-nitrobenzoic acid derivative (XIV), wherein R is as previously defined, by any of the methods already described, provides the amides of formula (XXII). Subsequent oxidation with a reagent, such as potassium permanganate, provides the corresponding azepinones (XXI). Suitable conditions for this transformation are disclosed in the art for the particular case wherein R is hydrogen (Albright and Delos Santos, 1996) and include reaction in an aqueous ketonic solvent mixture, such as acetone and water, usually in the presence of magnesium sulfate, at or near the reflux temperature of the mixture, routinely 50-70° C. The oxidation may also be carried out with a mixture of potassium persulfate and copper sulfate in an aqueous system suitably water and acetonitrile at a temperature in the region of 80° C.

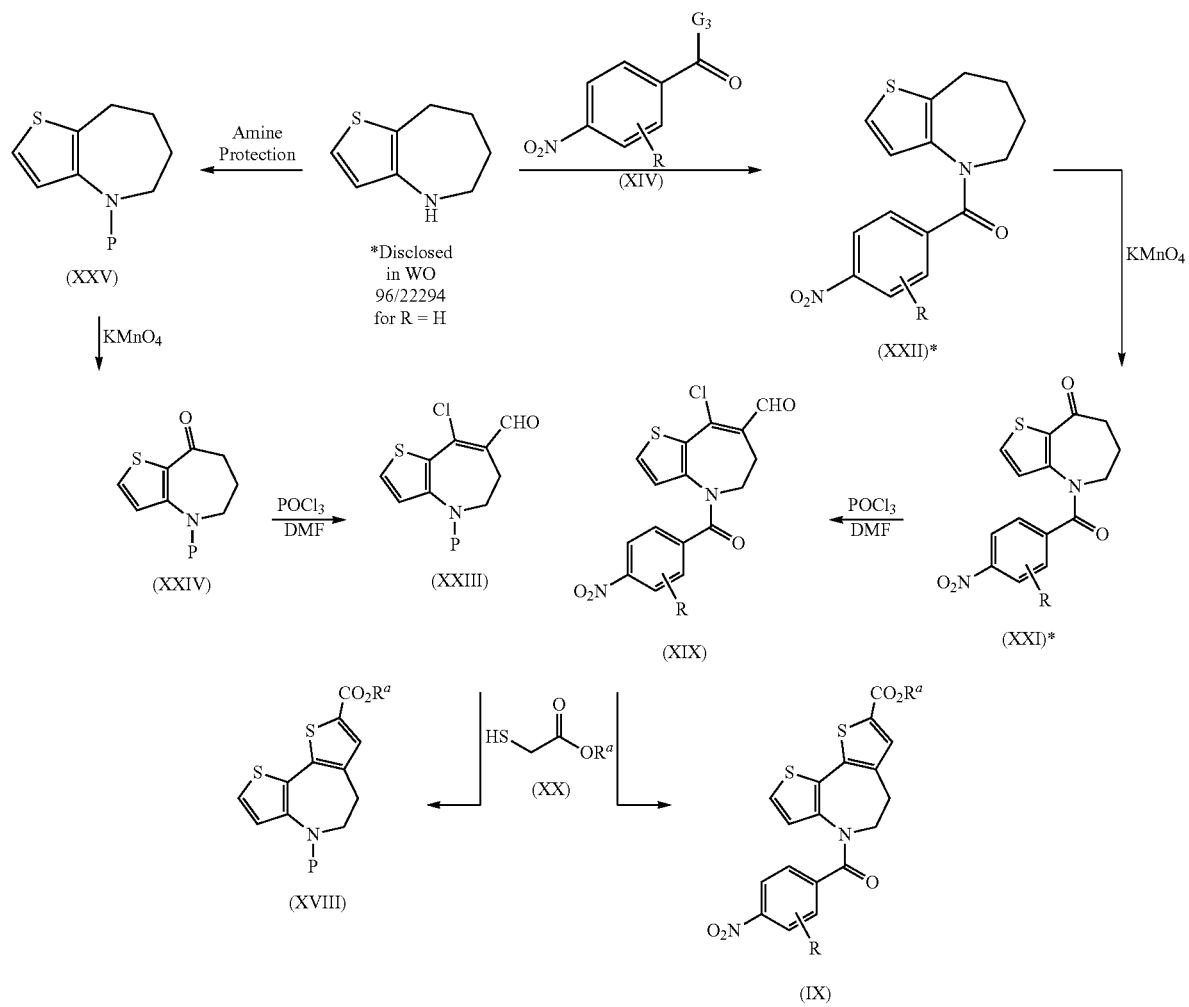

Scheme 4

Reduction of the resulting nitroarenes, following the procedures set out herein for compounds of (IX) (Scheme 1) provides a second, independent route to the anilide intermediates of formula (XI), disclosed herein (Scheme 2).

The key synthetic intermediates of formula (IX) and (XVIII), by which the compounds of the present invention The azepinones (XXI) so obtained are substrates for a two step annulation process in which the first is chloroformylation under Vilsmeier-Haack conditions. Conversion into the 3-chloro-enealdehydes of formula (XIX) proceeds under the agency of a Vilsmeier reagent, such as that generated in situ by mixing phosphoryl trichloride with neat DMF, usually at or near 0° C., followed by addition of the azepinone derivatives (XXI) and gentle warming, typically to 50° C. Condensation of the formylation products (XIX) with an 2-mercaptoacetate of formula (XX), wherein $R^a$ is lower alkyl as defined previously, takes place under basic conditions, suitably in a mixture of pyridine and triethylamine, at elevated temperatures, most commonly 70-120° C. The resulting dihydro-dithienoazepine-carboxylic acid derivatives of formula (IX), constitute a series of versatile intermediates for preparing compounds of formula (I) as recited in detail hereinabove (Schemes 1 and 2).

Alternatively the sequence of reactions documented above for the three step conversion of the azepinyl-benzamides (XXII) into the intermediates of formula (IX) can be applied to an appropriately derivatised thienoazepine of formula (XXV), wherein P is a suitable amine protective group (Scheme 4). A requirement for the successful implementation of this strategy is that the said protective group is stable to the successive oxidising, acidic and basic conditions used to affect the homologation procedure. A nitrogen protective group with the necessary inertness is the carboxybenzyl (Cbz) group, which can be installed by reaction of the azepine starting material with benzyl chloroformate by procedures that are widely practised in the art.

Subjecting the azepine carbamate (XXV) to the permanganate oxidation conditions, as applied to compounds of formula (XXII), provides the corresponding azepinone derivative (XXIV). This ketone intermediate may be modified under the same Vilsmeier-Haack conditions, performed on compounds of formula (XXI), to generate the analogous chloroformylated product (XXIII). Repetition of the condensation step on this substrate, as previously employed on compounds of formula (XIX), delivers the N-protected, dihydro-dithienoazepine-carboxylate esters of formula (XVIII); the utility of which, in the preparation of compounds of formula (I), have been disclosed herein (Scheme 3).

A subset of the 2-aminonicotinic acid intermediates (VIII) disclosed above (Schemes 1 and 2), are represented by compounds of formula (VIIIc) (Scheme 5), which may be obtained from palladium catalysed, carbon-carbon bond forming reactions on a bromo-nicotinate substrate of formula (XXVII), wherein m and n are as defined for compounds of formula (I) and $R^c$ is lower alkyl, The radical $R^{2a}$, transferred in the said process, is any substituent selected from the group $R^2$, as defined previously, for which an appropriate reagent is either available from commercial sources or which may be prepared by established methods. Those skilled in the art will appreciate that an extensive methodology exists for conducting transformation of this type and a wide range of suitable conditions may be used.

Scheme 5

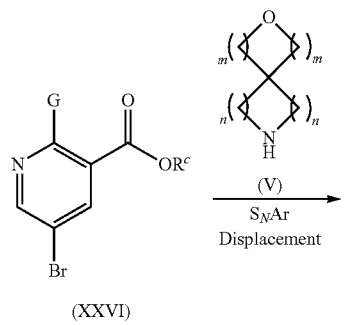

(XXVI)

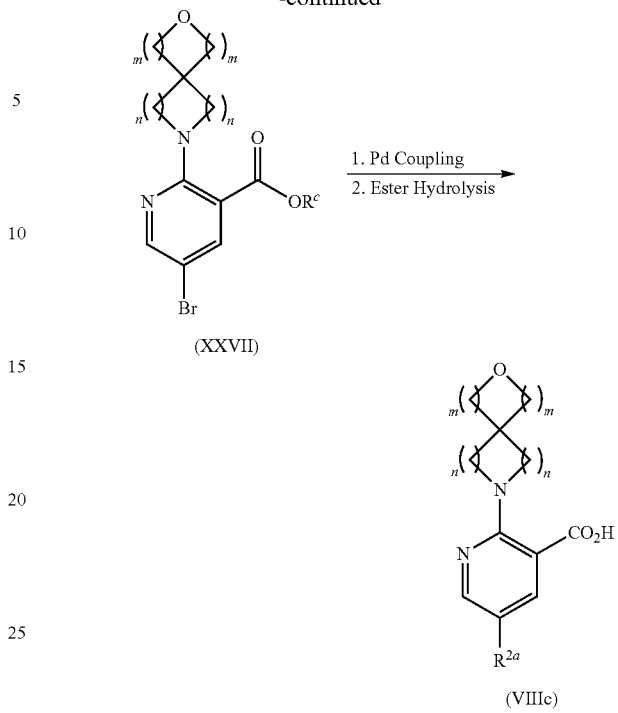

For example, the aryl bromide of formula (XXVII) may be subjected to a Suzuki cross-coupling with a boronic acid of formula $R^{2a}B(OH)_2$ or similar, using a palladium catalyst. The choice of suitable catalysts, includes a wide variety of coordinated ligand complexes, such as [1,1'-bis(diphenylphosphino)ferrocene]dichloropalladium(II) and the like. It is common for such reactions to be run in solvents such as THF, 1,4-dioxane, ethanol or toluene, usually in the presence of water and a base, for example potassium carbonate, cesium carbonate or tripotassium phosphate and for them to be heated, typically in the region 80-100° C. The desired nicotinic acids of formula (VIIIc) are revealed following hydrolysis of the resulting esters under either acidic or basic conditions by standard procedures, according to preference.

The bromo-nicotinates of formula (XXVII) may also be used to incorporate substituents into the pyridine nucleus in which the newly created bond is to an sp hybridised carbon, i.e. wherein $R^{2a}$ is an acetylenic group. A versatile and well established methodology for such a process is the Sonogoshira coupling, whereby the reaction is performed with a terminal alkyne, typically in the presence of a palladium catalyst, a copper(I) co-catalyst and an amine base. A suitable aceylenic substrate, is ethynyltriisopropylsilane, from which the silicon protective group may be removed by proto-desilylation following its installation. Catalyst combinations such as tetrakis(triphenylphosphine)palladium(0) and copper(I) iodide are routinely employed. It is common practice to perform the coupling step at elevated temperatures such as 50-100° C., in solvents such as DMSO and DMF and in the presence of an inorganic base, such as cesium (or potassium) carbonate, or alternatively an organic base, for example triethylamine.

A review of methodologies for the preparation of amides is covered in: 'Amide bond formation and peptide coupling' Montalbetti, C. A. G. N. and Falque, V. Tetrahedron, 2005, 61, 10827-10852. Protective groups and the means for their removal are described in "Protective Groups in Organic Synthesis", by Theodora W. Greene and Peter G. M. Wuts, published by John Wiley & Sons Inc; 4th Rev Ed., 2006, ISBN-10: 0471697540.

Novel intermediates as described herein include compounds of formula (II), (IV), (VI), (IX), (X), (XI), (XII) (XIII), (XV), (XVI), (XVIII) (XVII) (XIX) and (XXIII) form a further aspect of the invention, as do salts thereof (such as pharmaceutically acceptable salts).

Compounds of the Invention are Useful as Pharmaceuticals.

In an embodiment there is provided a pharmaceutical composition comprising a compound of the invention optionally in combination with one or more pharmaceutically acceptable diluents or carriers.

Suitably compounds of the invention are administered topically to the lung or nose, particularly, topically to the lung. Thus, in an embodiment there is provided a pharmaceutical composition comprising a compound of the invention optionally in combination with one or more topically acceptable diluents or carriers.

Suitably compositions for pulmonary or intranasal administration include powders, liquid solutions, liquid suspensions, nasal drops comprising solutions or suspensions or pressurised or non-pressurised aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). The compositions may also conveniently be administered in multiple unit dosage form.

Topical administration to the nose or lung may be achieved by use of a non-pressurised formulation such as an aqueous solution or suspension. Such formulations may be administered by means of a nebuliser e.g. one that can be hand-held and portable or for home or hospital use (i.e. non-portable). An example device is a RESPIMAT inhaler. The formulation may comprise excipients such as water, buffers, tonicity adjusting agents, pH adjusting agents, viscosity modifiers, surfactants and co-solvents (such as ethanol). Suspension liquid and aerosol formulations (whether pressurised or unpressurised) will typically contain the compound of the invention in finely divided form, for example with a $D_{50}$ of 0.5-10 µm e.g. around 1-5 µm.

Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the Do value, respectively.

According to one specific aspect of the invention there is provided a pharmaceutical composition comprising a compound of the invention in particulate form suspended in an aqueous medium. The aqueous medium typically comprises water and one or more excipients selected from buffers, tonicity adjusting agents, pH adjusting agents, viscosity modifiers and surfactants.

Topical administration to the nose or lung may also be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a dry-powder formulation. A dry powder formulation will contain the compound of the disclosure in finely divided form, typically with an MMD of 1-10 µm or a $D_{50}$ of 0.5-10 µm e.g. around 1-5 µm. Powders of the compound of the invention in finely divided form may be prepared by a micronisation process or similar size reduction process. Micronisation may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. an MMD of 50 µm or more, e.g. 100 µm or more or a $D_{50}$ of 40-150 µm. As used herein, the term "lactose" refers to a lactose-containing component, including a-lactose monohydrate, 1-lactose monohydrate, a-lactose anhydrous, 1-lactose anhydrous and amorphous lactose. Lactose components may be processed by micronisation, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of a-lactose monohydrate, a-lactose anhydrous and amorphous lactose. Preferably, the lactose is a-lactose monohydrate.

Dry powder formulations may also contain other excipients such as sodium stearate, calcium stearate or magnesium stearate.

A dry powder formulation is typically delivered using a dry powder inhaler (DPI) device. Example dry powder delivery systems include SPINHALER, DISKHALER, TURBOHALER, DISKUS, SKYEHALER, ACCUHALER and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

Compounds of the invention are useful in the treatment of RSV infection and for the prevention or treatment of disease associated with RSV infection.

In an aspect of the invention there is provided use of a compound of the invention in the manufacture of a medicament for the treatment of RSV infection and for the prevention or treatment of disease associated with RSV infection.

In another aspect of the invention there is provided a method of treatment of a subject infected with RSV which comprises administering to said subject an effective amount of a compound of the invention.

In another aspect of the invention there is provided a method of prevention or treatment of disease associated with RSV infection in a subject which comprises administering to said subject an effective amount of a compound of the invention.

Compounds of the invention may be used in a prophylactic setting by administering them prior to infection.

In one embodiment the RSV infection is RSV A strain infection (e.g. with an RSV A2 strain). In another embodiment the RSV infection is RSV B strain infection (e.g. with RSV B Washington strain).

Subjects include human and animal subjects, especially human subjects.

Compounds of the invention are especially useful for the treatment of RSV infection and for the prevention or treatment of disease associated with RSV infection in at risk subjects. At risk subjects include premature infants, children with congenital defects of the lung or heart, immunocompromised subjects (e.g. those suffering from HIV infection), elderly subjects and subjects suffering from a chronic health condition affecting the heart or lung (e.g. congestive heart failure or chronic obstructive pulmonary disease).

Compounds of the invention may be administered in combination with a second or further active ingredient. Compounds of the invention may be co-formulated with a second or further active ingredient or the second or further active ingredient may be formulated to be administered separately by the same or a different route. According to an aspect of the invention there is provided a kit of parts comprising (a) a pharmaceutical composition comprising a compound of the invention optionally in combination with one or more diluents or carriers; (b) a pharmaceutical composition comprising a second active ingredient optionally in combination with one or more diluents or carriers; (c) optionally one or more further pharmaceutical compositions each comprising a third or further active ingredient optionally in combination with one or more diluents or carriers; and (d) instructions for the administration of the pharmaceutical compositions to a subject in need thereof. The subject in need thereof may suffer from or be susceptible to RSV infection.

Second or further active ingredients include active ingredients suitable for the treatment or prevention of RSV infection or disease associated with RSV infection or conditions co-morbid with RSV infection.

Second or further active ingredients may, for example, be selected from anti-viral agents (such as other anti-RSV agents) including F protein inhibitors (including anti-F-protein antibodies, such as palivizumab), RNA polymerase inhibitors and ribavirin and anti-inflammatory agents.

Compounds of the invention may be administered at a suitable interval, for example once per day, twice per day, three times per day or four times per day.

A suitable dose amount for a human of average weight (50-70 kg) is expected to be around 50 µg to 10 mg/day e.g. 500 µg to 5 mg/day although the precise dose to be administered may be determined by a skilled person.

Compounds of the invention are expected to have one or more of the following favourable attributes:
a) potent inhibition of cytopathic effect and/or virus replication and/or F-protein expression in humans (or an animal model, or an in vitro system) caused by RSV A strains, such as the A2 strain;
b) potent inhibition of cytopathic effect and/or virus replication and/or F-protein expression in humans (or an animal model, or an in vitro system) caused by RSV B strains;
c) long duration of action in lungs, preferably consistent with once daily dosing;
d) acceptable safety profile, especially following topical administration to the lung or nose.

EXPERIMENTAL SECTION

Abbreviations used herein are defined below (Table 1). Any abbreviations not defined are intended to convey their generally accepted meaning.

Table 1: Abbreviations

AcOH glacial acetic acid
ALI air liquid interface
aq aqueous
BALF bronchoalveolar lavage fluid
BEAS2B SV40-immortalised human bronchial epithelial cell line
Boc tert-butyloxycarbonyl
br broad
BSA bovine serum albumin
CatCart® catalytic cartridge
Cbz carboxybenzyl
$CC_{50}$ 50% cell cytotoxicity concentration
CDI 1,1-carbonyl-diimidazole
conc concentrated
CPE cytopathic effect
d doublet
DAB 3,3'-diaminobenzidine
DCM dichloromethane
DIPEA N,N-diisopropylethylamine
DMEM Dulbecco's Modified Eagle Medium
DMF N,N-dimethylformamide
DMSO dimethyl sulfoxide
DSS dextran sodium sulphate
($ES^+$) electrospray ionization, positive mode
Et ethyl
EtOAc ethyl acetate
FBS foetal bovine serum
HATU 1-[bis(dimethylamino)methylene]-1H-1,2,3-triazolo[4,5-b]pyridinium 3-oxid hexafluorophosphate
HEp2 human laryngeal epithelioma cell line 2
HPLC high performance liquid chromatography (reverse phase)
hr hour(s)
HRP horse radish peroxidase
$IC_{50}$ 50% inhibitory concentration
$IC_{75}$ 75% inhibitory concentration
$IC_{90}$ 90% inhibitory concentration
IgG immunoglobin G
m multiplet
$(M+H)^+$ protonated molecular ion
Me methyl
MeCN acetonitrile
MeOH methanol
MHz megahertz MMD mass median diameter
MOI multiplicity of infection
min minute(s)
m/z mass-to-charge ratio
NMP N-methylpyrrolidine
NMR nuclear magnetic resonance (spectroscopy)
nt not tested
OD optical density
PBS phosphate buffered saline
PCR polymerase chain reaction
Pd(dppf)Cl$_2$ [1,1'-bis(diphenylphosphino)ferrocene]dichloropalladium(II)
Pen Srep Penicillin-Streptomycin
PFU plaque forming unit
Ph phenyl
prep HPLC preparative high performance liquid chromatography
PG protective group
Ph phenyl
q quartet
RT room temperature
RP HPLC reverse phase high performance liquid chromatography
RPMI Roswell Park Memorial Institute medium
RSV respiratory syncytial virus
s singlet
sat saturated
SCX solid supported cation exchange (resin)
SDS sodium dodecyl sulphate
S$_N$Ar nucleophilic aromatic substitution
t triplet
THF tetrahydrofuran
THP tetrahydropyran
TLC thin layer chromatography
TMB 3,3',5,5'-tetramethylbenzidine
TMSI iodotrimethylsilane
Tos p-toluenesulfonyl
vol volume(s)
WB washing buffer General Procedures All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under pressure in a gas autoclave (bomb).

Column chromatography was performed on pre-packed silica (230-400 mesh, 40-63 µm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M NH$_3$ in MeOH.

Preparative Reverse Phase High Performance Liquid Chromatography

Method 1: Waters X-Select CSH column C18, 5 µm (19×50 mm), flow rate 26.5 mL min$^{-1}$ eluting with a H$_2$O-MeCN gradient containing 0.1% v/v formic acid over 10 min using UV detection across all wavelngths with PDA as well as a QDa Mass Detector. At-Column Dilution pump gives 1.5 mL min$^{-1}$ MeCN over the entire method, which is included in the following MeCN percentages. Gradient information: 0.0-0.2 min, 20% MeCN; 0.2-5.5 min, ramped from 20% MeCN to 50% MeCN; 5.5-5.6 min, ramped from 50% MeCN to 95% MeCN; 5.6-6.5 min, held at 95% MeCN.

Method 2: Waters X-Select CSH column C18, 5 µm (19×50 mm), flow rate 26.5 mL min$^{-1}$ eluting with a H$_2$O-MeCN gradient containing 0.1% v/v formic acid over 10 min using UV detection across all wavelngths with PDA as well as a QDa Mass Detector. At-Column Dilution pump gives 1.5 mL min$^{-1}$ MeCN over the entire method, which is included in the following MeCN percentages. Gradient information: 0.0-0.2 min, 25% MeCN; 0.2-5.5 min, ramped from 25% MeCN to 55% MeCN; 5.5-5.6 min, ramped from 55% MeCN to 95% MeCN; 5.6-6.5 min, held at 95% MeCN.

Method 3: Waters X-Select CSH column C18, 5 µm (19×50 mm), flow rate 26.5 mL min$^{-1}$ eluting with a H$_2$O-MeCN gradient containing 0.1% v/v formic acid over 10 min using UV detection across all wavelngths with PDA as well as a QDa Mass Detector. At-Column Dilution pump gives 1.5 mL min$^{-1}$ MeCN over the entire method, which is included in the following MeCN percentages. Gradient information: 0.0-0.2 min, 35% MeCN; 0.2-5.5 min, ramped from 35% MeCN to 65% MeCN; 5.5-5.6 min, ramped from 65% MeCN to 95% MeCN; 5.6-6.5 min, held at 95% MeCN.

Method 4: Waters X-Select CSH column C18, 5 µm (19×50 mm), flow rate 26.5 mL min$^{-1}$ eluting with a H$_2$O-MeCN gradient containing 0.1% v/v formic acid over 10 min using UV detection at 254 nm. At-Column Dilution pump gives 1.5 mL min$^{-1}$ MeCN over the entire method, which is not included in the following MeCN percentages. Gradient information: 0.0-0.1 min, 20% MeCN; 0.1-7.5 min, ramped from 20% MeCN to 50% MeCN; 7.5-8.5 min, ramped from 50% MeCN to 95% MeCN; 8.5-8.6 min, ramped from 95% MeCN to 20% MeCN; 8.6-10.0 min, held at 20% MeCN.

Method 5: Waters X-Select CSH column C18, 5 µm (19×50 mm), flow rate 26.5 mL min$^{-1}$ eluting with a H$_2$O-MeCN gradient containing 0.1% v/v formic acid over 10 min using UV detection at 254 nm. At-Column Dilution pump gives 1.5 mL min$^{-1}$ MeCN over the entire method, which is not included in the following MeCN percentages. Gradient information: 0.0-0.1 min, 15% MeCN; 0.1-7.5 min, ramped from 15% MeCN to 35% MeCN; 7.5-8.5 min, ramped from 35% MeCN to 95% MeCN; 8.5-8.6 min, ramped from 95% MeCN to 15% MeCN; 8.6-10.0 min, held at 15% MeCN.

Method 6: Waters X-Bridge BEH column C18, 5 µm (19×50 mm), flow rate 28 mL min$^{-1}$ eluting with a 10 mM ammonium bicarbonate-MeCN gradient over 6.5 min using UV detection at 215 and 254 nm as well as a ZQ Mass Spectrometer. Gradient information: 0.0-0.2 min, 35% MeCN; 0.2-5.5 min, ramped from 35% MeCN to 65% MeCN; 5.5-5.6 min, ramped from 65% MeCN to 95% MeCN; 5.6-6.5 min, held at 95% MeCN.

Analytical Methods

Reverse Phase HPLC Conditions for the LCMS Analytical Methods

Methods 1a and 1b: Waters Xselect CSH C18 XP column, 2.5 µm (4.6×30 mm) at 40° C.; flow rate 2.5-4.5 mL min$^{-1}$ eluted with a H$_2$O-MeCN gradient containing either 0.1% v/v formic acid (Method 1a) or 10 mM NH$_4$HCO$_3$ in water (Method 1b) over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01 3.50 min, held at 5% H$_2$O-95% MeCN; 3.50-3.60 min, returned to 95% H₂O-5% MeCN, flow rate reduced to 3.50 mL min⁻¹; 3.60-3.90 min, held at 95% H₂O-5% MeCN; 3.90-4.00 min, held at 95% H₂O-5% MeCN, flow rate reduced to 2.5 mL min⁻¹.

¹H NMR Spectroscopy

¹H NMR spectra were acquired on a Bruker Avance III spectrometer at 400 MHz using residual undeuterated solvent as reference and unless specified otherwise were run in DMSO-d₆.

Preparation of Intermediates

Known synthetic intermediates were procured from commercial sources or were obtained using published literature procedures. Additional intermediates were prepared by the representative synthetic processes described herein.

2-Chloronicotinoyl Chloride

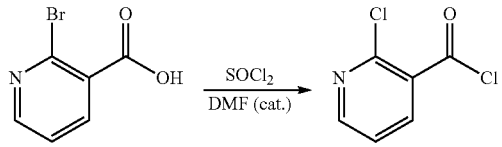

Thionyl chloride (70 mL) was added in one portion to neat 2-bromonicotinic acid (10.0 g, 49.5 mmol) at RT, followed by 2-3 drops of DMF and the mixture was heated at reflux for 4 hr. The reaction was cooled to RT and the excess thionyl chloride was removed by evaporation in vacuo. The residue was recrystallised from isohexane to afford the title compound as a light yellow solid (7.81 g, 90% pure by ¹H-NMR, 81% yield). This material was used in subsequent steps without additional purification.

Ethyl 2-chloro-5-methylnicotinate

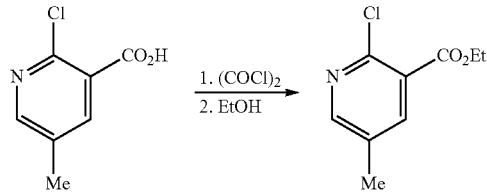 [SMILES: Cc1cnc(Cl)c(C(=O)O)c1 ; CCOC(=O)c1cc(C)cnc1Cl]

To a solution of 2-chloro-5-methylnicotinic acid (3.90 g, 22.7 mmol) in DCM (100 mL) was added oxalyl chloride (9.95 mL, 114 mmol) followed by 1 drop of DMF. The resulting mixture was stirred at RT for 30 min and evaporated in vacuo. The residue thus obtained was taken up into EtOH (66 mL), stirred for a further 2 hr and then evaporated in vacuo. The crude product obtained was purified by flash column chromatography (SiO₂, 120 g, 0-50% DCM in isohexane, gradient elution) to afford the title compound as a colourless oil (3.71 g, 82% yield); ¹H NMR δ: 1.32 (3H, t), 2.34 (3H, s), 4.34 (2H, q), 8.06-8.07 (1H, m), 8.41-8.43 (1H, m). [See also: Yamamoto S. et al., *Bioorg. Med. Chem.* 2012, 20, 422-434.]

Ethyl 5-methyl-2-(7-oxa-2-azaspiro[3.5]nonan-2-yl) nicotinate

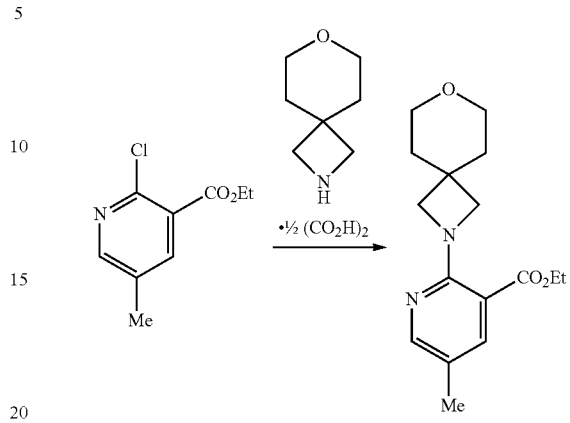

A mixture of ethyl 2-chloro-5-methylnicotinate (3.70 g, 18.5 mmol), 7-oxa-2-azaspiro[3.5]nonane hemioxalate (9.57 g, 55.6 mmol) and DIPEA (19.4 mL, 111 mmol) in NMP (50 mL) was heated at 150° C. for 2 hr. After cooling to RT the crude mixture was poured into water (200 mL) and extracted with EtOAc (3×200 mL). The combined organic extracts were washed with brine (2×100 mL), and then dried and evaporated in vacuo to afford the title compound (4.81 g, 88% yield); R$^t$ 1.32 min (Method 1a); m/z 291 (M+H)+ (ES⁺); ¹H NMR δ: 1.29 (3H, t), 1.67 (4H, br t), 2.18 (3H, s), 3.52 (4H, br t), 3.67 (4H, s), 4.25 (2H, q), 7.74 (1H, apparent dd), 8.12 (1H, apparent dd).

5-Methyl-2-(7-oxa-2-azaspiro[3.5]nonan-2-yl)nicotinic Acid

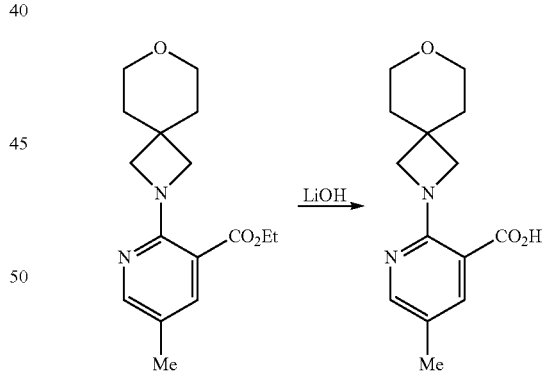

A mixture of ethyl 5-methyl-2-(7-oxa-2-azaspiro[3.5] nonan-2-yl)nicotinate (4.1 g, 14 mmol) and lithium hydroxide (0.50 g, 21 mmol) in THF:water (4:1, 50 mL) was heated at 50° C. for 18 hr and then evaporated in vacuo. The residue thus obtained was acidified to pH 4 by the addition of 1 M hydrochloric acid and the resulting mixture extracted with EtOAc (10×250 mL). The combined organic extracts were evaporated in vacuo to afford the title compound as a crystalline solid (3.4 g, 92% yield); R$^t$ 0.42 min (Method 1a); m/z 263 (M+H)⁺ (ES⁺); ¹H NMR δ: 1.67 (4H, br t), 2.17 (3H, s), 3.52 (4H, br t), 3.69 (4H, s), 7.74 (1H, apparent dd), 8.09 (1H, apparent dd), 12.69 (1H, br).

Methyl 5-bromo-2-(7-oxa-2-azaspiro[3.5]nonan-2-yl)nicotinate

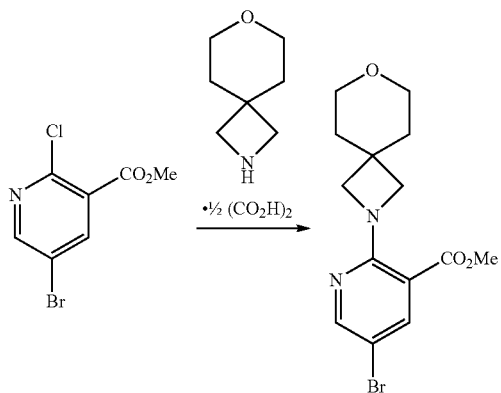

To a solution of methyl 5-bromo-2-chloronicotinate (5.75 g, 23.0 mmol) and 7-oxa-2-azaspiro[3.5]nonane hemi oxalate (5.98 g, 27.5 mmol) in NMP (55 mL) was added Et₃N (9.60 mL, 68.9 mmol). The reaction mixture was heated to 120° C. for 1 hr and was then cooled to RT and diluted with water (250 mL) and EtOAc (200 mL). The aq layer was separated and was extracted with EtOAc (200 mL). The combined organic layers were washed with water (3×300 mL) and then dried and evaporated in vacuo to give the title compound as a brown solid (7.22 g, 92% yield); $R^t$ 2.15 min (Method 1a); m/z 340/342 (M+H)⁺ (ES⁺); ¹H NMR δ: 1.68 (4H, br t), 3.52 (4H, br t), 3.72 (4H, s), 3.81 (3H, s), 8.01 (1H, d), 8.35 (1H, d).

Methyl 2-(7-oxa-2-azaspiro[3.5]nonan-2-yl)-5-((triisopropylsilyl)ethynyl)nicotinate

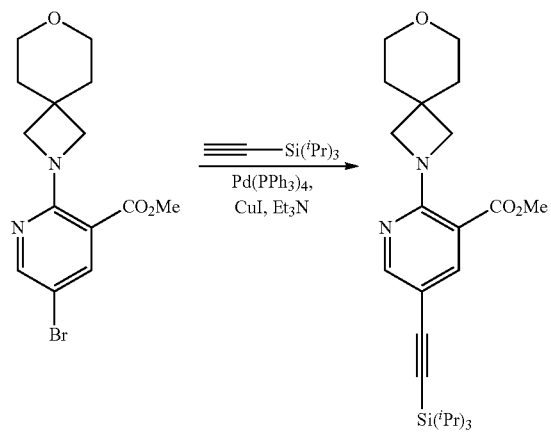

To a solution of methyl 5-bromo-2-(7-oxa-2-azaspiro[3.5]nonan-2-yl)nicotinate (100 mg, 0.29 mmol) in DMF (1.0 mL), which had been degassed with nitrogen for 10 min, was added tetrakis(triphenylphosphine)palladium(0) (35 mg, 0.030 mmol), copper(I) iodide (11 mg, 0.060 mmol), triethylamine (84 μL, 0.60 mmol) and ethynyltriisopropylsilane (369 μL, 0.30 mmol). The resulting mixture was flushed with nitrogen for 5 min, heated at 50° C. for 4 hr and was then cooled to RT and partitioned between water (10 mL) and EtOAc (25 mL). The organic layer was separated and retained and the aq phase was extracted with EtOAc (25 mL). The combined organic extracts were washed with water (10 mL) and with brine (10 mL), and then dried and evaporated in vacuo. The residue thus obtained was purified by flash column chromatography (SiO₂, 12 g, 0-50% EtOAc in isohexane, gradient elution) to afford the title compound as a brown oil (117 mg, 88% yield); $R^t$ 3.35 min (Method 1a); m/z 443 (M+H)⁺ (ES⁺); ¹H NMR δ: 1.08 (21H, overlapping d and m), 1.68 (4H, br t), 3.52 (4H, br t), 3.77 (4H, s), 3.80 (3H, s), 7.89 (1H, d), 8.34 (1H, d).

2-(7-oxa-2-azaspiro[3.5]nonan-2-yl)-5-((triisopropylsilyl)ethynyl)nicotinic Acid

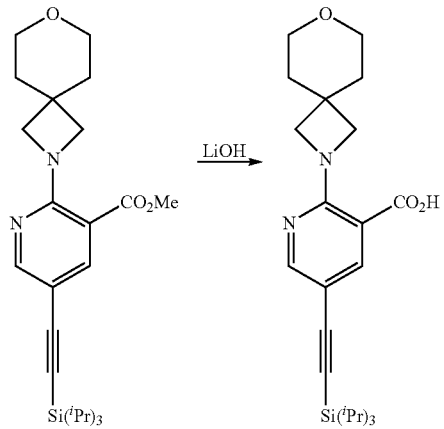

To a solution of methyl 2-(7-oxa-2-azaspiro[3.5]nonan-2-yl)-5-((triisopropylsilyl)ethynyl) nicotinate (148 mg, 0.33 mmol) in a mixture of THF, MeOH and water (1:1:1, 2.1 mL) was added lithium hydroxide (9.6 mg, 0.40 mmol). The reaction mixture was heated to 50° C. for 3 hr and was then cooled to RT. The volatiles were removed in vacuo and the remaining aq solution was acidified to pH 2 by the addition of 1 M hydrochloric acid. The mixture was extracted with a mixture of DCM and MeOH (9:1) and the organic extracts were dried and evaporated in vacuo to afforded the title compound as a brown gum (138 mg, 97% yield, 93% pure by ¹H NMR); $R^t$ 3.21 min (Method 1a); m/z 429 (M+H)⁺ (ES⁺). This material was used in subsequent steps without additional purification.

Methyl 5-cyclopropyl-2-(7-oxa-2-azaspiro[3.5]nonan-2-yl)nicotinate

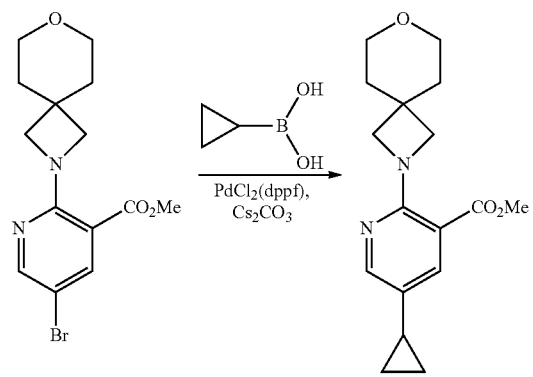 [SMILES: COC(=O)c1cc(Br)cnc1N1CC2(CCOCC2)C1 ; OB(O)C1CC1 ; COC(=O)c1cc(C2CC2)cnc1N1CC2(CCOCC2)C1]

A mixture of methyl 5-bromo-2-(7-oxa-2-azaspiro[3.5]nonan-2-yl)nicotinate (1.50 g, 4.40 mmol), cyclopropylboronic acid (0.77 g, 9.00 mmol), cesium carbonate (3.23 g, 9.90 mmol) and Pd(dppf)Cl$_2$ (0.33 g, 0.45 mmol) was suspended in water (7.5 mL) and 1,4-dioxane (15.0 mL) and degassed with nitrogen for 10 min. The reaction mixture was heated at 100° C. for 6 hr, cooled to RT and was then partitioned between EtOAc (100 mL) and water (100 mL). The organic layer was separated and was washed with brine (100 mL) and then dried and evaporated in vacuo. The crude residue thus obtained was purified by flash column chromatography (SiO$_2$, 40 g, 0-100% EtOAc in isohexane, gradient elution) to afford the title compound, as a colourless oil (1.17 g, 86% yield, 91% pure by $^1$H NMR); R$^t$ 1.44 min (Method 1a); m/z 303 (M+H)$^+$ (ES$^+$). This material was used in subsequent steps without additional purification.

5-Cyclopropyl-2-(7-oxa-2-azaspiro[3.5]nonan-2-yl)nicotinic Acid

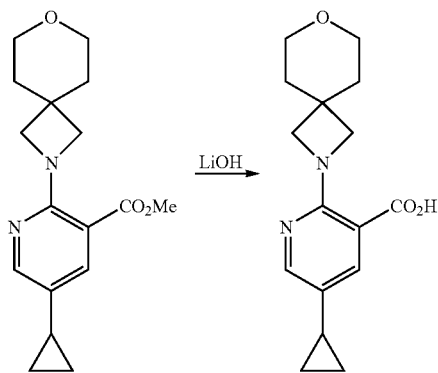 [SMILES: COC(=O)c1cc(C2CC2)cnc1N1CC2(CCOCC2)C1 ; "LiOH" ; O=C(O)c1cc(C2CC2)cnc1N1CC2(CCOCC2)C1]

To a solution of methyl 5-cyclopropyl-2-(7-oxa-2-azaspiro[3.5]nonan-2-yl)nicotinate (1.17 g, 3.87 mmol) in a mixture of THF:MeOH:water (2:1:1, 32 mL) was added lithium hydroxide (0.19 g, 7.7 mmol). The reaction mixture was heated to 50° C. for 6 hr and was then allowed to cool to RT overnight. The volatiles were removed in vacuo and the remaining aq solution acidified to pH 4 by the addition of 1 M hydrochloric acid. The mixture was extracted with EtOAc (3×100 mL) and the combined organic extracts were dried and evaporated in vacuo to afforded the title compound as a white foam (0.91 g, 95% pure by $^1$H NMR, 82% yield); R$^t$ 0.92 min (Method 1a); m/z 289 (M+H)$^+$ (ES$^+$).

2-Oxo-1,5,7,8-tetrahydro-2H-pyrano[4,3-b]pyridine-3-carboxylic Acid

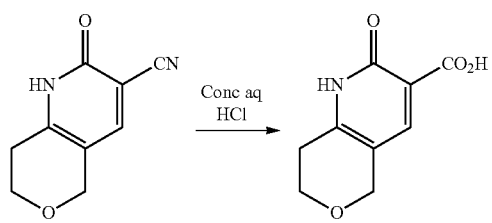 [SMILES: N#Cc1cc2c([nH]c1=O)CCOC2 ; O=C(O)c1cc2c([nH]c1=O)CCOC2]

A mixture of 2-oxo-1,5,7,8-tetrahydro-2H-pyrano[4,3-b]pyridine-3-carbonitrile (2.50 g, 14.2 mmol) and conc hydrochloric acid (28.4 mL) was heated at reflux for 6 hr. The resulting solution was concentrated to one third of the original volume and the resulting precipitate filtered and retained. The filtrate was evaporated in vacuo and the resulting solid triturated with water (20 mL) and filtered. This solid was combined with that previously obtained and partitioned between DCM:MeOH (9:1, 500 mL) and water (200 mL). The organic extracts were separated and the aq layer further extracted with DCM:MeOH (9:1, 5×300 mL). The combined organic extracts were dried and evaporated in vacuo to afford the title compound as a brown solid (2.45 g, 92% pure by HPLC, 88% yield); R$^t$ 0.70 min (Method 1a); m/z 196 (M+H)$^+$ (ES$^+$). This material was used in subsequent steps without additional purification.

2-Chloro-7,8-dihydro-5H-pyrano[4,3-b]pyridine-3-carbonyl Chloride

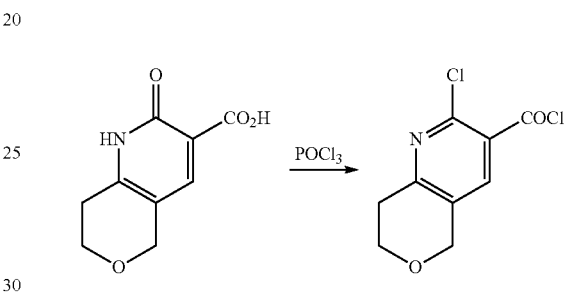

A solution of 2-oxo-1,5,7,8-tetrahydro-2H-pyrano[4,3-b]pyridine-3-carboxylic acid (500 mg, 2.56 mmol) in phosphoryl trichloride (5.12 mL, 2.56 mmol) was heated at reflux for 18 hr and then was cooled to RT and evaporated in vacuo to afford the title compound as a colourless solid (100 mg, 28% yield); R$^t$ 1.48 min (Method 1a); m/z 228 (M+H)$^+$ [methyl ester] (ES$^+$). This material was used in the subsequent step without additional purification.

2-Chloro-5,6,7,8-tetrahydroquinoline-3-carbonyl Chloride

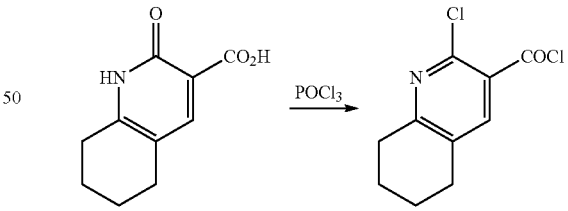

A solution of 2-oxo-1,2,5,6,7,8-hexahydroquinoline-3-carboxylic acid (1.00 g, 5.18 mmol) and phosphoryl trichloride (10.0 mL, 107 mmol) was heated at 105° C. for 18 hr and was cooled and evaporated in vacuo. To the resulting residue was added ice (5 g) and the precipitate that formed was isolated by filtration, washed with cold water (2.0 mL) and then dried to afford the title compound as an off-white solid (0.52 g, 85% pure by HPLC, 44% yield); R$^t$ 2.27 min (Method 1a); m/z 240 (M+H)$^+$ [ethyl ester] (ES$^+$). This material was used in the subsequent step without additional purification.

Benzyl 5,6,7,8-tetrahydro-4H-thieno[3,2-b]azepine-4-carboxylate

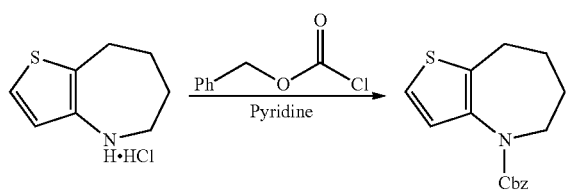

To a solution of 5,6,7,8-tetrahydro-4H-thieno[3,2-b]azepine hydrochloride (9.85 g, 51.9 mmol) and pyridine (9.24 mL, 114 mmol) in DCM (87 mL) at 0° C. was added dropwise benzyl chloroformate (12.6 mL, 88.0 mmol). The resulting mixture was stirred at 0° C. for 30 min, then warmed to RT for 18 hr. Water (150 mL) was added and the resulting biphasic mixture separated. The aq layer was extracted with DCM (30 mL) and the combined organic extracts were dried and evaporated in vacuo. The residue was purified by flash column chromatography (SiO$_2$, 120 g, 0-50% EtOAc in isohexane, gradient elution) to afford the title compound as a pale yellow oil that solidified on standing (15.0 g, quant.); R$^t$2.59 min (Method 1a); m/z 288 (M+H)$^+$ (ES$^+$); $^1$H NMR δ: 1.61 (2H, br), 1.81 (2H, br), 2.74 (2H, br), 3.51 (2H, br), 5.09 (2H, s), 6.90 (1H, br d), 7.13 (1H, d), 7.22-7.45 (5H, over-lapping m).

Benzyl 8-oxo-5,6,7,8-tetrahydro-4H-thieno[3,2-b]azepine-4-carboxylate

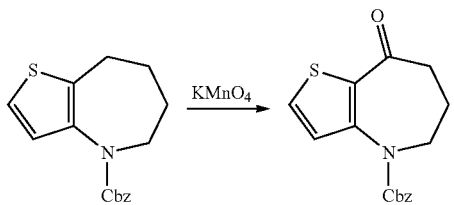

To a solution of benzyl 5,6,7,8-tetrahydro-4H-thieno[3,2-b]azepine-4-carboxylate (14.3 g, 49.8 mmol) in acetone (572 mL) at RT was added MgSO$_4$ (10.4 g, 87.0 mmol) and a solution of KMnO$_4$ (13.7 g, 87.0 mmol) in water (286 mL). The resulting mixture was heated at 70° C. for 2 hr, then cooled to RT and filtered. The filtrate was concentrated in vacuo and the resulting aq suspension (~50 mL) was taken up into acetone (572 mL) and additional KMnO$_4$ (13.7 g, 87.0 mmol), MgSO$_4$ (10.4 g, 87.0 mmol) and water (230 mL) were added. This mixture was heated at 70° C. for 2 hr, then cooled to RT and filtered. The filtrate was concentrated in vacuo and the resulting aq emulsion was extracted with DCM (3×150 mL). The combined organic extracts were dried and evaporated in vacuo. and the residue was purified by flash column chromatography (SiO$_2$, 220 g, 0-50% EtOAc in isohexane, gradient elution) to afford the title compound as a pale yellow oil (4.56 g, 30% yield); R$^t$2.20 min (Method 1a); m/z 302 (M+H)$^+$ (ES$^+$); $^1$H NMR δ: 2.07 (2H, p), 2.69 (2H, apparent t), 3.81 (2H, apparent t), 5.22 (2H, s), 7.25 (1H, d), 7.31-7.42 (5H, over-lapping m), 7.86 (1H, d).

Benzyl 8-chloro-7-formyl-5,6-dihydro-4H-thieno[3,2-b]azepine-4-carboxylate

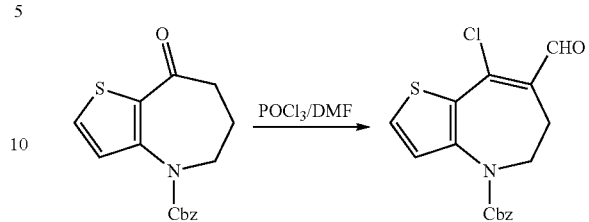

To neat DMF (25.0 mL) at 0° C. was added phosphoryl trichloride (1.75 mL, 18.8 mmol) and the resulting mixture then added to a solution of benzyl 8-oxo-5,6,7,8-tetrahydro-4H-thieno [3,2-b]azepine-4-carboxylate (5.15 g, 17.1 mmol) in DMF (60 mL) at 0° C. The reaction mixture was stirred at 0° C. for 20 min, heated to 50° C. for 5 hr and then cooled to RT and poured into sat aq NaOAc (800 mL). The mixture was extracted with DCM (3×120 mL) and the combined organic extracts were washed with water (3×250 mL) and then dried and evaporated in vacuo. The residue was taken up into DCM (30 mL) and was washed with water (2×100 mL). The organic layer was passed through a phase separator and the volatiles evaporated in vacuo to afford the title compound as a dark orange oil (5.82 g, 78% pure by $^1$H NMR); R$^t$2.61 min (Method 1a); m/z 348 (M+H)$^+$ (ES$^+$). This material was used in the subsequent step without additional purification.

4-Benzyl 8-ethyl 5,6-dihydro-4H-dithieno[3,2-b:2',3'-d]azepine-4,8-dicarboxylate

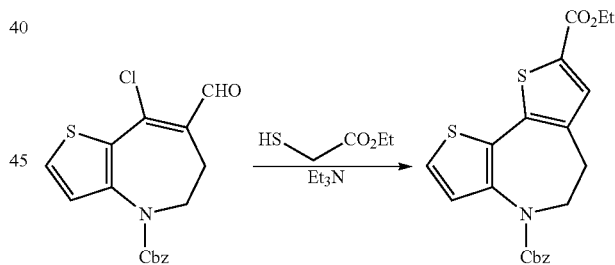

To a suspension in pyridine (35 mL) of benzyl 8-chloro-7-formyl-5,6-dihydro-4H-thieno[3,2-b]azepine-4-carboxylate (5.82 g, 13.1 mmol) at RT was added ethyl 2-mercaptoacetate (2.86 mL, 26.1 mmol) followed by triethylamine (11.8 mL, 85.0 mmol). The mixture was heated at 70° C. for 1 hr and at 115° C. for 4 hr and was then allowed to cool to RT for 18 hr. The mixture was poured into water (150 mL) and the resulting yellow suspension was filtered. The solid thus obtained was triturated with MeOH (100 mL), collected by filtration, washed with MeOH (100 mL) and then dried to afford the title compound as an off-white solid (3.90 g, 55% yield over 2 steps); R$^t$ 2.92 min (Method 1a); m/z 414 (M+H)$^+$ (ES$^+$); $^1$H NMR δ: 1.29 (3H, t), 3.14 (2H, apparent t), 3.74 (2H, apparent t), 4.27 (2H, q), 5.17 (2H, s), 7.14 (1H, br d), 7.29-7.41 (5H, over-lapping m), 7.47 (1H, d), 7.64 (1H, s).

Ethyl 5,6-dihydro-4H-dithieno[3,2-b:2',3'-d]azepine-8-carboxylate

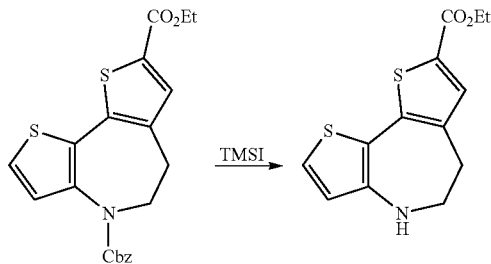 [SMILES: "TMSI" ; CCOC(=O)c1cc2c(s1)-c1sccc1N(C(=O)OCc1ccccc1)CC2 ; CCOC(=O)c1cc2c(s1)-c1sccc1NCC2]

To a solution in DCM (40 mL) of 4-benzyl 8-ethyl 5,6-dihydro-4H-dithieno[3,2-b:2',3'-d]azepine-4,8-dicarboxylate (1.00 g, 2.42 mmol) at 0° C. was added TMSI (658 µL, 4.84 mmol). The resulting mixture was allowed to warm to RT over 4 hr and then EtOH (40 mL) and SCX resin (30 g) were added and the suspension stirred for 30 min. The resin was recovered by filtration, washed with MeOH (250 mL) and the product eluted with methanolic ammonia (0.7 M, 300 mL). The volatiles were evaporated in vacuo to afford the title compound as a dark yellow oil (574 mg, 85% yield); $R^r$ 2.45 min (Method 1a); m/z 280 (M+H)$^+$ (ES$^+$); $^1$H NMR δ: 1.26 (3H, t), 2.95-3.00 (2H, m), 3.28-3.35 (2H, m), 4.22 (2H, q), 6.56 (1H, d), 6.90 (1H, apparent t), 7.29 (1H, d), 7.44 (1H, s).

(4-Nitrophenyl)(5,6,7,8-tetrahydro-4H-thieno[3,2-b]azepin-4-yl)methanone

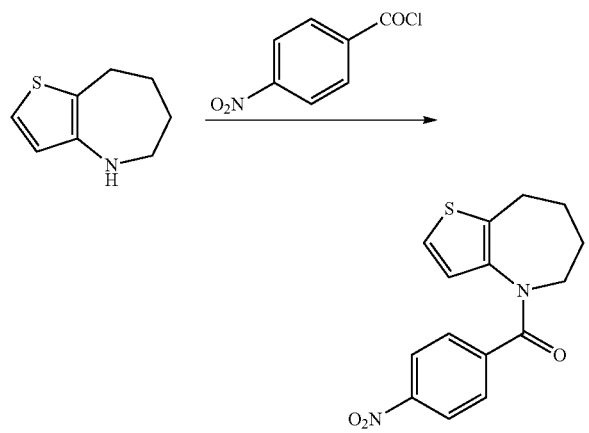 [SMILES: c1cc2c(s1)CCCCN2 ; O=C(Cl)c1ccc([N+](=O)[O-])cc1 ; O=C(c1ccc([N+](=O)[O-])cc1)N1CCCCc2sccc21]

To a solution of 5,6,7,8-tetrahydro-4H-thieno[3,2-b]azepine (13.2 g, 86.0 mmol) in pyridine (60 mL) was added a solution of 4-nitrobenzoyl chloride (16.0 g, 86.0 mmol) in MeCN (120 mL) at RT. The resulting mixture was maintained at this temperature for 1 hr and was then poured into water (300 mL). The precipitate thus formed was collected by filtration, washed with water (2×100 mL) and dried to afford the title compound as a pale brown solid (24.3 g, 93% yield, 93% pure by HPLC); $R^r$ 2.29 min (Method 1a); m/z 303 (M+H)$^+$ (ES$^+$). This material was used in the subsequent step without additional purification. [See WO 1996/22294 Example 5, page 45.]

4-(4-Nitrobenzoyl)-4,5,6,7-tetrahydro-8H-thieno[3,2-b]azepin-8-one

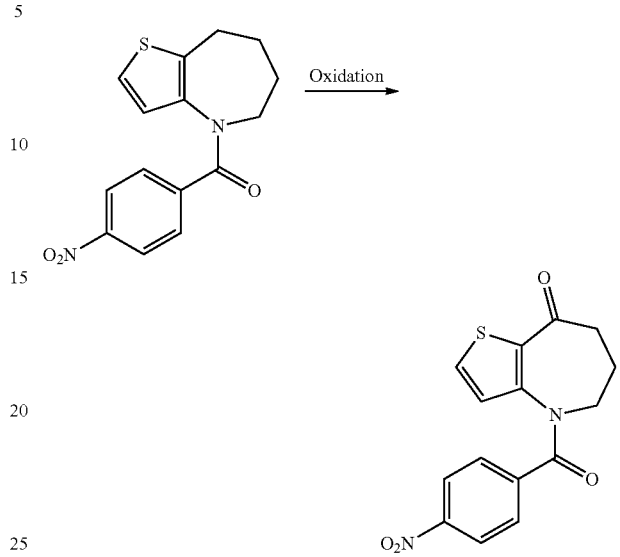

a. Oxidation with Potassium Permanganate

To a solution of (4-nitrophenyl)(5,6,7,8-tetrahydro-4H-thieno[3,2-b]azepin-4-yl)methanone (10.0 g, 33.1 mmol) in acetone (280 mL) at RT was added MgSO$_4$ (6.93 g, 57.5 mmol), water (140 mL) and then KMnO$_4$ (9.09 g, 57.5 mmol). The resulting mixture was heated at 70° C. for 4 hr, then cooled to RT and filtered through celite (10 g). The celite pad was washed with DCM (800 mL) and the combined filtrates were evaporated in vacuo. The resulting yellow solid was purified by flash column chromatography (SiO$_2$, 220 g, 10-100% EtOAc in isohexane, gradient elution). The solid thus obtained was triturated with MeOH (20 mL), collected by filtration and dried to afford the title compound as a white solid (5.34 g, 51% yield [65% based on recovered s/m], 90% pure by HPLC); $R^r$ 1.90 min (Method 1a); m/z 317 (M+H)$^+$ (ES$^+$). This material was used in the subsequent step without additional purification. [See WO 1996/22294, Example 6, page 45.]

b. Oxidation with Potassium Persulfate

To a solution of (4-nitrophenyl)(5,6,7,8-tetrahydro-4H-thieno[3,2-b]azepin-4-yl)methanone (1.00 g, 3.31 mmol) in a mixture of acetonitrile (35 mL) and water (29 mL) at RT was added CuSO$_4$ (2.11 g, 13.2 mmol) and then K$_2$S$_2$O$_8$ (3.58 g, 13.2 mmol). The resulting mixture was heated at 85° C. for 20 min, then cooled to RT and partitioned between water (100 mL) and EtOAc (30 mL). The aq layer was separated and was extracted with EtOAc (30 mL) and the combined organics then dried and evaporated in vacuo. The resulting residue was purified by flash column chromatography (SiO$_2$, 40 g, 10-100% EtOAc in isohexane, gradient elution) to afford the title compound as an off-white solid (391 mg, 37% yield); $R^r$ 1.91 min (Method 1a); m/z 317 (M+H)$^+$ (ES$^+$). Late running fractions gave additional product which was isolated as a light brown solid (316 mg, 30% yield, 93% pure by HPLC); $R^r$ 1.90 min (Method 1a); m/z 317 (M+H)$^+$ (ES$^+$). Both batches were used in the subsequent step without additional purification.

Oxidation using potassium persulfate (b.) has been shown to produce a higher yield (70% compared to 37%) when performed using 9.00 g of (4-nitrophenyl)(5,6,7,8-tetrahydro-4H-thieno[3,2-b]azepin-4-yl)methanone compared to using 1.00 g of starting material:

To a solution of (4-nitrophenyl)(5,6,7,8-tetrahydro-4H-thieno[3,2-b]azepin-4-yl)methanone (9.00 g, 29.8 mmol) in a mixture of acetonitrile (311 mL) and water (257 mL) at RT was added CuSO$_4$ (19.0 g, 119 mmol) and then K$_2$S$_2$O$_8$ (32.2 g, 119 mmol). The mixture was heated at 85° C. for 20 min, then cooled to RT and partitioned between water (600 mL) and EtOAc (400 mL). The aq layer was separated and was extracted with EtOAc (2×200 mL) and the combined organics were then dried and evaporated in vacuo. The residue was triturated with MeOH (200 mL) and the solid that formed was collected by filtration and dried to afford the title compound as an orange solid (6.61 g, 70% yield); R$^t$ 1.90 min (Method 1a); m/z 317 (M+H)$^+$ (ES$^+$); $^1$H NMR δ: 2.08-2.15 (2H, m), 2.88-2.91 (2H, m), 3.97 (2H, apparent t), 6.52-6.61 (1H, br), 7.68 (1H, d), 7.71 (2H, d), 8.18 (2H, d).

8-Chloro-4-(4-nitrobenzoyl)-5,6-dihydro-4H-thieno[3,2-b]azepine-7-carbaldehyde

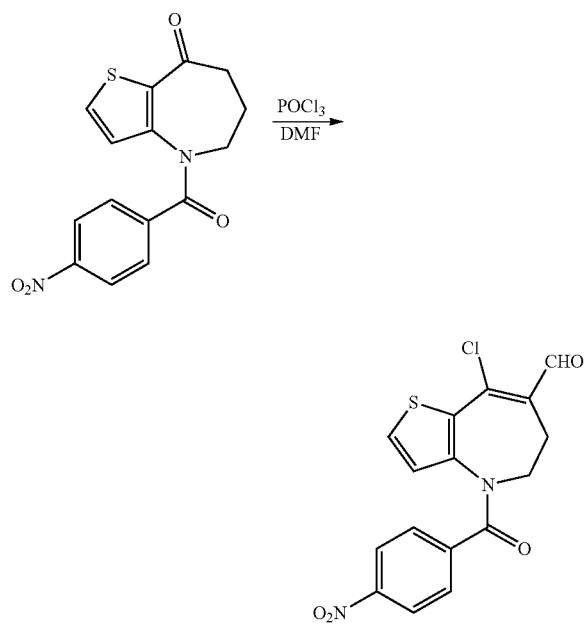

To neat DMF (35.0 mL) at 0° C. was added phosphoryl trichloride (1.62 mL, 17.4 mmol) dropwise. The resulting mixture was added to a solution of 4-(4-nitrobenzoyl)-4,5,6,7-tetra hydro-8H-thieno[3,2-b]azepin-8-one (5.00 g, 15.8 mmol) in DMF (70 mL) at 0° C. and after 15 min the mixture was warmed to RT for 30 min and then heated to 50° C. for 4 hr. The reaction mixture was cooled to RT, poured into sat aq NaOAc (700 mL) and extracted into EtOAc (3×200 mL). The combined organic extracts were washed with brine (200 mL) and then dried and evaporated in vacuo to afford the title compound as a pale yellow solid (7.79 g, 70% pure by HPLC); R$^t$ 2.30 min (Method 1a); m/z 363 (M+H)$^+$ (ES$^+$). The remainder (30%) was identified as unreacted starting material and the product thus obtained was used in the subsequent step without additional purification.

Ethyl 4-(4-nitrobenzoyl)-5,6-dihydro-4H-dithieno[3,2-b:2',3'-d]azepine-8-carboxylate

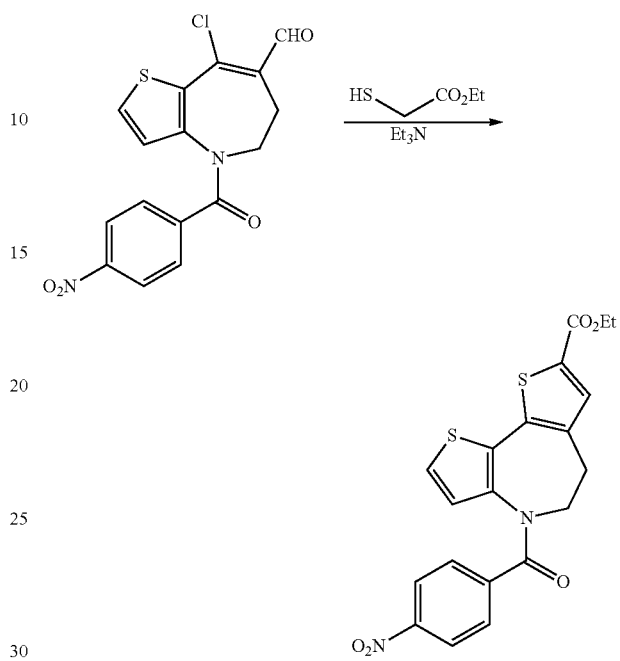

To a solution, in pyridine (26.0 mL), of 8-chloro-4-(4-nitrobenzoyl)-5,6-dihydro-4H-thieno[3,2-b]azepine-7-carbaldehyde (6.43 g, 12.4 mmol) was added ethyl 2-mercaptoacetate (2.72 mL, 24.8 mmol) followed by triethylamine (11.2 mL, 81.0 mmol). The mixture was heated at 70° C. for 1 hr and then to 115° C. for an additional 2 hr. After cooling to RT the resulting mixture was poured into water (700 mL) and extracted into EtOAc (2×200 mL). The combined organic extracts were passed through a phase separator and the organics were evaporated in vacuo. The yellow solid thus obtained was purified by flash column chromatography (SiO$_2$, 220 g, 10-100% EtOAc in isohexane, gradient elution) to afford the title compound as a yellow solid (3.12 g, 59% yield, 90% pure by HPLC); R$^t$ 2.68 min (Method 1a); m/z 429 (M+H)$^+$ (ES$^+$). This material was used in the subsequent step without additional purification.

tert-Butyl 4-(4-nitrobenzoyl)-5,6-dihydro-4H-dithieno[3,2-b:2',3'-d]azepine-8-carboxylate

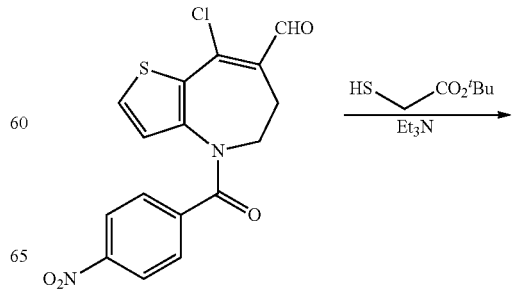

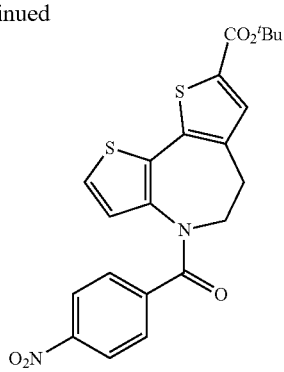

To a solution in pyridine (4.0 mL) of 8-chloro-4-(4-nitrobenzoyl)-5,6-dihydro-4H-thieno[3,2-b]azepine-7-carbaldehyde (1.00 g, 1.93 mmol) was added tert-butyl 2-mercaptoacetate (572 mg, 3.86 mmol) followed by triethylamine (1.75 mL, 12.5 mmol). The mixture was heated at 70° C. for 1 hr and then at 115° C. for an additional 2 hr. After cooling to RT the resulting mixture was poured into water (100 mL) and extracted into EtOAc (2×40 mL). The combined organic extracts were passed through a phase separator and then evaporated in vacuo. The orange oily residue was purified by flash column chromatography (SiO$_2$, 40 g, 10-100% EtOAc in isohexane, gradient elution) to afford the title compound as a viscous yellow gum (953 mg, 91% pure by HPLC); R$^t$ 2.93 min (Method 1a); m/z 400 (M-$^t$Bu+H)$^+$ (ES$^+$). This material was used in the subsequent step without additional purification.

Ethyl 4-(2-fluoro-4-nitrobenzoyl)-5,6-dihydro-4H-dithieno[3,2-b:2',3'-d]azepine-8-carboxylate

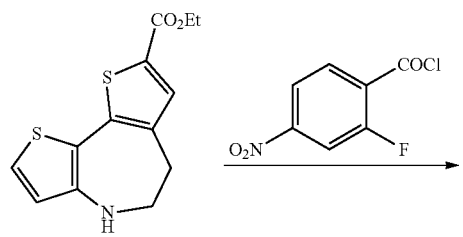

To a suspension of 2-fluoro-4-nitrobenzoic acid (1.05 g, 5.69 mmol) in toluene (10 mL) was added thionyl chloride (831 μL, 11.4 mmol) and a two drops of DMF. The resulting mixture was heated at reflux for 2 hr, then cooled to RT and evaporated in vacuo. The residue was taken up into MeCN (10.0 mL) and was added to a solution of ethyl 5,6-dihydro-4H-dithieno[3,2-b:2',3'-d]azepine-8-carboxylate (1.06 g, 3.79 mmol) in pyridine (10.0 mL). After stirring at RT for 2 hr the mixture was evaporated in vacuo and the residue triturated with water (60 mL). The solid that formed was collected by filtration and dried to afford the title compound as a dark orange solid (1.56 g, 92% yield, 94% pure by HPLC); R$^t$ 2.68 min (Method 1a); m/z 468 (M+Na)$^+$ 447 (M+H)$^+$ (ES$^+$). This material was used in the subsequent step without additional purification.

Ethyl 4-(4-aminobenzoyl)-5,6-dihydro-4H-dithieno[3,2-b:2',3'-d]azepine-8-carboxylate

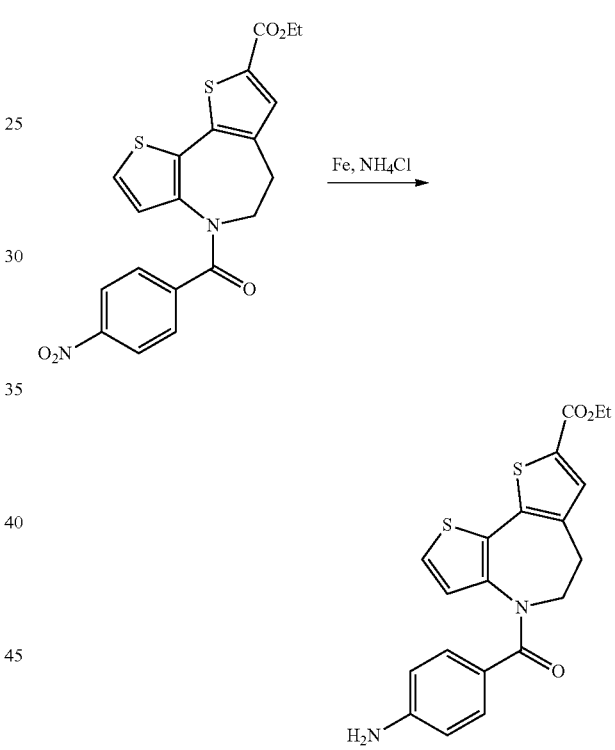

To a suspension of ethyl 4-(4-nitrobenzoyl)-5,6-dihydro-4H-dithieno[3,2-b:2',3'-d]azepine-8-carboxylate (500 mg, 1.17 mmol) in a mixture of EtOH and water (3:1, 32 mL) at RT was added iron powder (652 mg, 11.7 mmol) and ammonium chloride (624 mg, 11.7 mmol). The resulting mixture was stirred at reflux for 30 min, then cooled to RT and filtered through a celite pad (5.0 g). The pad was washed with EtOH (30 mL) and the combined filtrates were evaporated in vacuo. The resulting yellow solid was triturated with water (30 mL), collected by filtration and dried to afford the title compound as a light yellow solid (450 mg, 97% yield); R$^t$ 2.32 min (Method 1a); m/z 399 (M+H)$^+$ (ES$^+$); $^1$H NMR δ: 1.30 (3H, t), 3.14 (2H, apparent t), 3.87-4.02 (2H, br), 4.29 (2H, q), 5.58-5.68 (2H, br), 6.34 (1H, d), 6.38 (2H, d), 6.94 (2H, d), 7.27 (1H, d), 7.68 (1H, s).

Ethyl 4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxylate

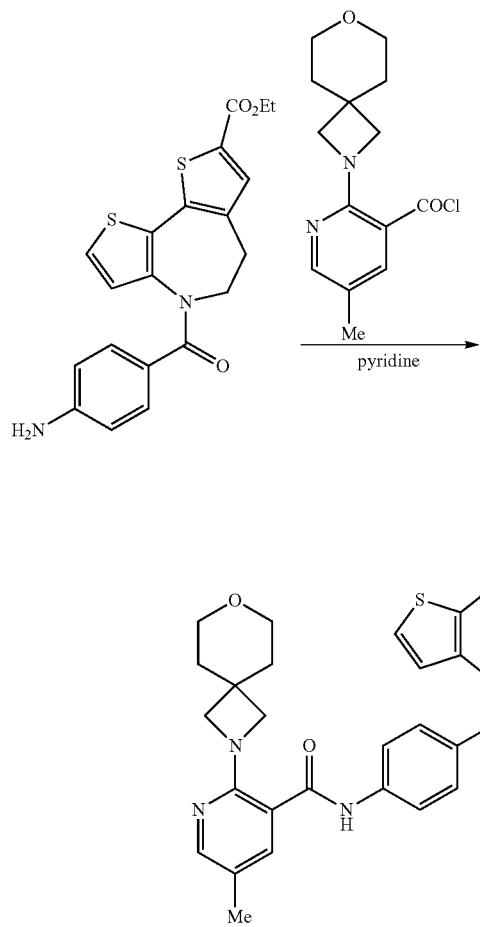

To a suspension of 5-methyl-2-(7-oxa-2-azaspiro[3.5]nonan-2-yl)nicotinic acid (592 mg, 2.26 mmol) in DCM (5.6 mL) was added 1-chloro-N,N,2-trimethylprop-1-en-1-amine (598 µL, 4.52 mmol). The resulting mixture was stirred at RT for 1.5 hr and was then evaporated in vacuo. The residue was taken up into DCM (5.6 mL) and was added slowly to an ice cold solution of ethyl 4-(4-aminobenzoyl)-5,6-dihydro-4H-dithieno[3,2-b:2',3'-d]azepine-8-carboxylate (450 mg, 1.13 mmol) in pyridine (20 mL). The resulting mixture was warmed to RT for 30 min and then partitioned between water (20 mL) and a mixture of DCM and MeOH (9:1, 50 mL). The aq layer was separated and was extracted with a mixture of DCM and MeOH (9:1, 2×40 mL). The combined organic extracts were washed with brine (50 mL) and then dried and evaporated in vacuo. The crude product was purified by flash column chromatography (SiO$_2$, 40 g, 0-10% MeOH in DCM, gradient elution) and the orange residue so obtained was triturated with water (20 mL) under sonication for 10 min. The resulting precipitate was collected by filtration, washed with water (20 mL) and then dried in vacuo to afford the title compound as beige solid (562 mg, 77% yield, 92% pure by HPLC); R$^t$ 2.03 min (Method 1a); m/z 643 (M+H)$^+$ (ES$^+$). This material was used in the subsequent step without additional purification.

Ethyl 4-(4-(2-chloro-6,7-dihydro-5H-cyclopenta[b]pyridine-3-carboxamido)benzoyl)-5,6-dihydro-4H-dithieno[3,2-b:2',3'-d]azepine-8-carboxylate

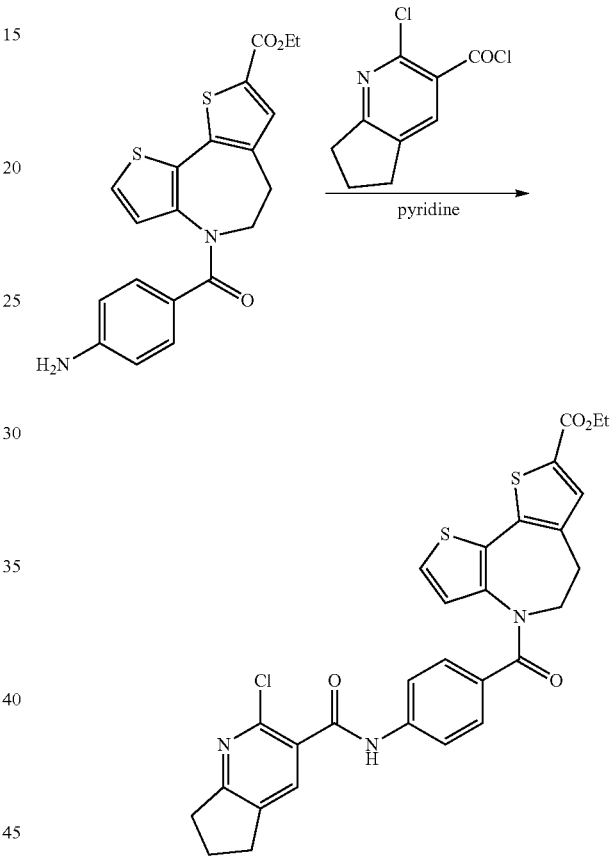

To a suspension of 2-chloro-6,7-dihydro-5H-cyclopenta[b]pyridine-3-carboxylic acid (387 mg, 1.96 mmol) in DCM (12 mL) was added 1-chloro-N,N,2-trimethylprop-1-en-1-amine (259 µL, 1.96 mmol). The resulting mixture was stirred at RT for 15 min and then added to a solution of ethyl 4-(4-aminobenzoyl)-5,6-dihydro-4H-dithieno[3,2-b:2',3'-d]azepine-8-carboxylate (600 mg, 1.51 mmol) in pyridine (10 mL). After 1 hr, water (30 mL) was added and the biphasic mixture was passed through a phase separator. The organic phase was evaporated in vacuo and the orange oil thus obtained purified by flash column chromatography (SiO$_2$, 24 g, 0-100% EtOAc in isohexane, gradient elution) to afford the title compound as a white solid (723 mg, 83% yield, 92% pure by HPLC); R$^t$ 2.66 min (Method 1a); m/z 579 (M+H)$^+$ (ES$^+$). This material was used in the subsequent step without additional purification.

45

Ethyl 4-(4-(2-(7-oxa-2-azaspiro[3.5]nonan-2-yl)-6,7-dihydro-5H-cyclopenta[b]pyridine-3-carboxamido)benzoyl)-5,6-dihydro-4H-dithieno[3,2-b:2',3'-d]azepine-8-carboxylate

46

4-(4-(5-Methyl-2-(7-oxa-2-azaspiro[3.5]nonan-2-yl)nicotinamido)benzoyl)-5,6-dihydro-4H-dithieno[3,2-b:2',3'-d]azepine-8-carboxylic Acid

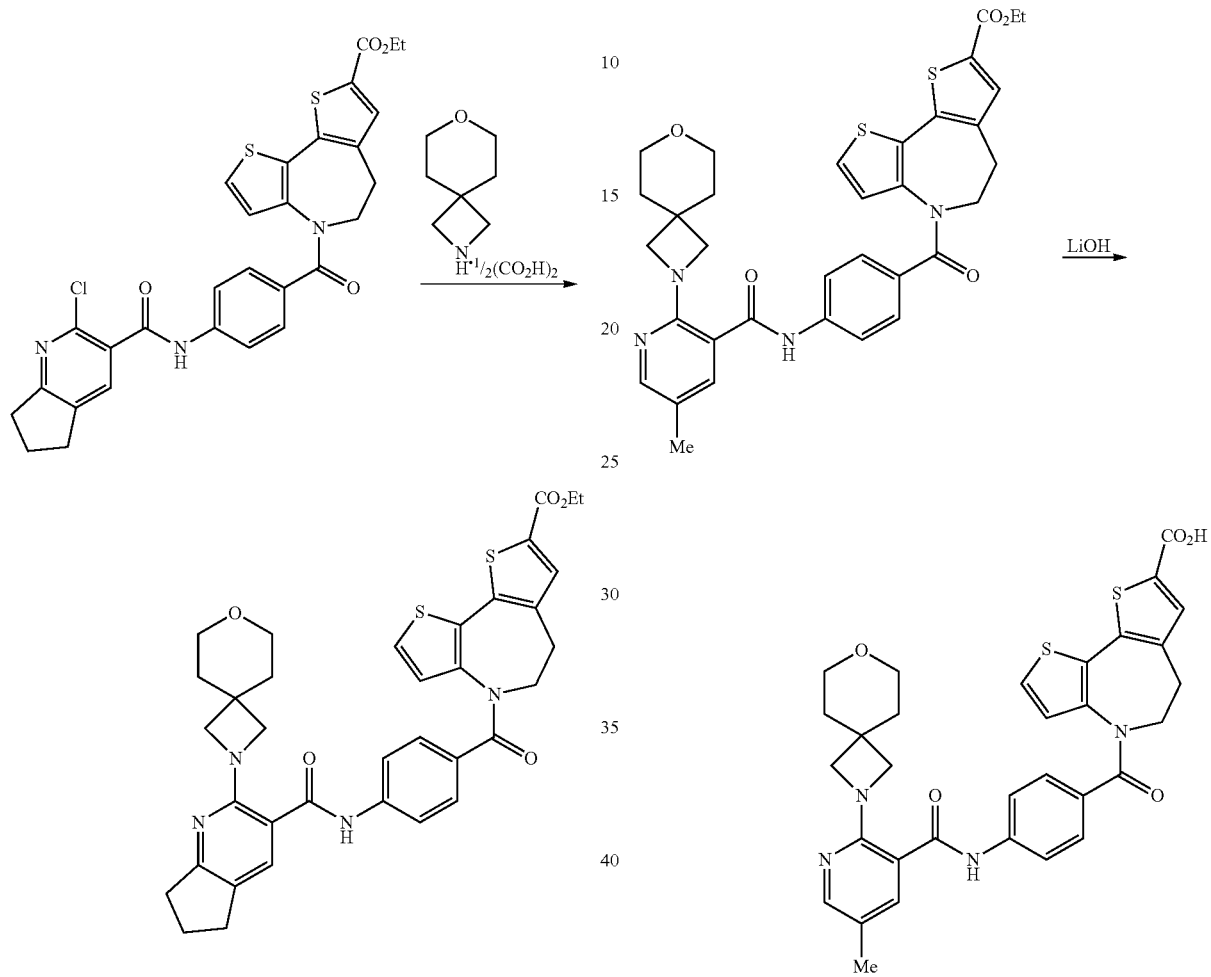

To a solution of ethyl 4-(4-(2-chloro-6,7-dihydro-5H-cyclopenta[b]pyridine-3-carboxamido)benzoyl)-5,6-dihydro-4H-dithieno[3,2-b:2',3'-d]azepine-8-carboxylate (723 mg, 1.25 mmol) and 7-oxa-2-azaspiro[3.5]nonane (477 mg, 3.75 mmol) in NMP (40 mL) was added $K_2CO_3$ (1.04 g, 7.50 mmol). The reaction mixture was heated at 120° C. for 3 hr, and at 140° C. for an additional 4 hr and then cooled to RT overnight. The mixture was partitioned between water (50 mL) and EtOAc (50 mL) and the organic phase was separated, washed with brine (2×30 mL) and then passed through a phase separator and evaporated in vacuo. The brown oil thus obtained was purified by flash column chromatography ($SiO_2$, 40 g, 0-100% EtOAc in isohexane, gradient elution) to afford the title compound as a pale yellow solid (798 mg, 95% yield, 66% pure by $^1H$ NMR); $R_t$ 2.17 min (Method 1a); m/z 669 (M+H)$^+$ (ES$^+$). The main impurity was identified as NMP by $^1H$ NMR and the material was used in the subsequent step without additional purification.

To a solution in THF (9.0 mL) of ethyl 4-(4-(5-methyl-2-(7-oxa-2-azaspiro[3.5]nonan-2-yl) nicotinamido)benzoyl)-5,6-dihydro-4H-dithieno[3,2-b:2',3'-d]azepine-8-carboxylate (562 mg, 0.874 mmol) was added a solution of lithium hydroxide (31.0 mg, 1.31 mmol) in water (9.0 mL). The resulting mixture was stirred at RT for 1 hr, after which time MeOH (9.0 mL) was added and the mixture was heated at 40° C. for a further 2 hr. After cooling to RT the volatiles were evaporated in vacuo and the residue was diluted with water (20 mL) and adjusted to pH 3 by the addition of glacial acetic acid. The solid that formed was collected by filtration and dried in vacuo to afford the title compound as a light yellow solid (451 mg, 84% yield, 94% pure by HPLC); $R_t$ 1.70 min (Method 1a); m/z 615 (M+H)$^+$ (ES$^+$). This material was used in the subsequent step without additional purification.

47

4-(4-(2-(7-Oxa-2-azaspiro[3.5]nonan-2-yl)-6,7-dihydro-5H-cyclopenta[b]pyridine-3-carboxamido)benzoyl)-5,6-dihydro-4H-dithieno[3,2-b:2',3'-d]azepine-8-carboxylic Acid

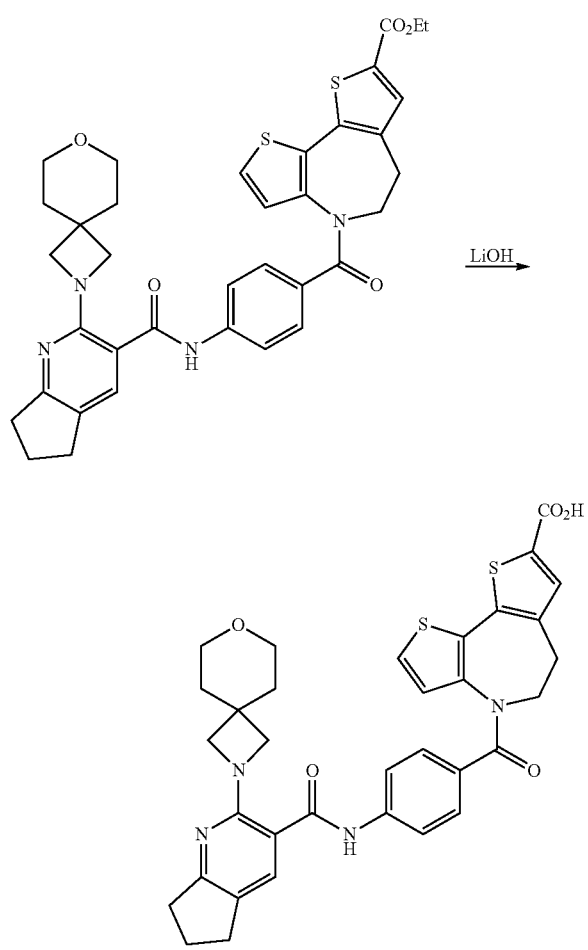 [SMILES: CCOC(=O)c1cc2c(s1)-c1sccc1N(C(=O)c1ccc(NC(=O)c3cc4c(nc3N3CC5(CCOCC5)C3)CCC4)cc1)CC2 ; "LiOH" ; O=C(O)c1cc2c(s1)-c1sccc1N(C(=O)c1ccc(NC(=O)c3cc4c(nc3N3CC5(CCOCC5)C3)CCC4)cc1)CC2]

To a solution of ethyl 4-(4-(2-(7-oxa-2-azaspiro[3.5]nonan-2-yl)-6,7-dihydro-5H-cyclopenta[b]pyridine-3-carboxamido)benzoyl)-5,6-dihydro-4H-dithieno[3,2-b:2',3'-d]azepine-8-carboxylate (798 mg, 1.19 mmol) in a mixture of THF, MeOH and water (20:7:2, 29 mL) was added lithium hydroxide (34.3 mg, 1.43 mmol) and the reaction mixture heated at 40° C. for 2 hr. The volatiles were evaporated in vacuo and the residue was dissolved in water (20 mL) and the mixture acidified to pH 3 by the addition of glacial acetic acid. The addition of DCM (20 mL) gave a biphasic mixture which was passed through a phase separator and the organics, so obtained were evaporated in vacuo to afforded the title compound as a yellow solid (675 mg, 88% yield, 90% pure by HPLC); R$^r$ 1.82 min (Method 1a); m/z 641 (M+H)$^+$ (ES$^+$). This material was used in the subsequent step without additional purification.

48

4-((Benzyloxy)carbonyl)-5,6-dihydro-4H-dithieno[3,2-b:2',3'-d]azepine-8-carboxylic Acid

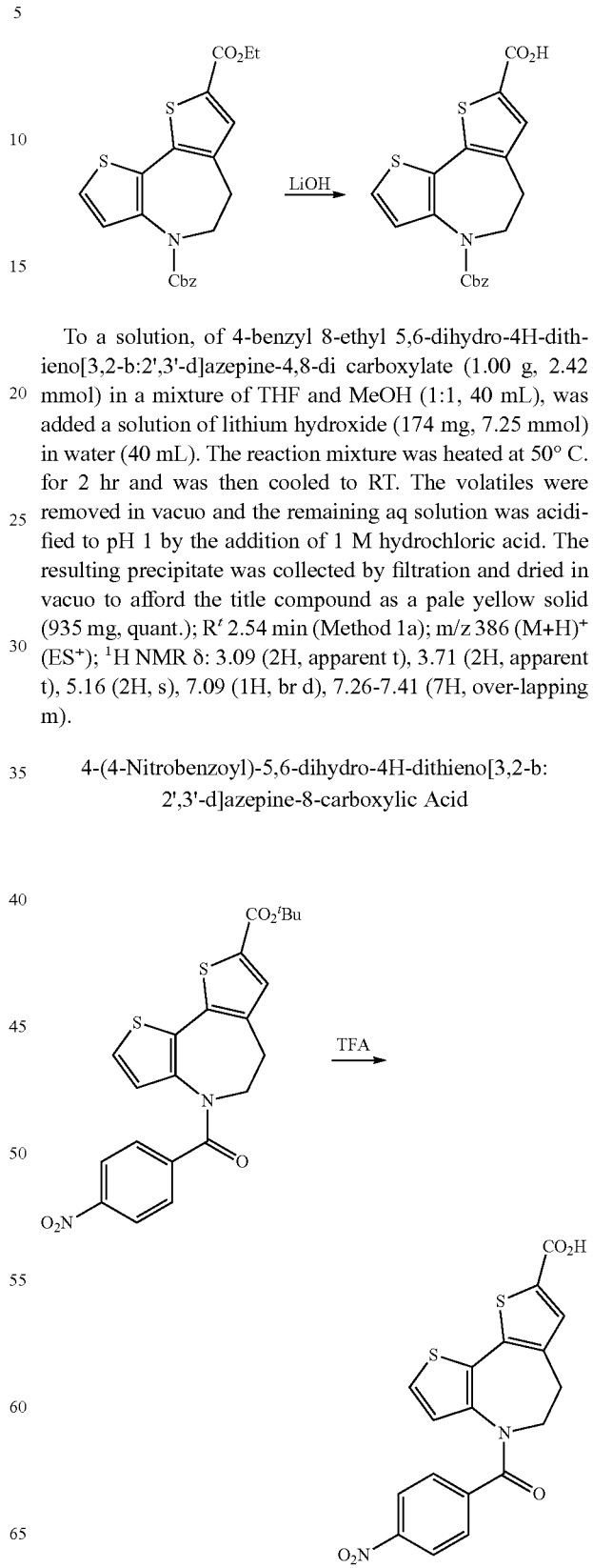

To a solution, of 4-benzyl 8-ethyl 5,6-dihydro-4H-dithieno[3,2-b:2',3'-d]azepine-4,8-di carboxylate (1.00 g, 2.42 mmol) in a mixture of THF and MeOH (1:1, 40 mL), was added a solution of lithium hydroxide (174 mg, 7.25 mmol) in water (40 mL). The reaction mixture was heated at 50° C. for 2 hr and was then cooled to RT. The volatiles were removed in vacuo and the remaining aq solution was acidified to pH 1 by the addition of 1 M hydrochloric acid. The resulting precipitate was collected by filtration and dried in vacuo to afford the title compound as a pale yellow solid (935 mg, quant.); R$^r$ 2.54 min (Method 1a); m/z 386 (M+H)$^+$ (ES$^+$); $^1$H NMR δ: 3.09 (2H, apparent t), 3.71 (2H, apparent t), 5.16 (2H, s), 7.09 (1H, br d), 7.26-7.41 (7H, over-lapping m).

4-(4-Nitrobenzoyl)-5,6-dihydro-4H-dithieno[3,2-b:2',3'-d]azepine-8-carboxylic Acid To a solution of tert-butyl 4-(4-nitrobenzoyl)-5,6-dihydro-4H-dithieno[3,2-b:2',3'-d]azepine-8-carboxylate (853 mg, 1.87 mmol) in DCM (16 mL) was added TFA (8.65 mL, 112 mmol) and the reaction mixture stirred at RT for 1 hr. The solvent was evaporated in vacuo and the residual TFA co-evaporated twice with toluene (2×80 mL) to afford the title compound as a yellow solid (730 mg, 97% yield); R$^t$ 2.26 min (Method 1a); m/z 401 (M+H)$^+$ (ES$^+$).

N-(2,6-Difluorophenyl)-4-(4-nitrobenzoyl)-5,6-dihydro-4H-dithieno[3,2-b:2',3'-d]azepine-8-carboxamide

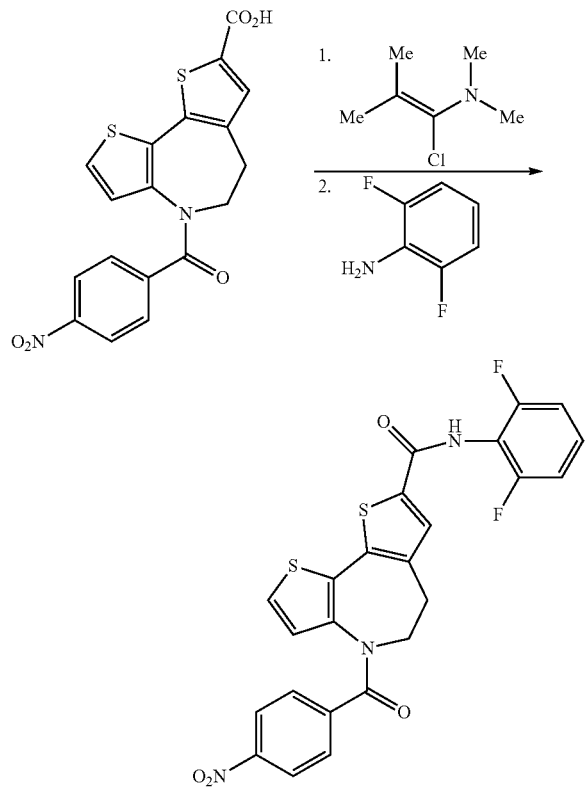

To a solution of 4-(4-nitrobenzoyl)-5,6-dihydro-4H-dithieno[3,2-b:2',3'-d]azepine-8-carboxylic acid (730 mg, 1.82 mL) in DCM (14.0 mL) at RT was added 1-chloro-N,N,2-trimethylprop-1-en-1-amine (724 µL, 5.47 mmol). The reaction mixture was stirred at RT for 30 min and was then added to a solution of 2,6-difluoroaniline (589 µL, 5.47 mmol) in pyridine (3.5 mL). After 30 min, water (24 mL) was added and the resulting biphasic mixture was passed through a phase separator. The organics were evaporated in vacuo and the residue was purified by flash column chromatography (SiO$_2$, 80 g, 10-100% EtOAc in isohexane, gradient elution) to afford the title compound as a yellow crystalline solid (944 mg, 76% pure by $^1$H NMR); 2.46 min (Method 1a); m/z 512 (M+H)$^+$ (ES$^+$). The major impurity present was identified as N,N-dimethylisobutyramide by $^1$H NMR and the product was used in the subsequent step without additional purification.

Benzyl 8-((2,6-difluorophenyl)carbamoyl)-5,6-dihydro-4H-dithieno[3,2-b:2',3'-d]azepine-4-carboxylate

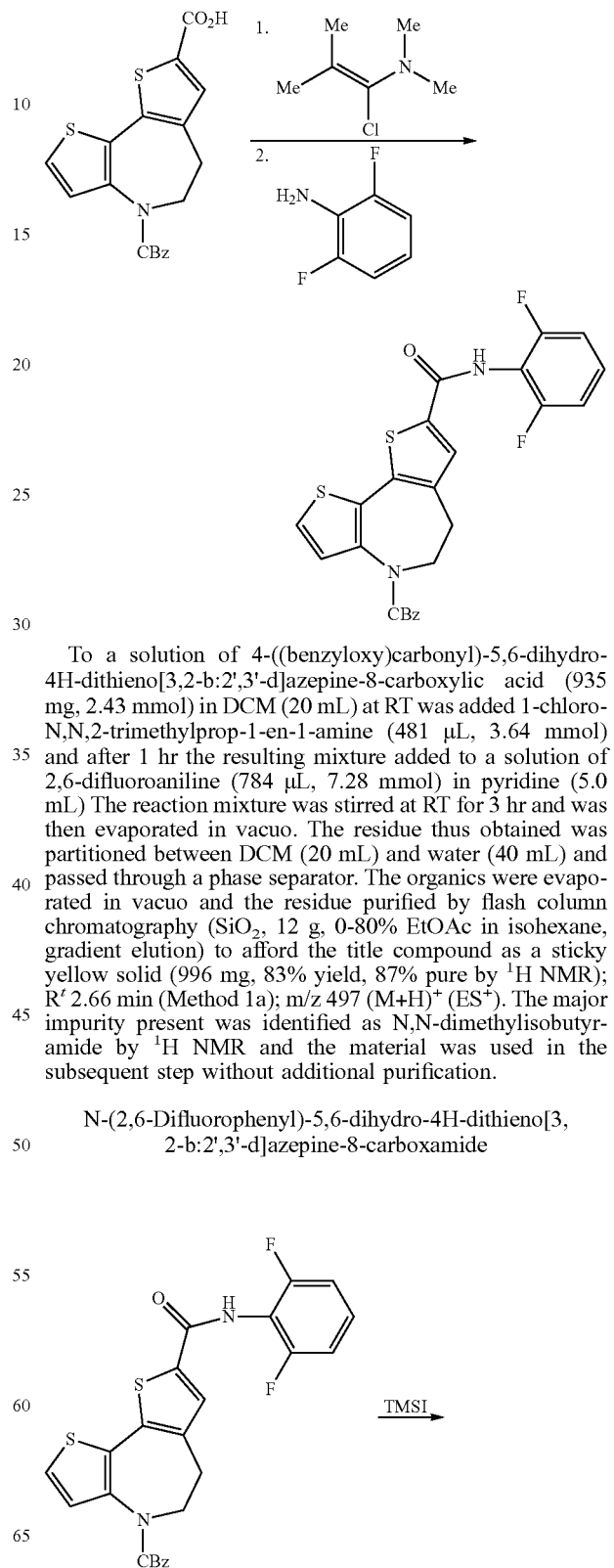

To a solution of 4-((benzyloxy)carbonyl)-5,6-dihydro-4H-dithieno[3,2-b:2',3'-d]azepine-8-carboxylic acid (935 mg, 2.43 mmol) in DCM (20 mL) at RT was added 1-chloro-N,N,2-trimethylprop-1-en-1-amine (481 µL, 3.64 mmol) and after 1 hr the resulting mixture added to a solution of 2,6-difluoroaniline (784 µL, 7.28 mmol) in pyridine (5.0 mL) The reaction mixture was stirred at RT for 3 hr and was then evaporated in vacuo. The residue thus obtained was partitioned between DCM (20 mL) and water (40 mL) and passed through a phase separator. The organics were evaporated in vacuo and the residue purified by flash column chromatography (SiO$_2$, 12 g, 0-80% EtOAc in isohexane, gradient elution) to afford the title compound as a sticky yellow solid (996 mg, 83% yield, 87% pure by $^1$H NMR); R$^t$ 2.66 min (Method 1a); m/z 497 (M+H)$^+$ (ES$^+$). The major impurity present was identified as N,N-dimethylisobutyramide by $^1$H NMR and the material was used in the subsequent step without additional purification.

N-(2,6-Difluorophenyl)-5,6-dihydro-4H-dithieno[3,2-b:2',3'-d]azepine-8-carboxamide

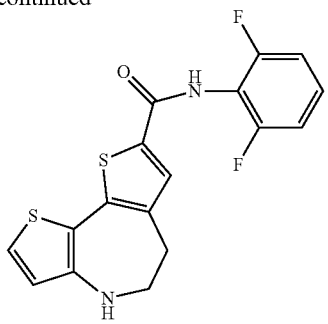

To a solution of benzyl 8-((2,6-difluorophenyl)carbamoyl)-5,6-dihydro-4H-dithieno[3,2-b:2',3'-d]azepine-4-carboxylate (996 mg, 2.01 mmol) in DCM (40 mL) at 0° C. was added TMSI (546 µL, 4.01 mmol) and the mixture allowed to warm to RT over 3 hr. An additional aliquot of TMSI [generated in situ by adding TMSCl (282 µL, 2.21 mmol) to a solution of NaI (361 mg, 2.41 mmol) in MeCN (2.0 mL) followed by stirring at RT for 10 min] was added at RT and after 18 hr the resulting mixture was diluted with EtOH (40 mL) and SCX resin (30 g) was added. The suspension was stirred for 30 min and the SCX resin was recovered by filtration and washed with MeOH (100 mL). The captured product was eluted from the resin with methanolic ammonia (0.7 M, 200 mL) and the solution thus obtained was evaporated in vacuo to afford the title compound as a yellow solid (512 mg, 70% yield); R$^t$ 2.15 min (Method 1a); m/z 363 (M+H)$^+$ (ES$^+$).

N-(2,6-Difluorophenyl)-4-(4-nitrobenzoyl-2,3,5,6-d$_4$)-5,6-dihydro-4H-dithieno[3,2-b:2',3'-d]azepine-8-carboxamide

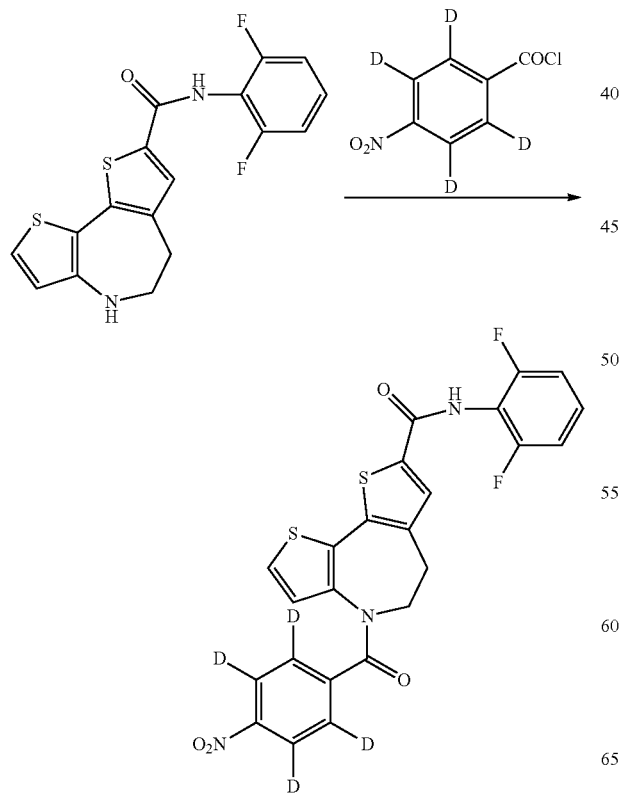

To a suspension of 4-nitrobenzoic-2,3,5,6-d$_4$ acid (500 mg, 2.92 mmol) in DCM (5.0 mL) was added oxalyl chloride (1.28 mL, 14.6 mmol) and one drop of DMF. This mixture was stirred at RT for 1 hr and was then evaporated in vacuo. The residue was taken up into DCM (5.0 mL) and was added to a solution of N-(2,6-difluorophenyl)-5,6-dihydro-4H-dithieno[3,2-b:2',3'-d]azepine-8-carboxamide (1.06 g, 2.92 mmol) in pyridine (3.0 mL) and after stirring at RT for 1 hr the mixture was evaporated in vacuo. The residue was taken up into a mixture of DCM and MeOH (9:1, 50 mL) and was washed with water (2×30 mL) and with brine (3×50 mL) and then evaporated in vacuo. The resulting residue was purified by flash column chromatography (SiO$_2$, 80 g, 0-60% EtOAc in isohexane, gradient elution) to afford the title compound as a yellow solid (678 mg, 45% yield, 92% pure by HPLC); R$^t$ 2.44 min (Method 1a); m/z 516 (M+H)$^+$ (ES$^+$). This material was used in the subsequent step without additional purification.

N-(2,6-Difluorophenyl)-4-(2-fluoro-4-nitrobenzoyl)-5,6-dihydro-4H-dithieno[3,2-b:2',3'-d]azepine-8-carboxamide

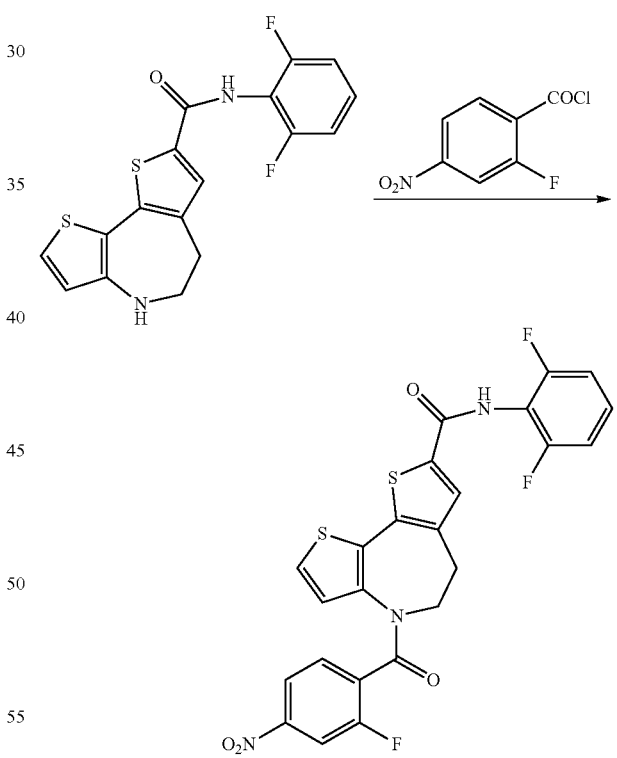

To a suspension of 2-fluoro-4-nitrobenzoic acid (392 mg, 2.12 mmol) in toluene (5.0 mL) was added thionyl chloride (309 µL, 4.24 mmol) followed by two drops of DMF. The mixture was heated at reflux for 2 hr, then cooled to RT and evaporated in vacuo. The resulting residue was taken up into MeCN (5.0 mL) and was added to a solution of N-(2,6-difluorophenyl)-5,6-dihydro-4H-dithieno[3,2-b:2',3'-d]azepine-8-carboxamide (512 mg, 1.41 mmol) in pyridine (5.0 mL). After stirring at RT for 18 hr the mixture was evaporated in vacuo and the residue was triturated with water (60 mL). The resulting solid was collected by filtration and purified by flash column chromatography (SiO$_2$, 24 g, 0-5% MeOH in DCM, gradient elution) to afford the title compound as a dark orange solid (619 mg, 83% yield, 93% pure by HPLC); R$^t$ 2.34 min (Method 1a); m/z 530 (M+H)$^+$ (ES$^+$). This material was used in the subsequent step without additional purification.

4-(4-Aminobenzoyl)-N-(2,6-difluorophenyl)-5,6-dihydro-4H-dithieno[3,2-b:2',3'-d]azepine-8-carboxamide

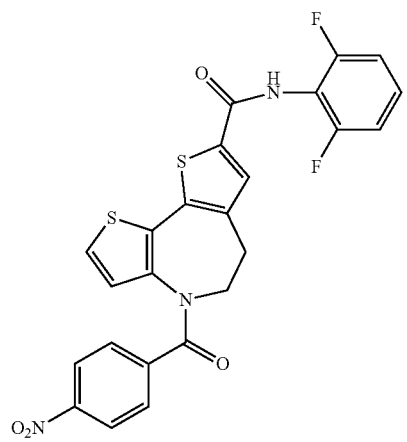

To a solution of N-(2,6-difluorophenyl)-4-(4-nitrobenzoyl)-5,6-dihydro-4H-dithieno[3,2-b:2',3'-d]azepine-8-carboxamide (944 mg, 1.85 mmol) in IPA (20 mL) was added sat aq NH$_4$Cl (2.0 mL) and iron powder (515 mg, 9.23 mmol). The resulting mixture was stirred at 80° C. for 2 hr, and was then filtered through celite whilst still hot. The celite pad was washed with MeOH (2×20 mL) and the combined filtrates evaporated in vacuo. The residue was partitioned between DCM (20 mL) and water (20 mL) and was passed through a phase separator. The organics were evaporated in vacuo to afford the title compound as a pale yellow solid (880 mg, 82% pure by $^1$H NMR); R$^t$2.11 min (Method 1a); m/z 482 (M+H)$^+$ (ES$^+$). The major impurity present in the product was identified as N,N-dimethylisobutyramide and the material was used in the subsequent step without additional purification.

4-(4-Aminobenzoyl-2,3,5,6-d$_4$)-N-(2,6-difluorophenyl)-5,6-dihydro-4H-dithieno[3,2-b: 2',3'-d]azepine-8-carboxamide

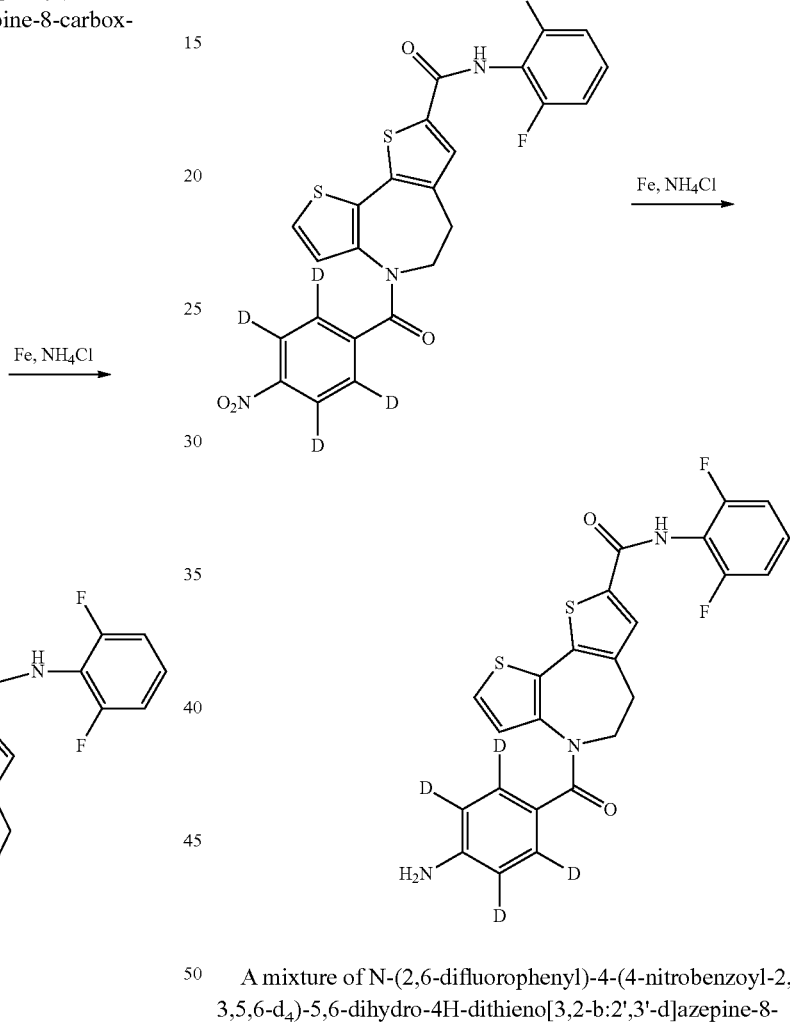

A mixture of N-(2,6-difluorophenyl)-4-(4-nitrobenzoyl-2,3,5,6-d$_4$)-5,6-dihydro-4H-dithieno[3,2-b:2',3'-d]azepine-8-carboxamide (678 mg, 1.32 mmol), iron powder (734 mg, 13.2 mmol) and NH$_4$Cl (703 mg, 13.2 mmol) in a mixture of EtOH (50 mL) and water (25 mL) was stirred at reflux for 2 hr and then filtered through celite (30 g). The celite pad was washed with hot EtOH (2×50 mL) and the combined filtrates were evaporated in vacuo. The residue was taken up into DCM (30 mL) and was washed with water (2×20 mL) and then dried and evaporated in vacuo to afford the title compound as a cream coloured solid (582 mg, 91% yield); R$^t$2.14 min (Method 1a); m/z 486 (M+H)$^+$ (ES$^+$); $^1$H NMR δ: 3.18 (2H, apparent t), 3.90-4.10 (2H, br), 5.63 (2H, br), 6.34 (1H, d), 7.19-7.26 (3H, over-lapping m), 7.38-7.46 (1H, m), 7.88 (1H, s), 10.22 (1H, s).

55
4-(4-Amino-2-fluorobenzoyl)-N-(2,6-difluorophenyl)-5,6-dihydro-4H-dithieno[3,2-b:2',3'-d]azepine-8-carboxamide

56
4-(4-(2-Chloro-5,6-dimethylnicotinamide)benzoyl)-N-(2,6-difluorophenyl)-5,6-dihydro-4H-dithieno[3,2-b:2',3'-d]azepine-8-carboxamide

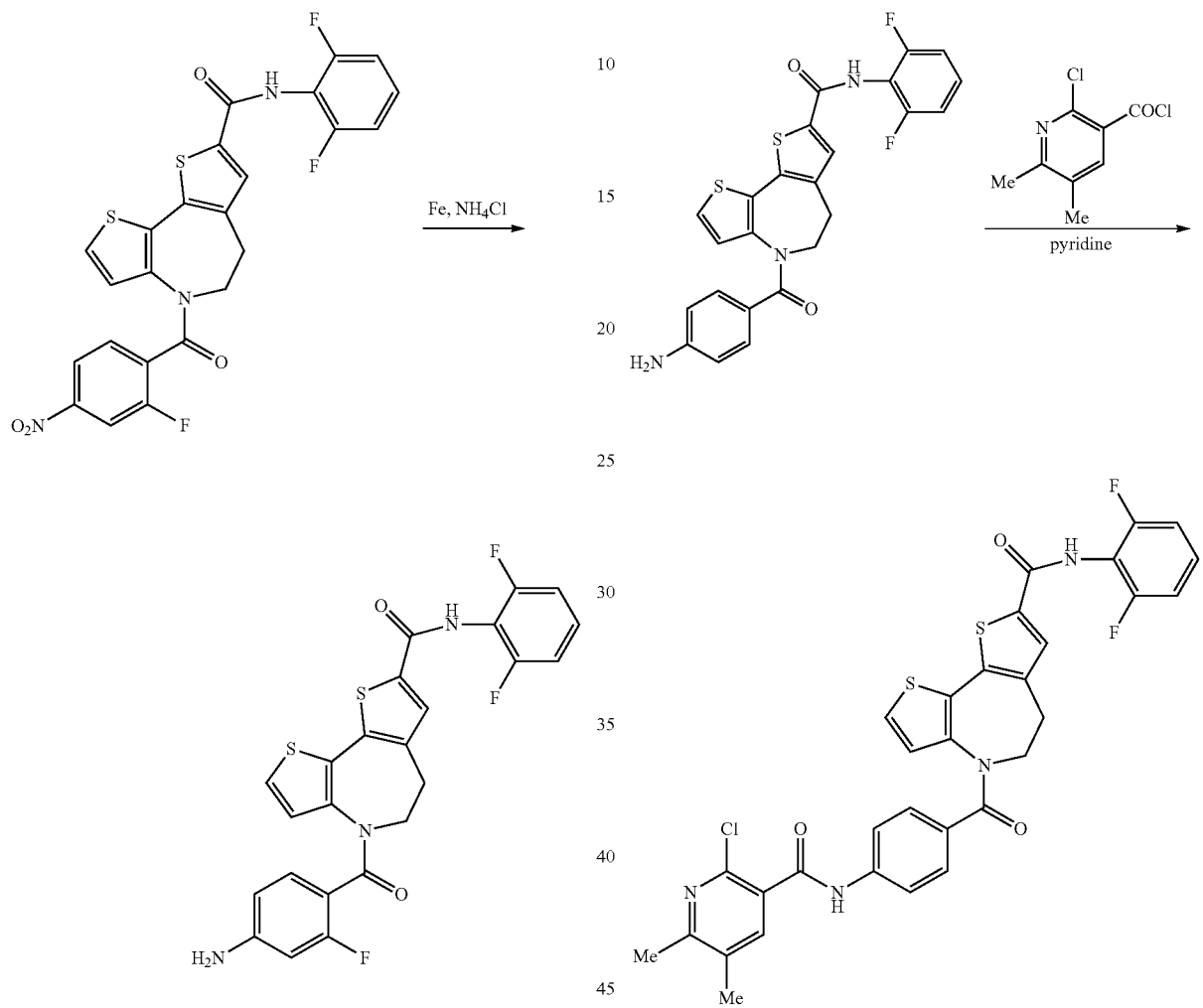

To a solution of N-(2,6-difluorophenyl)-4-(2-fluoro-4-nitrobenzoyl)-5,6-dihydro-4H-dithieno [3,2-b:2',3'-d]azepine-8-carboxamide (619 mg, 1.17 mmol) in IPA (10 mL) was added sat aq NH$_4$Cl (1.5 mL) and iron powder (326 mg, 5.85 mmol). The mixture was stirred at 80° C. for 3 hr, then cooled to RT and filtered through celite (10 g). The celite pad was washed with MeOH (400 mL) and the combined filtrates were evaporated in vacuo. The residue was triturated with water (60 mL) and the solid that formed was collected by filtration and dried to afford the title compound as a yellow solid (552 mg, 95% yield); R$^t$ 2.10 min (Method 1a); m/z 500 (M+H)$^+$(ES$^+$); $^1$H NMR δ: 3.17 (2H, apparent t), 3.80-4.10 (2H, br), 5.66-5.98 (2H, br), 6.10 (1H, dd), 6.32 (1H, dd), 6.40 (1H, br d), 6.99 (1H, t), 7.18-7.27 (3H, over-lapping m), 7.37-7.46 (1H, m), 7.86 (1H, s), 10.22 (1H, s).

To a suspension of 2-chloro-5,6-dimethylnicotinic acid (100 mg, 0.540 mmol) in DCM (4.0 mL) was added 1-chloro-N,N,2-trimethylprop-1-en-1-amine (71.4 μL, 0.540 mmol) and the reaction mixture stirred at RT for 15 min and then added to a solution of 4-(4-aminobenzoyl)-N-(2,6-difluorophenyl)-5,6-dihydro-4H-dithieno[3,2-b:2',3'-d]azepine-8-carboxamide (200 mg, 0.415 mmol) in pyridine (2.0 mL). After 1 hr at RT water (10 mL) was added and the biphasic mixture that formed was passed through a phase separator. The organics were evaporated in vacuo and the residue was purified by flash column chromatography (SiO$_2$, 24 g, 10-100% EtOAc in isohexane, gradient elution) to afford the title compound as a pale yellow solid (140 mg, 52% yield); R$^t$ 2.42 min (Method 1a); m/z 650 (M+H)$^+$ (ES$^+$).

4-(4-(2-Chloro-6-methylnicotinamido)-2-fluorobenzoyl)-N-(2,6-difluorophenyl)-5,6-dihydro-4H-dithieno[3,2-b:2',3'-d]azepine-8-carboxamide

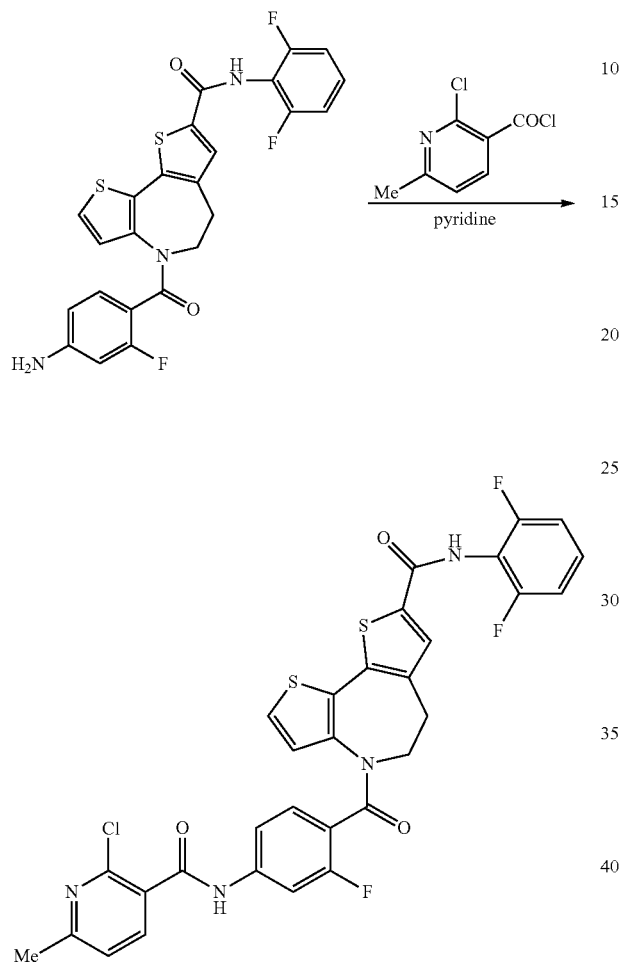

To a solution of 2-chloro-6-methylnicotinic acid (39 mg, 0.23 mmol) in DCM (1.0 mL) was added 1-chloro-N,N,2-trimethylprop-1-en-1-amine (50 μL, 0.38 mmol) and the resulting mixture stirred at RT for 1.5 hr and then treated with a solution of 4-(4-amino-2-fluoro benzoyl)-N-(2,6-difluorophenyl)-5,6-dihydro-4H-dithieno[3,2-b:2',3'-d]azepine-8-carboxamide (75 mg, 0.15 mmol) in pyridine (1.0 mL) The mixture was stirred at RT for 18 hr; water (5.0 mL) and DCM (5.0 mL) were added and the resulting biphasic mixture was passed through a phase separator. The organic phase was evaporated in vacuo and the residue thus obtained was triturated with water (10 mL). The precipitate that formed was collected by filtration and dried in vacuo to afforded the title compound (87 mg, 89% yield); R'2.26 min (Method 1a); m/z 653 (M+H)$^+$ (ES$^+$); $^1$H NMR δ: 2.51 (assume 3H, obscured by solvent), 3.18-3.32 (2H, br), 3.60-4.30 (2H, br), 6.31-6.49 (1H, br), 7.19-7.31 (3H, over-lapping m), 7.36-7.58 (5H, over-lapping m), 7.89 (1H, s), 7.99 (1H, d), 10.25 (1H, s), 10.91 (1H, s).

Preparation of Compound Examples of the Invention

Example 1

N-(2,6-Difluorophenyl)-4-(4-(5-methyl-2-(7-oxa-2-azaspiro[3.5]nonan-2-yl) nicotinamido)benzoyl)-5,6-dihydro-4H-dithieno[3,2-b:2',3'-d]azepine-8-carboxamide

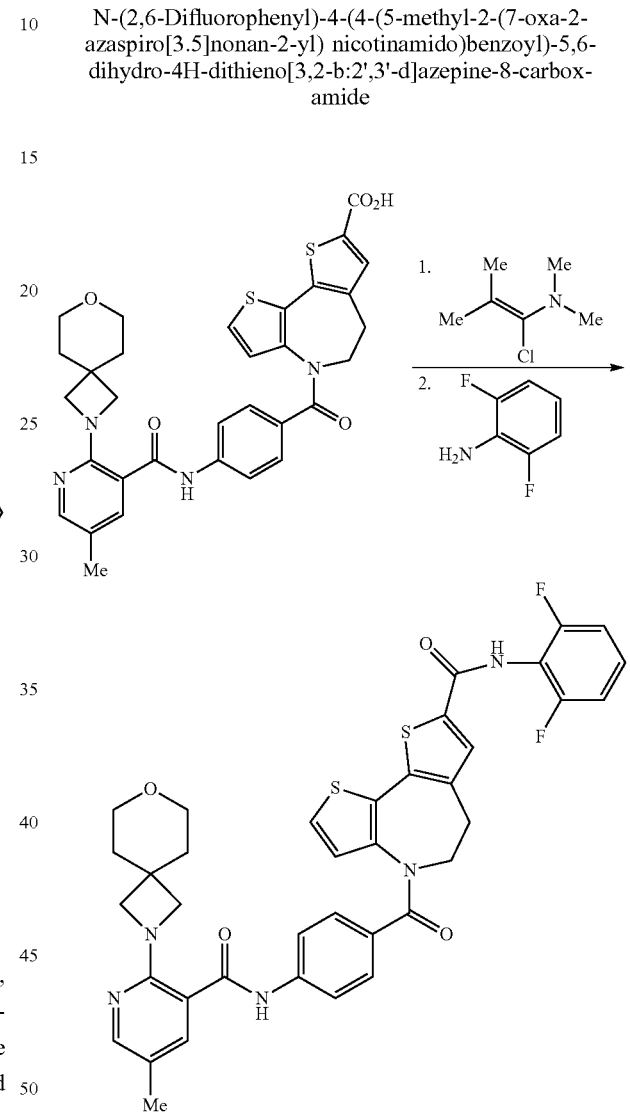

To a solution of 4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxylic acid (100 mg, 0.163 mmol) in DCM (2.0 mL) was added 1-chloro-N,N,2-trimethylprop-1-en-1-amine (64.4 μL, 0.488 mmol). After 30 min at RT the resulting mixture was added to a solution of 2,6-difluoroaniline (52.5 μL, 0.488 mmol) in pyridine (0.5 mL) and maintained at RT for a further 30 min. Water (3.0 mL) was added and the resulting biphasic mixture was passed through a phase separator. The organic phase was evaporated in vacuo and the residue was purified by flash column chromatography (SiO$_2$, 12 g, 0-10% MeOH in DCM, gradient elution). The solid thus obtained was triturated with MeCN (10 mL), collected by filtration and dried in vacuo to afford the title compound, Example 1, as a white solid (102 mg, 86% yield); R$^r$ 1.89 min (Method 1a); m/z 726 (M+H)$^+$ (ES$^+$); $^1$H NMR δ: 1.64 (4H, br t), 2.18 (3H, s), 3.24 (2H, apparent t), 3.47 (4H, br t), 3.64 (4H, s), 3.75-4.28 (2H, br), 6.41 (1H, br d), 7.19-7.28 (5H, over-lapping m), 7.39-7.46 (1H, m), 7.53 (1H, apparent d), 7.65 (2H, d), 7.90 (1H, s), 8.06 (1H, dd), 10.25 (1H, s), 10.47 (1H, s).

Example 2

4-(4-(2-(7-Oxa-2-azaspiro[3.5]nonan-2-yl)-6,7-di-hydro-5H-cyclopenta[b]pyridine-3-carboxamido) benzoyl)-N-(2,6-difluorophenyl)-5,6-dihydro-4H-dithieno[3,2-b: 2',3'-d]azepine-8-carboxamide

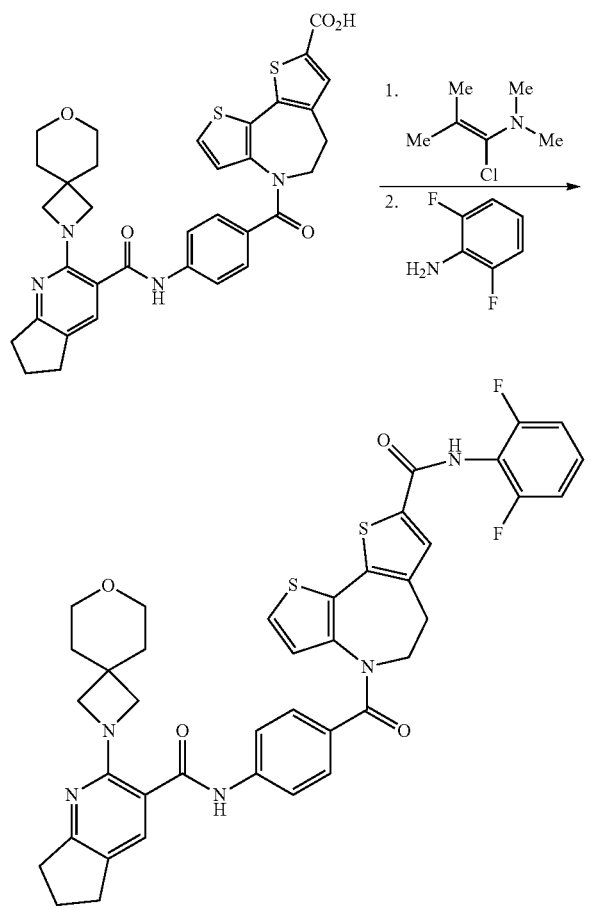

To a solution in DCM (2.0 mL) of 4-(4-(2-(7-oxa-2-azaspiro[3.5]nonan-2-yl)-6,7-dihydro-5H-cyclopenta[b]pyridine-3-carboxamido)benz yl)-5,6-dihydro-4H-dithieno[3,2-b:2',3'-d]azepine-8-carboxylic acid (100 mg, 0.156 mmol) was added 1-chloro-N,N,2-trimethylprop-1-en-1-amine (61.9 μL, 0.468 mmol) and after 30 min at RT the mixture added to a solution of 2,6-difluoroaniline (50.4 μL, 0.468 mmol) in pyridine (0.5 mS). The reaction mixture was kept at RT for a further 30 min and was then treated with water (3.0 mL). The resulting biphasic mixture was passed through a phase separator, the organics were evaporated in vacuo and the residue was purified by preparative HPLC (Method 1) to afford the title compound, Example 2, as a pale yellow solid (32 mg, 27% yield); R$^r$ 1.99 min (Method 1a); m/z 752 (M+H)$^+$ (ES$^+$); $^1$H NMR δ: 1.64 (4H, br t), 2.02 (2H, p), 2.78 (4H, t), 3.24 (2H, apparent t), 3.48 (4H, br t), 3.64 (4H, s), 3.80-4.22 (2H, br), 6.40 (1H, d), 7.19-7.28 (5H, over-lapping m), 7.38-7.46 (1H, m), 7.52 (1H, s), 7.64 (2H, d), 7.90 (1H, s), 10.26 (1H, s), 10.38 (1H, s).

Example 3

N-(2,6-difluorophenyl)-4-(4-(5-methyl-2-(7-oxa-2-azaspiro[3.5]nonan-2-yl) nicotinamido)benz-y-2,3,5,6-d4)-5,6-dihydro-4H-dithieno[3,2-b:2',3'-d]azepine-8-carboxamide

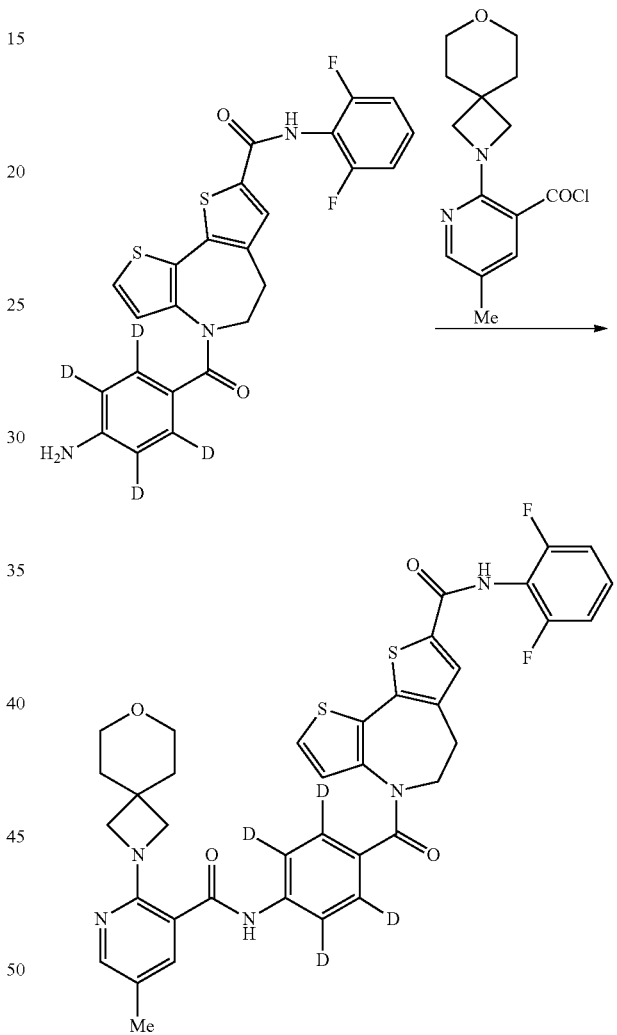

To a solution of 5-methyl-2-(7-oxa-2-azaspiro[3.5]nonan-2-yl)nicotinic acid (170 mg, 0.649 mmol) in DCM (5.0 mg, 0.156 mmol) was added 1-chloro-N,N,2-trimethylprop-1-en-1-amine (82.0 μL, 0.618 mmol) and the resulting mixture stirred at RT for 15 min. This mixture was then added to a solution of 4-(4-aminobenzoyl-2,3,5,6-d$_4$)-N-(2,6-difluorophenyl)-5,6-dihydro-4H-dithieno [3,2-b:2',3'-d]azepine-8-carboxamide (300 mg, 0.618 mmol) in pyridine (2.0 mL) and stirred at RT for a further 30 min before being evaporated in vacuo. The residue thus obtained was taken up into a mixture of DCM and MeOH (9:1, 20 mL), and was washed with water (20 mL) and with brine (2×10 mL), then dried and evaporated in vacuo. Purification of the residue by flash column chromatography (SiO$_2$, 24 g, 0-5% MeOH in DCM, gradient elution) afforded the title compound as a light yellow solid (379 mg, 84% yield); R$^t$ 1.87 min (Method 1a); m/z 730 (M+H)$^+$ (ES$^+$); $^1$H NMR δ: 1.64 (4H, br t), 2.19 (3H, s), 3.24 (2H, apparent t), 3.47 (4H, br t), 3.64 (4H, s), 3.82-4.26 (2H, br), 6.40 (1H, br d), 7.19-7.28 (3H, over-lapping m), 7.39-7.45 (1H, m), 7.53 (1H, dd), 7.90 (1H, s), 8.06 (1H, dd), 10.25 (1H, s), 10.47 (1H, s).

Example 4

N-(2,6-Difluorophenyl)-4-(4-(5,6-dimethyl-2-(7-oxa-2-azaspiro[3.5]nonan-2-yl)nicotinamido)benzoyl)-5,6-dihydro-4H-dithieno[3,2-b:2',3'-d]azepine-8-carboxamide

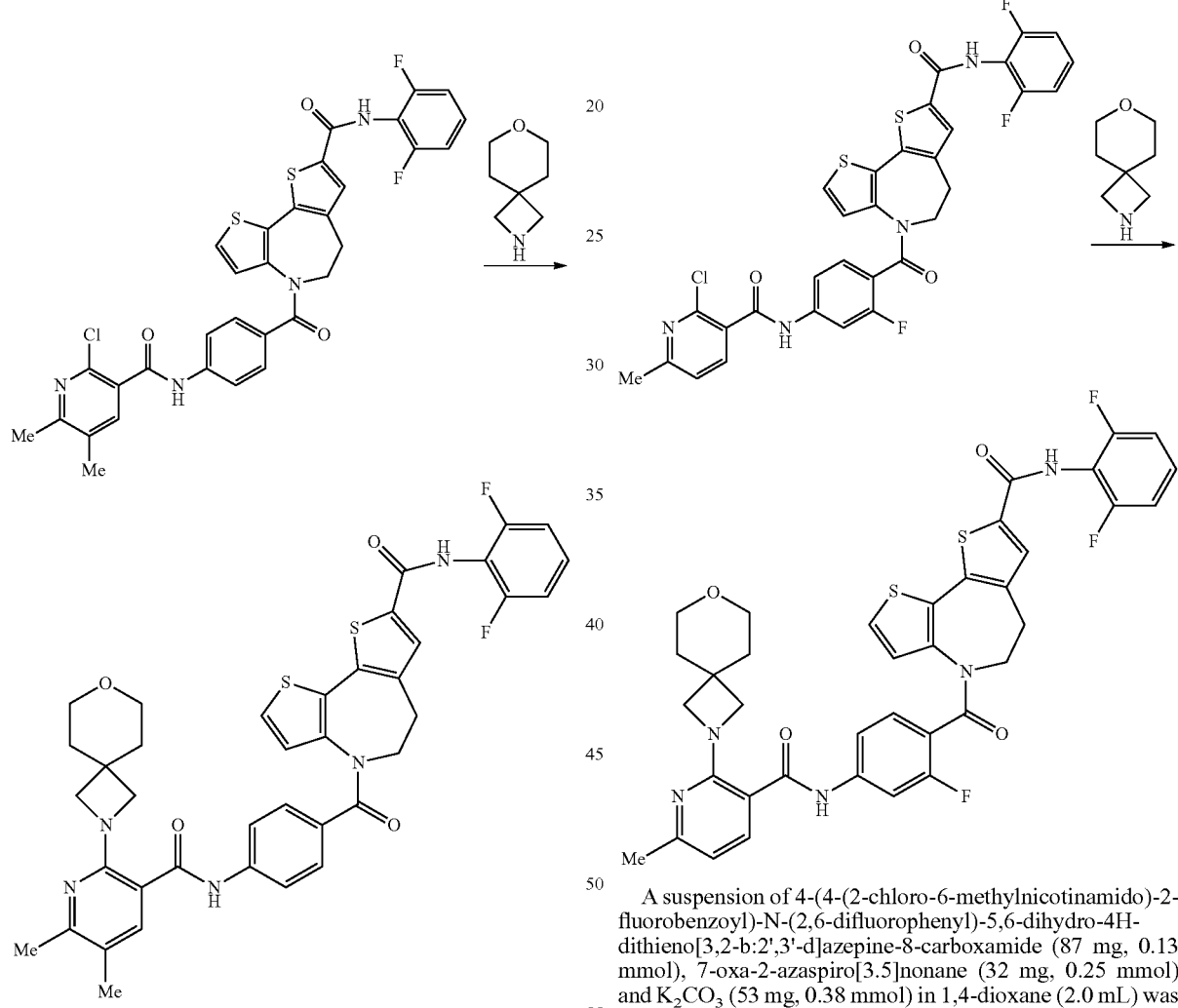

A suspension of 4-(4-(2-chloro-5,6-dimethylnicotinamido)benzoyl)-N-(2,6-difluorophenyl)-5,6-dihydro-4H-dithieno[3,2-b:2',3'-d]azepine-8-carboxamide (140 mg, 0.216 mmol), 7-oxa-2-aza spiro[3.5]nonane (82.0 mg, 0.647 mmol) and K$_2$CO$_3$ (179 mg, 1.29 mmol) in NMP (10.0 mL) was heated at 140° C. for 2 hr. After cooling to RT the reaction mixture was partitioned between water (20 mL) and EtOAc (20 mL) and was passed through a phase separator. The organics were evaporated in vacuo and the resulting yellow oil purified by flash column chromatography (SiO$_2$, 12 g, 0-10% MeOH in DCM, gradient elution) to afford the title compound, Example 4, as a pale yellow solid (82 mg, 51% yield); R$^t$ 1.86 min (Method 1a); m/z 740 (M+H)$^+$ (ES$^+$); $^1$H NMR δ: 1.63 (4H, br t), 2.15 (3H, s), 2.31 (3H, s), 3.24 (2H, apparent t), 3.48 (4H, br t), 3.63 (4H, s), 3.78-4.18 (2H, br), 6.40 (1H, d), 7.19-7.29 (5H, over-lapping m), 7.38-7.47 (2H, over-lapping m), 7.64 (2H, d), 7.90 (1H, s), 10.24 (1H, s), 10.36 (1H, s).

Example 5

N-(2,6-Difluorophenyl)-4-(2-fluoro-4-(6-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide

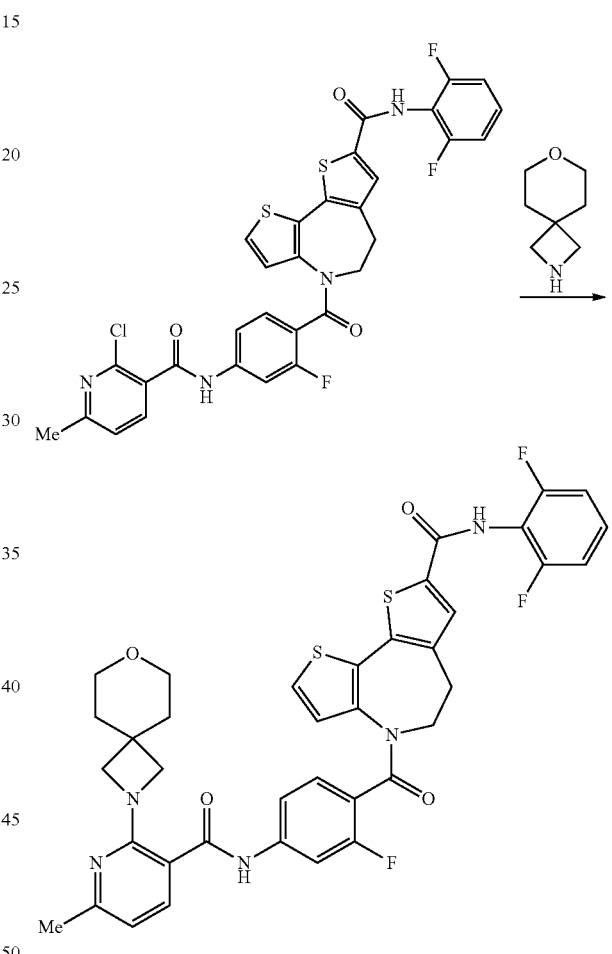

A suspension of 4-(4-(2-chloro-6-methylnicotinamido)-2-fluorobenzoyl)-N-(2,6-difluorophenyl)-5,6-dihydro-4H-dithieno[3,2-b:2',3'-d]azepine-8-carboxamide (87 mg, 0.13 mmol), 7-oxa-2-azaspiro[3.5]nonane (32 mg, 0.25 mmol) and K$_2$CO$_3$ (53 mg, 0.38 mmol) in 1,4-dioxane (2.0 mL) was heated at 80° C. for 3 hr. After cooling to RT the solvent was evaporated in vacuo and the residue was triturated with water (10.0 mL). The resulting precipitate was collected by filtration and was purified by flash column chromatography (SiO$_2$, 4 g, 0-50% THF in DCM, gradient elution) and then by preparative HPLC (Method 4) to afford the title compound, Example 5, as an off-white solid (28 mg, 30% yield); R$^t$ 1.91 min (Method 1a); m/z 744 (M+H)$^+$ (ES$^+$); $^1$H NMR δ: 1.65 (4H, br t), 2.34 (3H, s), 3.18-3.30 (2H, br), 3.49 (4H, br t), 3.66 (4H, s), 3.66-4.23 (2H, br), 6.33-6.48 (1H, br), 6.60 (1H, d), 7.19-7.29 (3H, over-lapping m), 7.33-7.60 (4H, over-lapping m), 7.59 (1H, d), 7.89 (1H, s), 10.25 (1H, s), 10.54 (1H, s).

TABLE 2

Additional Compound Examples of the Invention

Structure, Example No., Name, Preparative HPLC or Column Chromatography
Purification Method (where emloyed), LC-MS Analysis and ¹HNMR Spectral Data

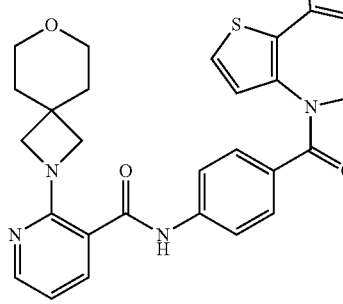

6: 4-(4-(2-(7-oxa-2-azaspiro[3.5]nonan-2-yl)nicotin-amido)benzoyl)-N-(2,6-difluorophenyl)-5,6-dihydro-4H-dithieno[3,2-b:2',3'-d]azepine-8-carboxamide.
Flash column chromatography (SiO$_2$, 12 g, 0-5% MeOH in DCM, gradient elution);
R$^t$ 1.86 min (Method 1a); m/z 712 (M + H)$^+$ (ES$^+$);
¹H NMR δ: 1.65 (4H, br t), 3.24 (2H, apparent t), 3.48 (4H, br t), 3.68 (4H, s), 3.80-4.18 (2H, br), 6.41 (1H, br d), 6.73 (1H, dd), 7.20-7.29 (5H, over-lapping m), 7.39-7.46 (1H, m), 7.62-7.68 (3H, over-lapping m), 7.90 (1H, s), 8.20 (1H, dd), 10.25 (1H, s), 10.49 (1H, s).

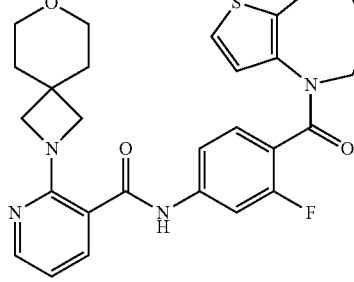

7: 4-(4-(2-(7-oxa-2-azaspiro[3.5]nonan-2-yl)nicotinamido)-2-fluorobenzoyl)-N-(2,6-difluorophenyl)-5,6-dihydro-4H-dithieno[3,2-b:2',3'-d]azepine-8-carboxamide.
Flash column chromatography (SiO$_2$, 4 g, 0-50% THF in DCM, gradient elution) then prep HPLC, Method 4;
R$^t$ 1.93 min (Method 1a); m/z 730 (M + H)$^+$ (ES$^+$);
¹H NMR δ: 1.66 (4H, br t), 3.19-3.29 (2H, br), 3.49 (4H, br t), 3.67 (4H, s), 3.73-4.23 (2H, br), 6.34-6.50 (1H, br), 6.74 (1H, dd), 7.19-7.30 (3H, over-lapping m), 7.35-7.65 (4H, over-lapping m), 7.69 (1H, dd), 7.89 (1H, s), 8.21 (1H, dd), 10.25 (1H, s), 10.65 (1H, s).

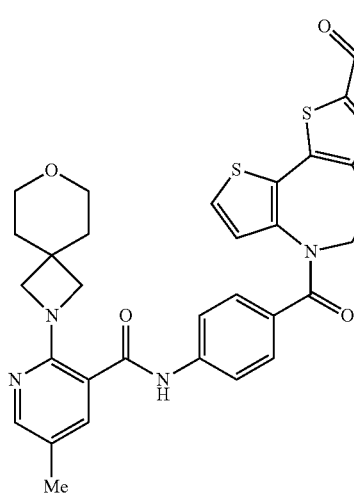

8: 4-(4-(5-methyl-2-(7-oxa-2-azaspiro[3.5]nonan-2-yl)nicotinamido)benzoyl)-N-phenyl-5,6-dihydro-4H-dithieno[3,2-b:2',3'-d]azepine-8-carboxamide.
Prep HPLC Method 1;
R$^t$ 1.96 min (Method 1a); m/z 690 (M + H)$^+$ (ES$^+$);
¹H NMR δ: 1.64 (4H, br t), 2.18 (3H, s), 3.24 (2H, apparent t), 3.47 (4H, br t), 3.63 (4H, s), 3.80-4.22 (2H, br), 6.39 (1H, d), 7.11 (1H, apparent tt), 7.21-7.28 (3H, over-lapping m), 7.33-7.39 (2H, m), 7.53 (1H, d), 7.64 (2H, d), 7.74 (2H, apparent dd), 7.94 (1H, s), 8.05 (1H, dd), 10.28 (1H, s), 10.48 (1H, s).

TABLE 2-continued

Additional Compound Examples of the Invention

Structure, Example No., Name, Preparative HPLC or Column Chromatography Purification Method (where emloyed), LC-MS Analysis and $^1$HNMR Spectral Data 9: N-(2-fluorophenyl)-4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide.
Flash column chromatography (SiO$_2$, 12 g, 0-10% MeOH in DCM, gradient elution);
R$^t$ 1.98 min (Method 1a); m/z 708 (M + H)$^+$ (ES$^+$);
$^1$H NMR δ: 1.64 (4H, br t), 2.19 (3H, s), 3.23 (2H, apparent t), 3.47 (4H, br t), 3.64 (4H, s), 3.80-4.23 (2H, br), 6.40 (1H, d), 7.21-7.34 (6H, over-lapping m), 7.54 (1H, br s), 7.59 (1H, td), 7.64 (2H, d), 7.92 (1H, s), 8.05 (1H, dd), 10.20 (1H, s), 10.48 (1H, s).

10: N-(2,4-difluorophenyl)-4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide.
Flash column chromatography (SiO$_2$, 12 g, 0-10% MeOH in DCM, gradient elution);
R$^t$ 2.00 min (Method 1a); m/z 726 (M + H)$^+$ (ES$^+$);
$^1$H NMR δ: 1.64 (4H, br t), 2.19 (3H, s), 3.23 (2H, apparent t), 3.47 (4H, br t), 3.64 (4H, s), 3.80-4.23 (2H, br), 6.40 (1H, br d), 7.10-7.17 (1H, m), 7.22-7.28 (3H, over-lapping m), 7.34-7.42 (1H, m), 7.52-7.62 (2H, over-lapping m), 7.64 (2H, d), 7.90 (1H, s), 8.05 (1H, dd), 10.22 (1H, s), 10.48 (1H, s).

11: N-(2-fluoro-6-methylphenyl)-4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide.
Flash column chromatography (SiO$_2$, 12 g, 0-5% MeOH in DCM, gradient elution);
R$^t$ 1.94 min (Method 1a); m/z 722 (M + H)$^+$ (ES$^+$);
$^1$H NMR δ: 1.64 (4H, br t), 2.19 (3H, s), 2.24 (3H, s), 3.24 (2H, apparent t), 3.47 (4H, br t), 3.64 (4H, s), 3.76-4.29 (2H, br), 6.40 (1H, br d), 7.10-7.17 (2H, over-lapping m), 7.21-7.30 (4H, over-lapping m), 7.53 (1H, br d), 7.64 (2H, d), 7.89 (1H, s), 8.06 (1H, dd), 10.00 (1H, s), 10.47 (1H, s).

TABLE 2-continued

Additional Compound Examples of the Invention

Structure, Example No., Name, Preparative HPLC or Column Chromatography
Purification Method (where emloyed), LC-MS Analysis and ¹HNMR Spectral Data

12: N-(2-chloro-6-fluorophenyl)-4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide.
Flash column chromatography (SiO₂, 12 g, 0-5% MeOH in DCM, gradient elution);
R$^t$ 1.98 min (Method 1a); m/z 742 (M + H)⁺ (ES⁺);
¹H NMR δ: 1.64 (4H, br t), 2.19 (3H, s), 3.24 (2H, apparent t), 3.47 (4H, br t), 3.64 (4H, s), 3.78-4.27 (2H, br), 6.40 (1H, br d), 7.22-7.28 (3H, over-lapping m), 7.34-7.48 (3H, over-lapping m), 7.53 (1H, d), 7.64 (2H, d), 7.91 (1H, s), 8.06 (1H, dd), 10.28 (1H, s), 10.46 (1H, s).

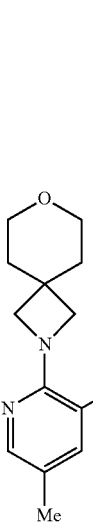

13: N-(2,6-dichlorophenyl)-4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide.
Flash column chromatography (SiO₂, 12 g, 0-5% MeOH in DCM, gradient elution);
R$^t$ 2.01 min (Method 1a); m/z 758 (M + H)⁺ (ES⁺);
¹H NMR δ: 1.64 (4H, br t), 2.19 (3H, s), 3.24 (2H, apparent t), 3.47 (4H, br t), 3.64 (4H, s), 3.80-4.23 (2H, br), 6.40 (1H, br d), 7.23-7.29 (3H, over-lapping m), 7.41 (1H, apparent dd), 7.53 (1H, d), 7.60 (2H, d), 7.64 (2H, d), 7.91 (1H, s), 8.06 (1H, dd), 10.40 (1H, s), 10.46 (1H, s).

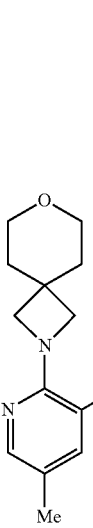

14: N-(2-cyano-6-fluorophenyl)-4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide.
Flash column chromatography (SiO₂, 12 g, 0-10% MeOH in DCM, gradient elution);
R$^t$ 1.82 min (Method 1a); m/z 733 (M + H)⁺ (ES⁺);
¹H NMR δ: 1.64 (4H, br t), 2.19 (3H, s), 3.24 (2H, apparent t), 3.47 (4H, br t), 3.64 (4H, s), 3.80-4.23 (2H, br), 6.41 (1H, d), 7.23-7.30 (3H, over-lapping m), 7.53 (1H, d), 7.56-7.61 (1H, m), 7.64 (2H, d), 7.74-7.82 (2H, over-lapping m), 7.94 (1H, s), 8.05 (1H, dd), 10.47 (1H, s), 10.73 (1H, s).

TABLE 2-continued

Additional Compound Examples of the Invention

Structure, Example No., Name, Preparative HPLC or Column Chromatography Purification Method (where emloyed), LC-MS Analysis and ¹HNMR Spectral Data 15: N-(2-fluoro-6-hydroxyphenyl)-4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide.
Prep HPLC Method 1;
R$^t$ 1.79 min (Method 1a); m/z 724 (M + H)$^+$ (ES$^+$);
¹H NMR δ: 1.64 (4H, br t), 2.18 (3H, s), 3.22 (2H, apparent t), 3.47 (4H, br t), 3.63 (4H, s), 3.78-4.29 (2H, br), 6.40 (1H, d), 6.67-6.78 (2H, over-lapping m), 7.11-7.17 (1H, m), 7.21-7.27 (3H, over-lapping m), 7.53 (1H, d), 7.64 (2H, d), 7.88 (1H, s), 8.05 (1H, dd), 9.75 (1H, br s), 10.00-10.23 (1H, br), 10.47 (1H, s).

16: N-(2-fluoro-6-methoxyphenyl)-4-(4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide.
Flash column chromatography (SiO$_2$, 12 g, 0-10% MeOH in DCM, gradient elution);
R$^t$ 1.85 min (Method 1a); m/z 738 (M + H)$^+$ (ES$^+$);
¹H NMR δ: 1.64 (4H, br t), 2.18 (3H, s), 3.22 (2H, apparent t), 3.47 (4H, br t), 3.64 (4H, s), 3.82 (3H, s), 3.85-4.20 (2H, br), 6.40 (1H, d), 6.90 (1H, apparent t), 6.96 (1H, apparent d), 7.21-7.27 (3H, over-lapping m), 7.30-7.36 (1H, m), 7.53 (1H, d), 7.64 (2H, d), 7.88 (1H, s), 8.05 (1H, dd), 9.82 (1H, s), 10.46 (1H, s).

17: 4-(4-(5-methyl-2-(7-oxa-2-azaspiro[3.5]nonan-2-yl)nicotinamido)benzoyl)-N-(2,4,6-trifluorophenyl)-5,6-dihydro-4H-dithieno[3,2-b:2',3'-d]azepine-8-carboxamide.
Flash column chromatography (SiO$_2$, 12 g, 0-10% MeOH in DCM, gradient elution);
R$^t$ 1.93 min (Method 1a); m/z 744 (M + H)$^+$ (ES$^+$);
¹H NMR δ: 1.64 (4H, br t), 2.18 (3H, s), 3.24 (2H, apparent t), 3.47 (4H, br t), 3.64 (4H, s), 3.80-4.24 (2H, br), 6.40 (1H, d), 7.22-7.28 (3H, over-lapping m), 7.32-7.40 (2H, over-lapping m), 7.53 (1H, d), 7.64 (2H, d), 7.89 (1H, s), 8.05 (1H, dd), 10.22 (1H, s), 10.47 (1H, s).

TABLE 2-continued

Additional Compound Examples of the Invention

Structure, Example No., Name, Preparative HPLC or Column Chromatography
Purification Method (where emloyed), LC-MS Analysis and ¹HNMR Spectral Data

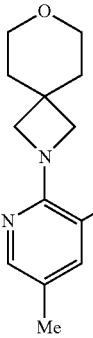

18: N-(2,6-difluorophenyl)-4-(2-fluoro-4-(5-methyl-2-(7-oxa-2-azaspiro[3.5]nonan-2-yl)nicotinamido)benzoyl)-5,6 dihydro-4H-dithieno[3,2-b:2',3'-d]azepine-8-carboxamide.
Flash column chromatography (SiO₂, 12 g, 0-100% EtOAc in isohexane, gradient elution);
R$^t$ 2.37 min (Method 1b); m/z 744 (M + H)⁺ (ES⁺);
¹H NMR δ: 1.65 (4H, br t), 2.19 (3H, s), 3.18-3.30 (2H, br), 3.48 (4H, br t), 3.63 (4H, s), 3.80-4.23 (2H, br), 6.33-6.46 (1H, br), 7.18-7.28 (3H, over-lapping m), 7.35-7.58 (5H, over-lapping m), 7.89 (1H, s), 8.07 (1H, dd), 10.25 (1H, s), 10.62 (1H, s).

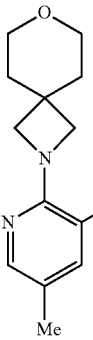

19: N-(2-chloro-6-fluorophenyl)-4-(2-fluoro-4-(5-methyl-2-(7-oxa-2-azaspiro[3.5]nonan-2-yl)nicotinamido)benzoyl)-5,6-dihydro-4H-dithieno[3,2-b:2',3'-d]azepine-8-carboxamide.
R$^t$ 2.41 min (Method 1b); m/z 760 (M + H)⁺ (ES⁺);
¹H NMR δ: 1.65 (4H, br t), 2.19 (3H, s), 3.19-3.29 (assume 2H, obscured by solvent), 3.48 (4H, br t), 3.64 (4H, s), 3.78-4.15 (2H, br), 6.30-6.55 (1H, br), 7.21-7.31 (1H, br), 7.33-7.60 (7H, over-lapping m), 7.89 (1H, s), 8.07 (1H, dd), 10.25 (1H, s), 10.59 (1H, s).

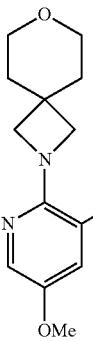

20: N-(2,6-difluorophenyl)-4-(4-(5-methoxy-2-(7-oxa-2-azaspiro[3.5]nonan-2-yl)nicotinamido)benzoyl)-5,6-dihydro-4H-dithieno[3,2-b:2',3'-d]azepine-8-carboxamide.
R$^t$ 2.17 min (Method 1a); m/z 742 (M + H)⁺ (ES⁺);
¹H NMR δ: 1.64 (4H, br t), 3.24 (2H, apparent t), 3.47 (4H, br t), 3.61 (4H, s), 3.76 (3H, s), 3.83-4.22 (2H, br), 6.40 (1H, d), 7.20-7.27 (5H, over-lapping m), 7.39-7.46 (2H, over-lapping m), 7.65 (2H, d), 7.90 (1H, s), 8.01 (1H, d), 10.25 (1H, s), 10.50 (1H, s).

TABLE 2-continued

Additional Compound Examples of the Invention

Structure, Example No., Name, Preparative HPLC or Column Chromatography
Purification Method (where emloyed), LC-MS Analysis and ¹HNMR Spectral Data

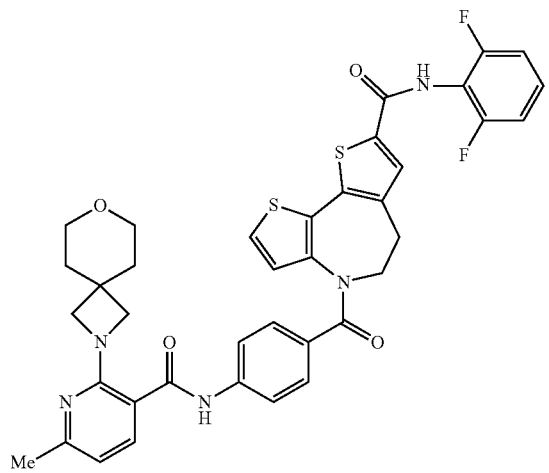 [SMILES: Cc1ccc(C(=O)Nc2ccc(C(=O)N3CCc4cc(C(=O)Nc5c(F)cccc5F)sc4-c4sccc43)cc2)c(N2CC3(CCOCC3)C2)n1]

21: N-(2,6-difluorophenyl)-4-(4-(6-methyl-2-(7-oxa-2-azaspiro
[3.5]nonan-2-yl)nicotinamido)benzoyl)-5,6-dihydro-
4H-dithieno[3,2-b:2',3'-d]azepine-8-carboxamide.
Flash column chromatography (SiO$_2$, 12 g, 0-10% MeOH
in DCM, gradient elution);
R$^t$ 1.86 min (Method 1a); m/z 726 (M + H)$^+$ (ES$^+$);
¹H NMR δ: 1.64 (4H, br t), 2.34 (3H, s), 3.24 (2H,
apparent t), 3.48 (4H, br t), 3.66 (4H, s), 3.80-4.24 (2H,
br), 6.40 (1H, br d), 6.58 (1H, d), 7.19-7.29 (5H, over-
lapping m), 7.38-7.46 (1H, m), 7.57 (1H, d), 7.64 (2H, d),
7.90 (1H, s), 10.25 (1H, s), 10.39 (1H, s).

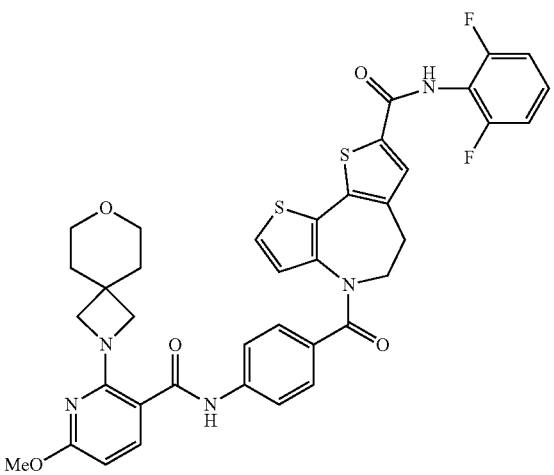 [SMILES: COc1ccc(C(=O)Nc2ccc(C(=O)N3CCc4cc(C(=O)Nc5c(F)cccc5F)sc4-c4sccc43)cc2)c(N2CC3(CCOCC3)C2)n1]

22: N-(2,6-difluorophenyl)-4-(4-(6-methoxy-2-(7-oxa-2-
azaspiro[3.5]nonan-2-yl)nicotinamido)benzoyl)-5,6-dihydro-
4H-dithieno[3,2-b:2',3'-d]azepine-8-carboxamide.
R$^t$ 2.55 min (Method 1a); m/z 742 (M + H)$^+$ (ES$^+$);
¹H NMR δ: 1.66 (4H, br t), 3.24 (2H, apparent t), 3.49 (4H,
br t), 3.70 (4H, s), 3.83 (3H, s), 3.86-4.22 (2H, br), 6.09
(1H, d), 6.40 (1H, br d), 7.19-7.27 (5H, over-lapping m),
7.39-7.46 (1H, m), 7.64 (3H, apparent t), 7.90 (1H, s),
10.25 (2H, s).

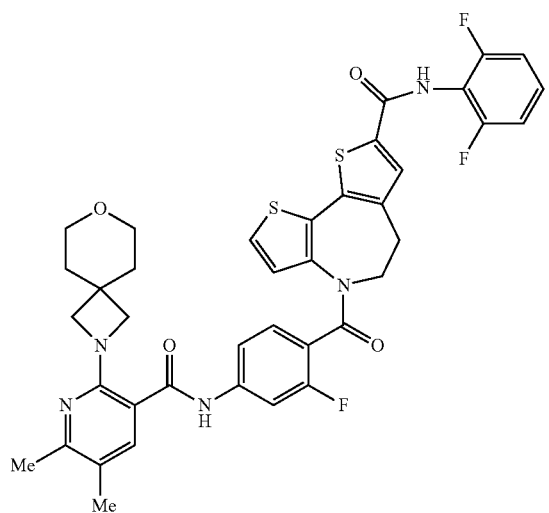 [SMILES: Cc1cc(C(=O)Nc2ccc(C(=O)N3CCc4cc(C(=O)Nc5c(F)cccc5F)sc4-c4sccc43)c(F)c2)c(N2CC3(CCOCC3)C2)nc1C]

23: N-(2,6-difluorophenyl)-4-(4-(5,6-dimethyl-2-(7-oxa-2-
azaspiro[3.5]nonan-2-yl)nicotinamido)-2-fluorobenzoyl)-
5,6-dihydro-4H-dithieno[3,2-b:2',3'-d]azepine-8-carboxamide.
Flash column chromatography (SiO$_2$, 4 g, 0-50% THF in
DCM, gradient elution) then prep HPLC Method 4;
R$^t$ 1.94 min (Method 1a); m/z 758 (M + H)$^+$ (ES$^+$);
¹H NMR δ: 1.65 (4H, br t), 2.15 (3H, s), 2.33 (3H, s), 3.18-
3.30 (2H, br), 3.49 (4H, br t), 3.65 (4H, s), 3.74-4.18 (2H,
br), 6.31-6.48 (1H, br), 7.19-7.29 (3H, over-lapping m),
7.32-7.60 (5H, over-lapping m), 7.89 (1H, s), 10.25 (1H,
s), 10.48-10.62 (1H, br).

TABLE 2-continued

Additional Compound Examples of the Invention

Structure, Example No., Name, Preparative HPLC or Column Chromatography
Purification Method (where emloyed), LC-MS Analysis and ¹HNMR Spectral Data 24: 4-(4-(2-(7-oxa-2-azaspiro[3.5]nonan-2-yl)-6,7-dihydro-5H-cyclopenta[b]pyridine-3-carboxamido)benzoyl)-N-(2-fluoro-6-methylphenyl)-5,6-dihydro-4H-dithieno[3,2-b:2',3'-d]azepine-8-carboxamide.
Prep HPLC Method 3;
$R^t$ 2.03 min (Method 1a); m/z 748 (M + H)⁺ (ES⁺);
¹H NMR δ: 1.64 (4H, br t), 2.02 (2H, p), 2.24 (3H, s), 2.78 (4H, t), 3.23 (2H, apparent t), 3.48 (4H, br t), 3.64 (4H, s), 3.80-4.24 (2H, br), 6.40 (1H, d), 7.10-7.17 (2H, overlapping m), 7.21-7.30 (4H, over-lapping m), 7.52 (1H, s), 7.64 (2H, d), 7.89 (1H, s), 10.02 (1H, s), 10.39 (1H, s).

25: N-(4-(8-((2,6-difluorophenyl)carbamoyl)-5,6-dihydro-4H-dithieno[3,2-b:2',3'-d]azepine-4-carbonyl)phenyl)-2-(7-oxa-2-azaspiro[3.5]nonan-2-yl)-7,8-dihydro-5H-pyrano[4,3-b]pyridine-3-carboxamide.
Flash column chromatography (SiO₂, 12 g, 50-100% EtOAc in isohexane, gradient elution);
$R^t$ 1.92 min (Method 1a); m/z 768 (M + H)⁺ (ES⁺);
¹H NMR δ: 1.64 (4H, br t), 2.73 (2H, br t), 3.24 (2H, apparent t), 3.48 (4H, br t), 3.65 (4H, s), 3.81-4.25 (assume 2H, br), 3.93 (2H, t), 4.59 (2H, s), 6.40 (1H, br d), 7.19-7.28 (5H, over-lapping m), 7.38-7.47 (2H, overlapping m), 7.63 (2H, d), 7.90 (1H, s), 10.25 (1H, s), 10.43 (1H, s).

26: N-(4-(8-((2-fluoro-6-methylphenyl)carbamoyl)-5,6-dihydro-4H-dithieno[3,2-b:2',3'-d]azepine-4-carbonyl)phenyl)-2-(7-oxa-2-azaspiro[3.5]nonan-2-yl)-7,8-dihydro-5H-pyrano[4,3-b]pyridine-3-carboxamide.
Flash column chromatography (SiO₂, 12 g, 50-100% EtOAc in isohexane, gradient elution) then prep HPLC Method 2;
$R^t$ 2.11 min (Method 1a); m/z 764 (M + H)⁺ (ES⁺);
¹H NMR δ: 1.64 (4H, br t), 2.33 (3H, s), 2.72 (2H, t), 3.22 (2H, apparent t), 3.48 (4H, br t), 3.65 (4H, s), 3.79-4.17 (2H, br), 3.93 (2H, t), 4.59 (2H, s), 6.39 (1H, br d), 7.03 (1H, apparent d), 7.14 (1H, apparent d), 7.20-7.27 (3H, over-lapping m), 7.39-7.46 (2H, over-lapping m), 7.63 (2H, d), 7.90 (1H, s), 10.11 (1H, s), 10.42 (1H, s).

TABLE 2-continued

Additional Compound Examples of the Invention

Structure, Example No., Name, Preparative HPLC or Column Chromatography Purification Method (where emloyed), LC-MS Analysis and ¹HNMR Spectral Data

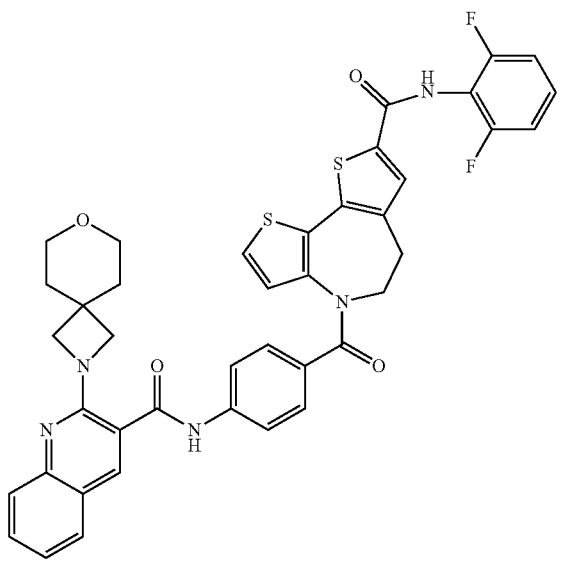 [SMILES: O=C(Nc1c(F)cccc1F)c1cc2c(s1)-c1sccc1N(C(=O)c1ccc(NC(=O)c3cc4ccccc4nc3N3CC4(CCOCC4)C3)cc1)CC2]

27: 4-(4-(2-(7-oxa-2-azaspiro[3.5]nonan-2-yl)quinoline-3-carboxamido)benzoyl)-N-(2,6-difluorophenyl)-5,6-dihydro-4H-dithieno[3,2-b:2',3'-d]azepine-8-carboxamide.
Flash column chromatography (SiO₂, 12 g, 0-10% MeOH in DCM, gradient elution);
R' 1.89 min (Method 1a); m/z 762 (M + H)⁺ (ES⁺);
¹H NMR δ: 1.68 (4H, br t), 3.25 (2H, apparent t), 3.51 (4H, br t), 3.82 (4H, s), 3.80-4.22 (2H, br), 6.42 (1H, br d), 7.19-7.32 (6H, over-lapping m), 7.39-7.46 (1H, m), 7.61 (2H, apparent d), 7.69 (2H, d), 7.81 (1H, d), 7.91 (1H, s), 8.26 (1H, s), 10.25 (1H, s), 10.75 (1H, s).

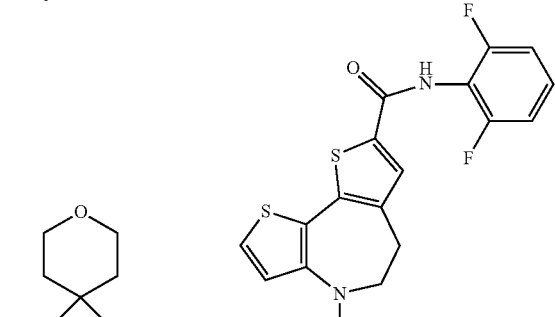

28: 4-(4-(5-(7-oxa-2-azaspiro[3.5]nonan-2-yl)thieno[3,2-b]pyridine-6-carboxamido)-2-fluorobenzoyl)-N-(2,6-difluorophenyl)-5,6-dihydro-4H-dithieno[3,2-b:2',3'-d]azepine-8-carboxamide.
Flash column chromatography (SiO₂, 4 g, 0-50% THF in DCM, gradient elution) then prep HPLC Method 4;
R' 2.26 min (Method 1a); m/z 786 (M + H)⁺ (ES⁺);
¹H NMR δ: 1.67 (4H, br t), 3.18-3.30 (2H, br), 3.50 (4H, br t), 3.73 (4H, s), 3.78-4.24 (2H, br), 6.32-6.52 (1H, br), 7.19-7.30 (3H, over-lapping m), 7.33 (1H, dd), 7.36-7.62 (4H, over-lapping m), 7.89 (1H, s), 8.10 (1H, d), 8.40 (1H, s), 10.25 (1H, s), 10.77 (1H, s).

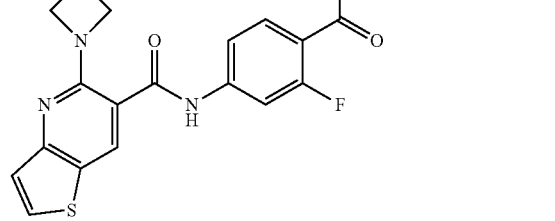

29: 4-(4-(2-(2-oxa-7-azaspiro[3.5]nonan-7-yl)nicotinamido)benzoyl)-N-(2,6-difluorophenyl)-5,6-dihydro-4H-dithieno[3,2-b:2',3'-d]azepine-8-carboxamide.
Flash column chromatography (SiO2, 12 g, 0-5% MeOH in DCM, gradient elution);
R' 2.31 min (Method 1a); m/z 712 (M + H)⁺ (ES⁺);
¹H NMR δ: 1.78 (4H, apparent t), 3.17 (4H, apparent t), 3.24 (2H, apparent t), 3.80-4.24 (2H, br), 4.28 (4H, s), 6.38 (1H, br d), 6.95 (1H, dd), 7.20-7.28 (5H, over-lapping m), 7.39-7.46 (1H, m), 7.66 (2H, d), 7.81 (1H, dd), 7.90 (1H, s), 8.29 (1H, dd), 10.25 (1H, s), 10.63 (1H, s)..

TABLE 2-continued

Additional Compound Examples of the Invention

Structure, Example No., Name, Preparative HPLC or Column Chromatography
Purification Method (where emloyed), LC-MS Analysis and ¹HNMR Spectral Data 30: N-(2,6-difluorophenyl)-4-(4-(5-methyl-2-(2-oxa-7-azaspiro[3.5]nonan-7-yl)nicotinamido)benzoyl)-5,6-dihydro-4H-dithieno[3,2-b:2',3'-d]azepine-8-carboxamide.
Flash column chromatography (SiO₂, 24 g, 0-10% MeOH in DCM, gradient elution) then prep HPLC Method 6;
R' 2.44 min (Method 1a); m/z 726 (M + H)⁺ (ES⁺);
¹H NMR δ: 1.78-1.81 (4H, m), 2.24 (3H, s), 3.06-3.09 (4H, m), 3.24 (2H, apparent t), 3.79-4.23 (2H, br), 4.29 (4H, s), 6.35-6.40 (1H, m), 7.21-7.27 (5H, over-lapping m), 7.39-7.46 (1H, m), 7.66 (2H, d), 7.73 (1H, d), 7.90 (1H, s), 8.16 (1H, dd), 10.25 (1H, s), 10.81 (1H, s).

31: 4-(4-(2-(2-oxa-6-azaspiro[3.3]heptan-6-yl)nicotinamido)benzoyl)-N-(2,6-difluorophenyl)-5,6-dihydro-4H-dithieno[3,2-b:2',3'-d]azepine-8-carboxamide.
Prep HPLC Method 6;
R' 1.84 min (Method 1a); m/z 684 (M + H)⁺ (ES⁺);
¹H NMR δ: 3.23-3.26 (2H, br t), 3.76-4.20 (2H, br), 4.08 (4H, s), 4.66 (4H, s), 6.42 (1H, br d), 6.75 (1H, dd), 7.20-7.30 (5H, over-lapping m), 7.39-7.46 (1H, m), 7.65-7.70 (3H, over-lapping m), 7.91 (1H, s), 8.21 (1H, dd), 10.27 (1H, s), 10.49 (1H, s).

32: N-(2,6-difluorophenyl)-4-(4-(5-methyl-2-(2-oxa-6-azaspiro[3.3]heptan-6-yl)nicotinamido)benzoyl)-5,6-dihydro-4H-dithieno[3,2-b:2',3'-d]azepine-8-carboxamide.
Flash column chromatography (SiO2, 12 g, 0-5% MeOH in DCM, gradient elution) then prep HPLC Method 4;
R' 1.86 min (Method 1a); m/z 698 (M + H)⁺ (ES⁺);
¹H NMR δ: 2.18 (3H, s), 3.24 (2H, apparent t), 3.88-4.13 (2H, br), 4.03 (4H, s), 4.65 (4H, s), 6.41 (1H, br d), 7.19-7.29 (5H, over-lapping m), 7.39-7.46 (1H, m), 7.55 (1H, d), 7.66 (2H, d), 7.91 (1H, s), 8.06 (1H, dd), 10.26 (1H, s), 10.47 (1H, s).

TABLE 2-continued

Additional Compound Examples of the Invention

Structure, Example No., Name, Preparative HPLC or Column Chromatography Purification Method (where emloyed), LC-MS Analysis and ¹HNMR Spectral Data

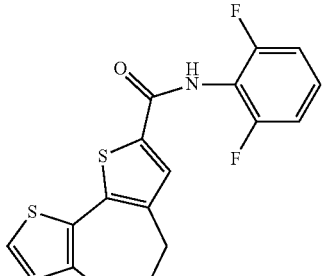

33: 4-(4-(2-(3-oxa-9-azaspiro[5.5]undecan-9-yl)nicotinamido)benzoyl)-N-(2,6-difluorophenyl)-5,6-dihydro-4H-dithieno[3,2-b:2',3'-d]azepine-8-carboxamide.
Flash column chromatography (SiO$_2$, 4 g, 0-5% MeOH in DCM, gradient elution);
R$^t$ 2.40 min (Method 1a); m/z 740 (M + H)$^+$ (ES$^+$);
¹H NMR δ: 1.39 (4H, br t), 1.49 (4H, br t), 3.20-3.28 (6H, br t), 3.52 (4H, br t), 3.80-4.26 (2H, br), 6.37 (1H, br d), 6.93 (1H, dd), 7.19-7.28 (5H, over-lapping m), 7.39-7.46 (1H, m), 7.67 (2H, d), 7.80 (1H, dd), 7.90 (1H, s), 8.28 (1H, dd), 10.24 (1H, s), 10.64 (1H, s).

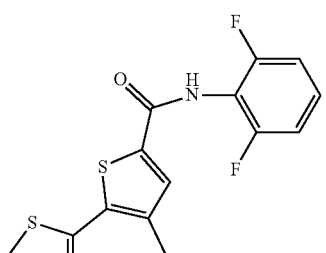

34: N-(2,6-difluorophenyl)-4-(4-(5-methyl-2-(3-oxa-9-azaspiro[5.5]undecan-9-yl)nicotinamido)benzoyl)-5,6-dihydro-4H-dithieno[3,2-b:2',3'-d]azepine-8-carboxamide.
Flash column chromatography (SiO2, 12 g, 50-100% EtOAc in isohexane, gradient elution);
R$^t$ 2.56 min (Method 1a); m/z 754 (M + H)$^+$ (ES$^+$);
¹H NMR δ: 1.39 (4H, apparent t), 1.51 (4H, apparent t), 2.24 (3H, s), 3.12-3.19 (4H, br), 3.24 (2H, apparent t), 3.52 (4H, apparent t), 3.84-4.24 (2H, br), 6.37 (1H, br d), 7.19-7.28 (5H, over-lapping m), 7.38-7.46 (1H, m), 7.67 (2H, d), 7.73 (1H, dd), 7.90 (1H, s), 8.17 (1H, dd), 10.25 (1H, s), 10.86 (1H, s).

Biological Testing: Experimental Methods

Assessment of RSV Induced CPE in HEp2 Cells

HEp2 cells were seeded (10$^3$/well/50 μL) in 384-well plates (Catalogue number 353962, BD Falcon, Oxford, UK) in 5% FBS-DMEM (containing 2 mM L-glutamine and 1 mM sodium pyruvate) one day before infection. RSV A2 strain (#0709161v, NCPV, Public Health England, Wiltshire) or RSV B Washington strain (VR-1580, ATCC, Manassas, Va. 20108) virus solutions were prepared in serum free-DMEM (containing 2 mM L-glutamine and 1 mM sodium pyruvate), and then added (50 μL/well) to achieve a final virus concentration of 1 MOI for RSV A2 and 0.2 MOI for RSV B. Simultaneously, test compounds (0.5 μL DMSO solution) were added to 100 μL of HEp2 cell culture with virus solution to provide a final DMSO solution of 0.5%. Plates were incubated (37° C./5% CO$_2$) for 5 days for studies using RSV A2 strain or 6 days for those using RSV B strain, and then resazurin sodium salt (5 μL of 0.03% solution; Sigma-Aldrich, Dorset, UK) was added to each well and the plate incubated for a further 6 hr (37° C./5% CO$_2$). The fluorescence of each well [545 nm (excitation)/590 nm (emission)] was determined using a multi-scanner (Clariostar: BMG, Buckinghamshire, UK). The percentage inhibition for each well was calculated and the IC$_{50}$, IC$_{75}$ and IC$_{90}$ values were calculated from the concentration-response curve generated for each test compound.

Assessment of RSV F Protein Expression in BEAS2B Bronchial Epithelial Cells

An early event which follows the infection of epithelial cells by RSV is the expression of RSV F-protein on the cells' surface. BEAS2B cells were grown in 96 well plates. Once more than 70% confluent, cells were infected with RSV A2 (#0709161v, NCPV, Public Health England, Wiltshire) at an MOI of 0.1 in clear RPMI-1640 medium (Life technologies, Paisley, UK) with 2% FBS (Life technologies, Paisley, UK), and incubated for 3 days (37° C./5% CO$_2$).

Supernatant was aspirated and the cells were fixed with 4% formaldehyde (100 μL in PBS solution) for 20 min, washed 3 times with washing buffer (200 μL; PBS containing 0.05% Tween-20) and incubated with blocking solution (100 μL; 5% BSA in washing buffer) for 1 hr.

Cells were then washed with washing buffer (200 µL) and incubated overnight at 4° C. with anti-RSV (2F7; mouse monoclonal, lot GR160290, Cat. No. ab43812, Abcam plc, Cambridge, UK) F-fusion protein antibody (50 µL; prepared at a 1:2000 dilution in 5% BSA/washing buffer).

After washing, cells were incubated with an HRP-conjugated anti-mouse IgG antibody (50 µL prepared at a 1:2000 dilution in 5% BSA in PBS; lot 00095437, Cat. No. P0447, Dako UK Ltd, Cambridgeshire, UK) for 1 hr. Cells were washed twice with washing buffer and once with PBS. TMB substrate (50 µL; substrate reagent pack lot 320436, Cat. No. DY999, R&D Systems, Inc. Abingdon, UK) was then added and the reaction was stopped by the addition of aq sulfuric acid (50 µL; 2N).

The resultant signal was determined colourimetrically (OD: 450 nm with a reference wavelength of 655 nm) in a microplate reader (Multiskan FC®, ThermoFisher Scientific). Cells were then washed and 0.5% crystal violet solution (50 µL; lot SLB4576, Cat. No. HT90132-1L, Sigma-Aldrich) was applied for 30 min. After washing with PBS (200 µL) 2 times, 1% SDS (100 µL) was added to each well, and plates were shaken lightly for 1 hr prior to reading the absorbance at 595 nm. The measured $OD_{450-655}$ readings were corrected for cell number by dividing the $OD_{450-655}$ by the $OD_{595}$ readings. The percentage inhibition for each well was calculated and the $IC_{50}$ value derived from the concentration-response curve generated for each test compound.

Cell Viability: Resazurin Assay

HEp2 cells were seeded in 384-well plates ($10^3$/well/50 µL; BD Falcon Ref 353962) in FBS DMEM (5%, containing 2 mM L-glutamine and 1 mM sodium pyruvate) one day before experimentation. Serum-free DMEM (50 µL) was added to test wells, while for control wells the media was removed and sterile water (100 µL) added. Test compounds (0.5 µL DMSO solution) were added to give a final DMSO concentration of 0.5%. HEp2 cells were incubated with each test compound for 5 days (37° C./5% $CO_2$ in 2.5% FBS) and then resazurin stock solution (5 µL; 0.03%) was added to each well and the plate incubated for a further 6 hr (37° C./5% $CO_2$). The fluorescence of each well at 545 nm (excitation) and 590 nm (emission) was determined using a multi-scanner (Clariostar: BMG Labtech). The percentage loss of cell viability was calculated for each well relative to vehicle (0.5% DMSO) treatment.

Note that any apparent increase in cell viability associated with test compound treatment relative to vehicle is consequently tabulated as a negative percentage. Where appropriate, a $CC_{50}$ value was calculated from the concentration-response curve generated from the concentration-response curve for each test compound.

Assessment of Virus Titre in Air-Liquid Interface (ALI) Cultured Bronchial Epithelial Cells ALI cultured human bronchial epithelial cells were sourced from Epithelix Sarl (Geneva, Switzerland) and maintained by changing the basal media every 3-4 days, whilst the apical surface was washed once weekly with PBS. On day 0, the apical surface of each well was washed once with sterile PBS (300 µL) and the inserts transferred to new 24-well plates containing fresh MucilAir culture medium (780 µL; EP04MM). RSV A2 (50 µL; diluted in MucilAir culture medium to give a final MOI of 0.01) was added to cells for one hr (37° C./5% $CO_2$). For the purposes of standardizing MOI calculations, each MucilAir insert was estimated to contain $2 \times 10^5$ apical facing cells per well. Virus inoculum was removed with a pipette and inserts were washed twice with sterile PBS (300 µL).

Sampling was conducted by adding sterile PBS (300 µL) to the apical surface of each well for 5 min. The apical sample was then removed and transferred to tubes containing 50% sucrose dissolved in PBS (100 µL) before being stored at −80° C. This harvesting procedure was repeated daily beginning on day 0 and concluding on day 10.

ALI cultures are dosed apically with test compound on days 0-7 for "early intervention" protocols, or days 3-7 for "late intervention" protocols. The test compound (50 µL in 0.5% DMSO/PBS) was added to the apical surface and incubated (37° C./5% $CO_2$) for 1 hr before being removed. Vehicle treatments (0.5% DMSO/PBS) were performed on the corresponding apical surfaces to ensure each well received the same number of manipulations. On day 5, the basal media was removed from each well and replenished with fresh MucilAir culture media as a necessary maintenance step for ALI culture cells.

Virus titre was quantified by plaque assay. HEp2 cells were grown in 24-well plates (Corning) for 48 hr prior to infection in DMEM containing 10% FBS until they attained 100% confluency.

Collected samples were thawed at RT and ten-fold serial dilutions were prepared in serum-free DMEM. The growth medium from HEp2 cells was aspirated and replaced with 300 µL of serially diluted virus collections and left to infect at 37° C./5% $CO_2$ for 4 hr. The infectious media was aspirated and replaced with 1 mL Plaque Assay Overlay (0.3% Avicel RC-591 (FMC Biopolymer UK, Girvan, Scotland)) in MEM, supplemented to a final concentration of 2% FCS), and left for 7 days at 37° C./5% $CO_2$. Cells were fixed with ice-cold methanol for 10 min, then removed and cells subjected to two washes with sterile PBS. Cells were then stained with crystal violet solution (200 µL 0.1%, in distilled water) for 1 hr. Crystal violet solution was removed and cells rinsed with water before plaques were counted and virus titre enumerated.

RSV Infection in Mice

Non-fasted mice (male BALB/C, 20-30 g) can be infected intranasally with RSV A2 or virus diluent (DMEM, 2% FBS, 12.5% sucrose) under isoflurane (5% in $O_2$) anaesthesia. The A2 strain of RSV (50 µL of $1.3 \times 10^6$ PFU/mL: final $0.65 \times 10^5$ PFU/mouse) can then be instilled into each nostril in a drop wise fashion alternating between the two until a volume of 50 µL was delivered. Following infection, each animal can be weighed on a daily basis to monitor changes. Test compounds can be dissolved in 100% DMSO (at 20 mg/mL and/or 2 mg/mL), then diluted at 1:10 in isotonic saline to achieve 10% DMSO in all treatments. Formulations can be sonicated to produce a suspension. The suspension can be administered intratracheally (20 µL) with a FMJ-250 Penn-Century device or intranasally (40 µL) with a pipette 1 day and 1 hr before infection (day 0), and then on days 1, 2 and 3 post infection.

Four days after RSV challenge, the animals are euthanised (by intraperitoneal injection of a pentobarbitone overdose), the tracheas cannulated and BALF extracted for total and differential cell counts. Following BALF collection, the right lung can be removed from each animal and homogenised in ice-cold Dulbecco's modified Eagles medium (using 10 times the lung weight of DMEM containing 1% BSA and 25% sucrose) for 2×20 second bursts. The homogenate can then be transferred into a sterile tube and spun at 4° C. (2000 rpm; for 5 min), the clarified homogenate transferred to a chilled cryovial, snap frozen and stored at −80° C. The supernatants from lung homogenates can then be used for RSV plaque assay or other assays.

RSV Infection in Cotton Rats

Male *Sigmodon hispidus* cotton rats between 6 and 8 weeks of age were infected with hRSV/A/Long (ATCC, Manassas, Va.; $10^5$ pfu) in a volume of 0.1 mL of sucrose stabilizing media. Test compounds were dissolved in 100% DMSO (at 3.3, 10, 33 and 100 mg/mL), then diluted (1:10 in isotonic saline to achieve 10% DMSO in all treatments) and sonicated to produce suspensions which were administered intranasally (50 µL) by pipette 4 hr before infection (on day 0), and then on days 1, 2 and 3 post infection. Four days after RSV challenge, the animals were euthanised and the lungs removed. The left lobe was used for viral titration via plaque assay and the lingular lobe for RSV/A/Long NS-1 qRT-PCR and cytokine qRT-PCR.

The supernatants of lung homogenates were diluted 1:10 and 1:100 in Eagle (E)-MEM. Confluent HEp2 monolayers in 24-well plates were infected in duplicate (50 μL of sample per well) starting with undiluted (neat) samples followed by diluted homogenates. After incubation for 1 hr (37° C./5% $CO_2$) wells were overlaid with 0.75% methylcellulose medium and plates replaced in the 37° C. incubator. After incubation (for 4 days), the overlay was removed, the cells fixed with 0.1% crystal violet stain (for 1 hr) and then rinsed and air-dried. Plaques were counted and viral titers were expressed as plaque forming units per gram ($pfu.g^{-1}$) of tissue.

Total RNA was also extracted from homogenized lung tissue (RNeasy purification kit; Qiagen) and a sample (1 μg) used to prepare cDNA using QuantiTect Reverse Transcription Kit (Qiagen). For real-time PCR reactions (RSV NS-1 and RANTES genes) the QuantiFast SYBR® Green PCR Kit (Qiagen) was used in a final volume of 25 μL, with final primer concentrations of 0.5 μM. Amplifications were performed on a Bio-Rad iCycler for 1 cycle of 950C for 3 min, followed by 40 cycles of 950C for 10 sec, 600C for 10 sec, and 720C for 15 sec. Baseline cycles and cycle threshold (Ct) were calculated by the iQ5 software in the PCR Base Line Subtracted Curve Fit mode.

The standard curves were developed using the serially diluted cDNA sample most enriched in the transcript of interest (e.g., lungs from day 4 post-primary RSV infection). The Ct values were plotted against $log_{10}$ cDNA dilution factor and the curves were used to convert the Ct values obtained for different samples to relative expression units, which were then normalized against the level of R-actin mRNA ("housekeeping gene") expressed in the corresponding sample. The mRNA levels were expressed as the geometric mean±SEM for all animals in a group.

In Vitro Screening Results

The profiles of the compounds of the invention, as disclosed herein, are summarised below (Table 3) and demonstrate potent inhibitory activities against both RSV A2-induced CPE and (in many cases) RSV B-induced CPE in HEp2 cells. Furthermore, the compound Example 1 exhibited potent inhibition of RSV A2 F-protein expression in BEAS2B bronchial epithelial cells ($IC_{50}$ value: 0.021 nM, $IC_{90}$ value: 0.078 nM, n=2). Little or no effect on cell viability, resulting from incubation with the compounds of the invention, was detected (Table 3).

TABLE 3

The effects of treatment with compounds of this disclosure on RSV A2- and RSV B-induced CPE in HEp2 cells and on cell viability.

| Compound Example No. | RSV A2 CPE | | RSV B CPE | | Cell Viability |
|---|---|---|---|---|---|
| | $IC_{50}$ (nM) | % Inhibition | $IC_{50}$ (nM) | % Inhibition | $CC_{50}$ (nM) |
| 1 | 0.11 | 100[1] | 9.0 | 100[2] | >13800 |
| 2 | 0.37 | 97[1] | 8.7 | 86[2] | >13300 |
| 3 | 0.15 | 95[1] | 14 | 100[2] | >13700 |
| 4 | 0.28 | 96[1] | 18 | 98[2] | >13500 |
| 5 | 0.55 | 89[1] | 19 | 97[2] | >13400 |
| 6 | 0.44 | 93[1] | 63 | 95[3] | >14000 |
| 7 | 2.6 | 87[1] | 97 | 82[3] | >13700 |
| 8 | 0.68 | 100[1] | 137 | 97[3] | >14500 |
| 9 | 0.18 | 100[1] | 54 | 100[2] | >14100 |
| 10 | 0.75 | 97[1] | 123 | 100[3] | >13800 |
| 11 | 0.21 | 100[1] | 8.3 | 100[2] | >13900 |
| 12 | 0.14 | 84[1] | 3.1 | 97[3] | >13500 |
| 13 | 0.14 | 77[1] | 1.2 | 80[3] | >13200 |
| 14 | 0.19 | 100[1] | 19 | 100[2] | >13600 |
| 15 | 0.30 | 100[1] | 86 | 90[3] | >13800 |
| 16 | 0.18 | 96[1] | 32 | 100[2] | >13600 |
| 17 | 0.17 | 92[1] | 19 | 100[2] | >13400 |
| 18 | 0.17 | 100[1] | 14 | 92[2] | >13400 |
| 19 | 0.18 | 93[1] | 29 | 86[3] | >13200 |
| 20 | 0.17 | 100[1] | 18 | 100[2] | >13500 |
| 21 | 0.37 | 91[1] | 17 | 91[2] | >13800 |
| 22 | 1.7 | 94[1] | 159 | 94[3] | >13500 |
| 23 | 0.67 | 96[1] | 70 | 96[3] | >13200 |
| 24 | 0.54 | 98[1] | 11 | 84[2] | >13400 |
| 25 | 0.18 | 100[1] | 10 | 89[2] | >13000 |
| 26 | 1.0 | 98[1] | 17 | 93[2] | >13100 |
| 27 | 0.63 | 94[1] | 32 | 93[3] | >13100 |
| 28 | 0.48 | 89[1] | 15 | 92[2] | >12700 |
| 29 | 3.6 | 100[1] | 490 | 51[3] | >14000 |
| 30 | 0.42 | 100[1] | 130 | 100[3] | >13800 |
| 31 | 10.8 | 62[1] | 1050 | 57[3] | >14600 |
| 32 | 0.59 | 100[1] | 602 | 90[3] | >14300 |
| 33 | 1.4 | 100[1] | >1350 | 23[3] | >13500 |
| 34 | 4.4 | 100[1] | >1330 | 9[3] | >13300 |

Table Footnotes:
[1]Inhibition (%) at 0.01 μg/mL;
[2]Inhibition (%) at 0.1 μg/mL;
[3]Inhibition (%) at 1 μg/mL;
NT = not tested.

Anti-Viral Effects in Human Primary Bronchial Epithelial Cells.

Anti-viral effects were also evaluated using air-liquid interface cultured human primary bronchial epithelial cells. The cells undergo extensive mucociliary differentiation, resulting in cultures with morphological characteristics similar to those observed in the normal human respiratory epithelium. As a result, this cell model closely mimics RSV infections in human airways. The RSV titre increased from day 1, peaked at day 3 and then gradually and moderately reduced until day 7. Treatment with compound Examples 1 or 12 at 0.1 μg/mL to an apical well daily from day 3 to day 7 (late intervention) produced a remarkable reduction of virus titre in excess of 2 log orders (i.e. >99%) over 7 days (Tables 4 and 5).

TABLE 4

The effects of late intervention (days 3-7) with compound Example 1 on RSV A2 viral titre in apical wash from RSV A2 infected, air-liquid interface cultured, bronchial epithelial cells.

| Treatment (plus virus) | Drug Conc. mg/mL | Virus titre[1] in apical wash on days indicated expressed as the geometric mean[2] (log PFU/mL) ± SD[3] | | | | | | |
|---|---|---|---|---|---|---|---|---|
| | | 0 | 1 | 2 | 3 | 4 | 5 | 6 | 7 |
| Vehicle | none | 0 | 2.49 (±0.37) | 3.90 (±0.07) | 5.57 (±0.08) | 5.94 (±0.12) | 5.99 (±0.04) | 4.06 (±0.47) | 4.08 (±0.49) |

TABLE 4-continued

The effects of late intervention (days 3-7) with compound Example 1 on RSV A2 viral titre in apical wash from RSV A2 infected, air-liquid interface cultured, bronchial epithelial cells.

| Treatment (plus virus) | Drug Conc. mg/mL | Virus titre[1] in apical wash on days indicated expressed as the geometric mean[2] (log PFU/mL) ± SD[3] | | | | | | | |
|---|---|---|---|---|---|---|---|---|---|
| | | 0 | 1 | 2 | 3 | 4 | 5 | 6 | 7 |
| Compound Example 1 | 0.1 | 0 | 2.14 (±0.25) | 3.05 (±0.07) | 5.18 (±0.39) | 3.55 (±0.26) | 3.68 (±0.62) | 2.24 (±0.49) | 1.71 (±1.7) |

[1]The LOQ of virus plaque assay is 1.5 log PFU/mL and a value of 1 PFU/mL was allocated for statistical analysis if plaque was not detected with × 10 diluted apical wash.
[2]The geometric mean was calculated as the average of the log values of the virus titre (PFU/mL).
[3]The standard deviation was calculated using the log values and the n value was 3 for all experiments.

TABLE 5

The effects of late intervention (days 3-7) with compound Example 12 on RSV A2 viral titre in apical wash from RSV A2 infected, air-liquid interface cultured, bronchial epithelial cells.

| Treatment (plus virus) | Drug Conc. mg/mL | Virus titre in apical wash on days indicated expressed as the geometric mean (log PFU/mL) ± SD[1] | | | | | | | |
|---|---|---|---|---|---|---|---|---|---|
| | | 0 | 1 | 2 | 3 | 4 | 5 | 6 | 7 |
| Vehicle | none | 0 | 2.86 (±0.35) | 5.12 (±0.21) | 5.22 (±0.66) | 5.93 (±0.12) | 4.96 (±0.42) | 4.34 (±0.11) | 4.14 (±0.33) |
| Compound Example 12 | 0.1 | 0 | 2.57 (±0.23) | 4.86 (±0.35) | 5.27 (±0.26) | 4.71 (±0.32) | 3.45 (±0.71) | 2.62 (±0.35) | 1.22 (±1.1) |

[1]Footnotes are the same as for Table 4 above.

In Vivo Testing

Human RSV is able to infect and replicate in a number of animal species used for pre-clinical screening, thereby enabling the performance and profiles of novel anti-infective agents to be assessed and compared in vivo (Bem, et al., 2011). Although primate species can also be infected and studied, most work of this nature is conducted in mice or cotton rats. Both standard, inbred mouse strains and cotton rats are characterised as "semi-permissive" for the replication of human RSV, although significantly greater viral replication is seen in cotton rats than inbred mouse strains. Compound Examples 1 and 12 were therefore tested in the cotton rat in vivo system.

In RSV/A/Long infected cotton rats, virus titre peaked on day 4 following inoculation as previously reported (Boukhvalova et al., 2010). The test compounds were administered 4 hr before inoculation (day 0), then 1, 2 and 3 days after virus infection intranasally. Lung sample was collected at 4 days post infection. Example 1 demonstrated potent dose-dependent inhibition of viral titre in lung homogenates, and also Example 12 showed a 0.7 log reduction of virus titre by intra-nasal dosing at 1 mg/ml (Table 6 and 7). In addition, compound Example 1 displayed a dose-dependent inhibition of RSV NS-1 gene transcripts (Table 8) and of RANTES transcripts in lung (Table 9).

TABLE 6

The effects of intranasal treatment with compound Example 1 on RSV viral titre in lung from RSV/A/Long infected cotton rats.

| Treatment (plus virus) | Drug Conc (mg/mL) | Virus titre (log, PFU/lung)[1] | | |
|---|---|---|---|---|
| | | Geometric Mean | Median | Interquartile Range |
| Vehicle | None | 5.7 | 5.7 | 5.4-5.8 |
| Compound Example 1 | 0.1 | 5.4 | 5.4 | 5.1-5.6 |
| | 0.33 | 5.0 | 5.0 | 4.9-5.1 |
| | 1.0 | 4.3 | 4.3 | 3.9-4.7 |
| | 3.3 | <2.3[2] | <2.3 | N/A |

[1]n values were 6 for all experiments;
[2]Lower limit of quantitation (LOQ);
N/A: not applicable.

TABLE 7

The effects of intranasal treatment with compound Example 12 on RSV viral titre in lung from RSV/A/Long infected cotton rats.

| Treatment (plus virus) | Drug Conc (mg/mL) | Virus titre (log, PFU/lung)[1] | | |
|---|---|---|---|---|
| | | Geometric Mean | Median | Interquartile Range |
| Vehicle | None | 5.2 | 5.2 | 5.0-5.4 |
| Compound Example 12 | 1.0 | 4.5 | 4.5 | 4.1-4.9 |

[1]n values were 6 for all experiments.

TABLE 8

The effects of intranasal treatment with compound Example 1 on RSV NS-1 gene expression in lung from RSV/A/Long infected cotton rats.

| Treatment (plus virus) | Drug Conc (mg/mL) | RSV NS1 gene transcript (/β-actin)[1] | | % inhibition |
|---|---|---|---|---|
| | | Median | Interquartile Range | |
| Vehicle | None | 3.1 | 2.3-4.0 | |
| Example 1 | 0.33 | 4.4 | 2.2-5.3 | −42 |
| | 1.0 | 1.9 | 1.2-2.5 | 39 |
| | 3.3 | 1.6 | 1.2-2.4 | 48 |
| | 10 | 1.0 | 0.93-1.3 | 68 |

[1]The n values were 6 for all experiments.

TABLE 9

The Effects of intranasal treatment with compound Example 1 on RANTES gene expression in lung from RSV/A/Long infected cotton rats.

| Treatment (plus virus) | Drug Conc (mg/mL) | RANTES gene transcript (/β-actin)[1] | | % Inhibition |
|---|---|---|---|---|
| | | Median | Interquartile Range | |
| Vehicle | none | 3.6 | 3.4-4.6 | |
| Example 1 | 0.33 | 3.9 | 3.4-5.1 | −8 |
| | 1.0 | 2.3 | 1.5-4.0 | 36 |
| | 3.3 | 2.3 | 1.4-2.8 | 36 |
| | 10 | 1.4 | 1.2-1.4 | 61 |

[1]The n values were 6 for all experiments.

Summary

The in vitro antiviral activity of the compounds of the invention has been demonstrated by their cytoprotective effect on HEp2 cells infected with RSV. In this assay system the inhibition of virus replication was detected and quantified from the resulting inhibition of virus-mediated CPE. It is particularly noteworthy that compounds of the invention are potent inhibitors of the CPE induced by the RSV A strain and (in most cases) the RSV B strain studied. The potent antiviral activity of compound Example 1 was further evidenced by its inhibition of RSV A2 F-protein expression in BEAS2B cells.

The compounds of the invention demonstrate low mammalian cell toxicity as measured by their lack of any significant effects in the cell viability assay. Furthermore, in an in vitro model of human lung epithelium, comprising an air-liquid interface culture of bronchial epithelial cells, compound Examples 1 and 12 of the invention completely inhibited virus titre when administered by late stage intervention. This observation is particularly significant for the treatment of established disease.

The in vivo antiviral activity of the compounds of the invention has been demonstrated in cotton rats infected with RSV. In the assay systems the inhibition of virus replication was detected and quantified from the RSV titre in lung homogenates as measured in a plaque assay. In keeping with the data obtained from the studies conducted in ALI-cultured human bronchial cells, compound Example 1 completely inhibited virus titre in the lungs of RSV A (Long) infected cotton rats. The compounds of the present invention thus have the necessary attributes to be effective medicines for the treatment and/or prevention of RSV infection and associated disease.

REFERENCES

Abman S. H., Ogle J. W., Butler-Simon N., Rumack C. M., and Accurso F. J. Role of respiratory syncytial virus in early hospitalizations for respiratory distress of young infants with cystic fibrosis. *J. Pediatr.*, 1988, 113, 826-30.

Albright J. D. and Delos Santos E. G. Bicyclic Benzazepine Derivatives as Vasopressin Antagonists, WO 96/22294 (see p. 45).

Bem R. A., Domachowske J. B. and Rosenberg, H. F. Animal models of human respiratory syncytial disease. *Am. J. Physiol.*, 2011. 301, L148-L156.

Boukhvalova M. S., Yim K. C., Prince G. A., and Blanco J. C. Methods for monitoring dynamics of pulmonary RSV replication by viral culture and by real-time reverse transcription-PCR in vivo: Detection of abortive viral replication. *Curr. Protoc. Cell Biol.*, 2010 March; Chapter 26:Unit 26.6.

Hall C. B., Douglas R. G. Jr., Schnabel K. C. and Geiman J. M. Infectivity of respiratory syncytial virus by various routes of inoculation. *Infect. Immun.*, 1981, 33, 779-83.

Holt P. G. and Sly P. D. Interactions between RSV infection, asthma, and atopy: unravelling the complexities. *J. Exp. Med.*, 2002, 196, 1271-1275.

Johnson J. E., Gonzales R. A., Olson S. J., Wright P. F. and Graham, B. S. The histopathology of fatal untreated human respiratory syncytial virus infection. *Modern Pathology*, 2007, 20, 108-119.

Lee N., Lui G. C., Wong K. T., Li T. C., Tse E. C., Chan J. Y., Yu J., Wong S. S., Choi K. W., Wong R. Y., Ngai K. L., Hui D. S. and Chan P. K. High morbidity and mortality in adults hospitalized for respiratory syncytial virus infections. *Clin. Infect. Dis.*, 2013, 57, 1069-77.

Mohan A., Chandra S., Agarwal D., Guleria R., Broor S., Gaur B. and Pandey R. M. Prevalence of viral infection detected by PCR and RT-PCR in patients with acute exacerbation of COPD: A systematic review. *Respirology*, 2010, 15, 536-542.

Newcomb D. C. and Peebles R. S. Jr. Bugs and asthma: a different disease? *Proc. Am. Thorac. Soc.*, 2009, 1; 6, 266-71.

Olivier A., Gallup J., de Macedo M. M. M. A., Varga S. M. and Ackermann M. Human respiratory syncytial virus A2 strain replicates and induces innate immune responses by respiratory epithelia of neonatal lambs. *Int. J. Exp. Pathol.*, 2009, 90, 431-438.

Panayiotou C., Richter J., Koliou M., Kalogirou N., Georgiou E. and Christodoulou C. Epidemiology of respiratory syncytial virus in children in Cyprus during three consecutive winter seasons (2010-2013): age distribution, seasonality and association between prevalent genotypes and disease severity. *Epidemiol. Infect.*, 2014, Jan. 24, 1-6.

Walsh E. E., McConnochie K. M., Long C. E. and Hall C. B. Severity of respiratory syncytial virus infection is related to virus strain. *J. Infect. Dis.*, 1997, 175, 814-20.

Zhang Z-Y., Du L-N., Chen X., Zhao Y., Liu, E-M., Yang X-Q. and Zhao X-D Genetic variability of respiratory syncytial viruses (RSV) prevalent in Southwestern China from 2006 to 2009: emergence of subgroup B and A RSV as dominant strains. *J. Clin. Microbiol.*, 2010, 48, 1201-7.

Zhu Q., McAuliffe J. M., Patel N. K., Palmer-Hill F. J., Yang C. F., Liang B., Su L., Zhu W., Wachter L., Wilson S., MacGill R. S., Krishnan S., McCarthy M. P., Losonsky G. A. and Suzich J. A. Analysis of respiratory syncytial virus preclinical and clinical variants resistant to neutralization by monoclonal antibodies palivizumab and/or motavizumab. *J Infect. Dis.*, 2011, 203, 674-82.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A compound of formula (I),

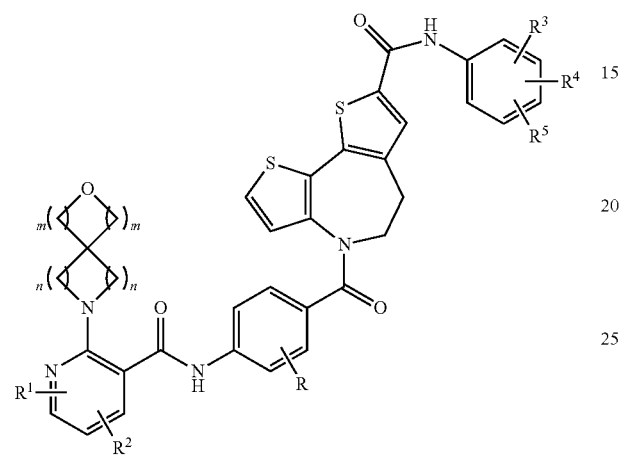

(I)

wherein:

R represents hydrogen or halo;

$R^3$ represents hydrogen, hydroxy, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ hydroxyalkyl, $C_{1-4}$ haloalkoxy, —O(CH$_2$)$_2$OH or —O(CH$_2$)$_2$O $C_{1-2}$ alkyl;

$R^4$ represents hydrogen, halo, cyano, $C_{1-4}$ alkyl, $C_{2-4}$ alkenyl, $C_{1-4}$ alkynyl, $C_{1-4}$ haloalkyl, $C_{3-6}$ cycloalkyl, $C_{1-4}$ alkoxy or $C_{1-4}$ haloalkoxy;

$R^5$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

m and n represent integers which may be independently selected from 1 and 2;

and either (a) $R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-2}$ alkoxy$C_{1-2}$ alkyl or $C_{1-4}$ haloalkoxy; and $R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy, $C_{1-2}$ alkoxy$C_{1-2}$ alkyl, $C_{1-4}$ hydroxyalkyl or cyano; or (b) $R^1$ and $R^2$ are in positions 6 and 5 respectively of the pyridine nucleus and are joined to form a bicyclic system comprising either a 5- or 6-membered carbocyclic ring or a 5- or 6-membered heterocyclic ring which contains heteroatoms selected only from O and S, which is fused to said pyridine nucleus;

or a pharmaceutically acceptable salt thereof.

2. A compound according to claim 1 wherein n represents 1 and m represents 2.

3. A compound according to claim 2 which is a compound of formula (Ib)

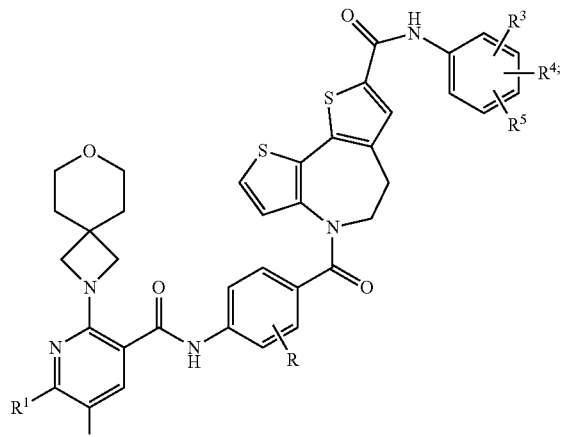

(Ib)

or a pharmaceutically acceptable salt thereof.

4. A compound according to claim 3 which is a compound of formula (Ic)

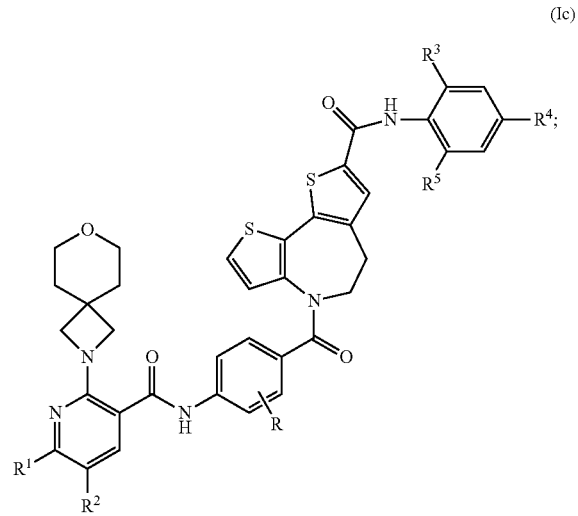

(Ic)

or a pharmaceutically acceptable salt thereof.

5. A compound according to claim 1 wherein R represents hydrogen or fluoro.

6. A compound according to claim 1 wherein $R^3$ represents hydrogen, halo, cyano, $C_{1-4}$ alkyl, $C_{2-4}$ alkenyl, $C_{2-4}$ alkynyl, $C_{1-4}$ haloalkyl, $C_{3-6}$ cycloalkyl or $C_{1-4}$ haloalkoxy.

7. A compound according to claim 1 wherein:

$R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy; and $R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy or cyano.

8. A compound according to claim 7 wherein one of $R^1$ and $R^2$ is $C_{1-4}$ alkyl, and the other is hydrogen.

9. A compound according to claim 8 wherein $R^1$ is hydrogen in the 6-position of the pyridine ring and $R^2$ is methyl in the 5-position of the pyridine ring.

10. A compound according to claim 1 wherein:

$R^1$ and $R^2$ are in positions 6 and 5 respectively of the pyridine ring and are joined to form a bicyclic system comprising either a 5- or 6-membered carbocyclic ring, or a 5- or 6-membered heterocyclic ring, which contains heteroatoms selected from O and S and is fused to said pyridine nucleus, said bicyclic system being selected from the systems listed below:

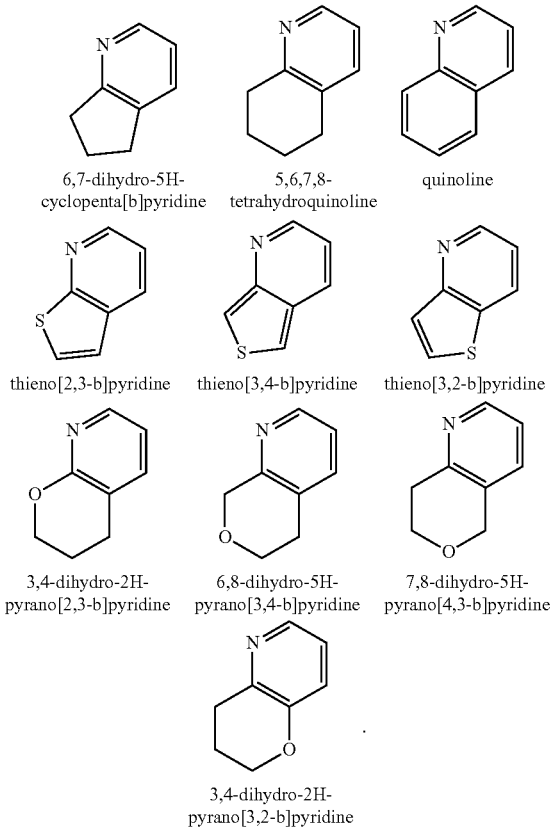

11. A compound according to claim 1 wherein $R^3$, $R^4$ and $R^5$ are selected from hydrogen, halo, $C_{1-4}$ alkyl, $C_{2-4}$ alkenyl, $C_{2-4}$ alkynyl, $C_{1-4}$ haloalkyl, $C_{1-4}$ haloalkoxy, and cyano.

12. A compound according to claim 1 wherein one of $R^3$, $R^4$ and $R^5$ is hydrogen and the remainder are substituents other than hydrogen; or
wherein two of $R^3$, $R^4$ and $R^5$ are hydrogen and the remainder is a substituent other than hydrogen.

13. A compound according to claim 12 wherein one of $R^3$, $R^4$ and $R^5$ is hydrogen and the remainder occupy positions 2- and 6- of the phenyl ring to which they are attached.

14. A compound according to claim 13 wherein one of $R^3$, $R^4$ and $R^5$ is hydrogen and the remainder are selected from the group consisting of methyl, trifluoromethyl, cyano and halo.

15. A compound according to claim 1 which is selected from the group consisting of:
N-(2,6-difluorophenyl)-4-(4-(5-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;
4-(4-(2-(7-oxa-2-azaspiro[3.5]nonan-2-yl)-6,7-dihydro-5H-cyclopenta[b]pyridine-3-carbox amido)benzoyl)-N-(2,6-difluorophenyl)-5,6-dihydro-4H-dithieno[3,2-b:2',3'-d]azepine-8-carboxamide;
N-(2,6-difluorophenyl)-4-(4-(5-methyl-2-(7-oxa-2-azaspiro[3.5]nonan-2-yl)nicotinamido) benzoyl-2,3,5,6-d4)-5,6-dihydro-4H-dithieno[3,2-b:2',3'-d]azepine-8-carboxamide;
N-(2,6-difluorophenyl)-4-(4-(5,6-dimethyl-2-(7-oxa-2-azaspiro[3.5]nonan-2-yl)nicotin amido)benzoyl)-5,6-dihydro-4H-dithieno[3,2-b:2',3'-d]azepine-8-carboxamide;
N-(2,6-difluorophenyl)-4-(2-fluoro-4-(6-methyl-2-(7-oxa-2-azaspiro[3.5]nonan-2-yl) nicotinamido)benzoyl)-5,6-dihydro-4H-dithieno[3,2-b:2',3'-d]azepine-8-carboxamide;
4-(4-(2-(7-oxa-2-azaspiro[3.5]nonan-2-yl)nicotinamido)benzoyl)-N-(2,6-difluorophenyl)-5,6-dihydro-4H-dithieno[3,2-b:2',3'-d]azepine-8-carboxamide;
4-(4-(2-(7-oxa-2-azaspiro[3.5]nonan-2-yl)nicotinamido)-2-fluorobenzoyl)-N-(2,6-difluoro phenyl)-5,6-dihydro-4H-dithieno[3,2-b:2',3'-d]azepine-8-carboxamide;
4-(4-(5-methyl-2-(7-oxa-2-azaspiro[3.5]nonan-2-yl)nicotinamido)benzoyl)-N-phenyl-5,6-dihydro-4H-dithieno[3,2-b:2',3'-d] azepine-8-carboxamide;
N-(2-fluorophenyl)-4-(4-(5-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;
N-(2,4-difluorophenyl)-4-(4-(5-methyl-2-(7-oxa-2-azaspiro[3.5]nonan-2yl)nicotinamido) benzoyl)-5,6-dihydro-4H-dithieno[3,2-b:2',3'-d]azepine-8-carboxamide;
N-(2-fluoro-6-methylphenyl)-4-(4-(5-methyl-2-(7-oxa-2-azaspiro[3.5]nonan-2-yl)nicotin amido)benzoyl)-5,6-dihydro-4H-dithieno[3,2-b:2',3'-d]azepine-8-carboxamide;
N-(2-chloro-6-fluorophenyl)-4-(4-(5-methyl-2-(7-oxa-2-azaspiro[3.5]nonan-2-yl)nicotin amido)benzoyl)-5,6-dihydro-4H-dithieno[3,2-b:2',3'-d]azepine-8-carboxamide;
N-(2,6-dichlorophenyl)-4-(4-(5-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;
N-(2-cyano-6-fluorophenyl)-4-(4-(5-methyl-2-(7-oxa-2-azaspiro[3.5]nonan-2-yl)nicotin amido)benzoyl)-5,6-dihydro-4H-dithieno[3,2-b:2',3'-d]azepine-8-carboxamide;
N-(2-fluoro-6-hydroxyphenyl)-4-(4-(5-methyl-2-(7-oxa-2-azaspiro[3.5]nonan-2-yl)nicotin amido)benzoyl)-5,6-dihydro-4H-dithieno[3,2-b:2',3'-d]azepine-8-carboxamide;
N-(2-fluoro-6-methoxyphenyl)-4-(4-(5-methyl-2-(7-oxa-2-azaspiro[3.5]nonan-2-yl)nicotin amido)benzoyl)-5,6-dihydro-4H-dithieno[3,2-b:2',3'-d]azepine-8-carboxamide;
4-(4-(5-methyl-2-(7-oxa-2-azaspiro[3.5]nonan-2-yl)nicotinamido)benzoyl)-N-(2,4,6-trifluorophenyl)-5,6-dihydro-4H-dithieno[3,2-b:2',3'-d] azepine-8-carboxamide;
N-(2,6-difluorophenyl)-4-(2-fluoro-4-(5-methyl-2-(7-oxa-2-azaspiro[3.5]nonan-2-yl)nicotin amido)benzoyl)-5,6-dihydro-4H-dithieno[3,2-b:2',3'-d]azepine-8-carboxamide;
N-(2-chloro-6-fluorophenyl)-4-(2-fluoro-4-(5-methyl-2-(7-oxa-2-azaspiro[3.5]nonan-2-yl) nicotinamido)benzoyl)-5,6-dihydro-4H-dithieno[3,2-b:2',3'-d]azepine-8-carboxamide;
N-(2,6-difluorophenyl)-4-(4-(5-methoxy-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2,6-difluorophenyl)-4-(4-(6-methyl-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2,6-difluorophenyl)-4-(4-(6-methoxy-2-(7-oxa-2-azaspiro[3.5]nonan-2-yl)nicotinamido) benzoyl)-5,6-dihydro-4H-dithieno[3,2-b:2',3'-d]azepine-8-carboxamide;

N-(2,6-difluorophenyl)-4-(4-(5,6-dimethyl-2-(7-oxa-2-azaspiro[3.5]nonan-2-yl)nicotin amido)-2-fluorobenzoyl)-5,6-dihydro-4H-dithieno[3,2-b:2',3'-d]azepine-8-carboxamide;

4-(4-(2-(7-oxa-2-azaspiro[3.5]nonan-2-yl)-6,7-dihydro-5H-cyclopenta[b]pyridine-3-carbox amido)benzoyl)-N-(2-fluoro-6-methylphenyl)-5,6-dihydro-4H-dithieno[3,2-b:2',3'-d]azepine-8-carboxamide;

N-(4-(8-((2,6-difluorophenyl)carbamoyl)-5,6-dihydro-4H-dithieno[3,2-b:2',3'-d]azepine-4-carbonyl)phenyl)-2-(7-oxa-2-azaspiro[3.5]nonan-2-yl)-7,8-dihydro-5H-pyrano[4,3-b]pyridine-3-carboxamide;

N-(4-(8-((2-fluoro-6-methylphenyl)carbamoyl)-5,6-dihydro-4H-dithieno[3,2-b:2',3'-d]azepine-4-carbonyl)phenyl)-2-(7-oxa-2-azaspiro[3.5]nonan-2-yl)-7,8-dihydro-5H-pyrano [4,3-b]pyridine-3-carboxamide;

4-(4-(2-(7-oxa-2-azaspiro[3.5]nonan-2-yl)quinoline-3-carboxamido)benzoyl)-N-(2,6-difluorophenyl)-5,6-dihydro-4H-dithieno[3,2-b:2',3'-d]azepine-8-carboxamide;

4-(4-(5-(7-oxa-2-azaspiro[3.5]nonan-2-yl)thieno[3,2-b]pyridine-6-carboxamido)-2-fluoro benzoyl)-N-(2,6-difluorophenyl)-5,6-dihydro-4H-dithieno[3,2-b:2',3'-d]azepine-8-carboxamide;

4-(4-(2-(2-oxa-7-azaspiro[3.5]nonan-7-yl)nicotinamido) benzoyl)-N-(2,6-difluorophenyl)-5,6-dihydro-4H-dithieno[3,2-b:2',3'-d]azepine-8-carboxamide;

N-(2,6-difluorophenyl)-4-(4-(5-methyl-2-(2-oxa-7-azaspiro[3.5]nonan-7-yl)nicotinamido) benzoyl)-5,6-dihydro-4H-dithieno[3,2-b:2',3'-d]azepine-8-carboxamide;

4-(4-(2-(2-oxa-6-azaspiro[3.3]heptan-6-yl)nicotinamido) benzoyl)-N-(2,6-difluorophenyl)-5,6-dihydro-4H-dithieno[3,2-b:2',3'-d]azepine-8-carboxamide;

N-(2,6-difluorophenyl)-4-(4-(5-methyl-2-(2-oxa-6-azaspiro[3.3]heptan-6-yl)nicotinamido) benzoyl)-5,6-dihydro-4H-dithieno[3,2-b:2',3'-d]azepine-8-carboxamide;

4-(4-(2-(3-oxa-9-azaspiro[5.5]undecan-9-yl)nicotinamido)benzoyl)-N-(2,6-difluorophenyl)-5,6-dihydro-4H-dithieno[3,2-b:2',3'-d]azepine-8-carboxamide;

N-(2,6-difluorophenyl)-4-(4-(5-methyl-2-(3-oxa-9-azaspiro[5.5]undecan-9-yl)nicotin amido)benzoyl)-5,6-dihydro-4H-dithieno[3,2-b:2',3'-d]azepine-8-carboxamide;

and pharmaceutically acceptable salts of any one thereof.

16. A method of treatment of a subject infected with RSV infection, which comprises administering to said subject an effective amount of a compound according to claim 1.

17. A method according to claim 16 wherein the RSV infection is infection by viruses of the RSV A strain and/or viruses of the RSV B strain.

18. A pharmaceutical composition comprising a compound according to claim 1 optionally in combination with one or more pharmaceutically acceptable diluents or carriers.

19. A pharmaceutical composition according to claim 18 which comprises a second or further active ingredient.

20. A pharmaceutical composition according to claim 19 wherein the second or further active ingredient is selected from anti-viral agents including F protein inhibitors, RNA polymerase inhibitors and ribavirin and anti-inflammatory agents.

* * * * *